United States Patent
Fischer et al.

(10) Patent No.: US 8,652,782 B2
(45) Date of Patent: *Feb. 18, 2014

(54) COMPOSITIONS AND METHODS FOR DETECTING, IDENTIFYING AND QUANTITATING MYCOBACTERIAL-SPECIFIC NUCLEIC ACIDS

(75) Inventors: Gerald W. Fischer, Bethesda, MD (US); Luke T. Daum, San Antonio, TX (US)

(73) Assignee: Longhorn Vaccines & Diagnostics, LLC, San Antonio, TX (US)

( * ) Notice: Subject to any disclaimer, the term of this patent is extended or adjusted under 35 U.S.C. 154(b) by 17 days.

This patent is subject to a terminal disclaimer.

(21) Appl. No.: 13/094,809

(22) Filed: Apr. 26, 2011

(65) Prior Publication Data

US 2011/0281754 A1 Nov. 17, 2011

Related U.S. Application Data

(63) Continuation-in-part of application No. 12/916,263, filed on Oct. 29, 2010, and a continuation-in-part of application No. 12/426,890, filed on Apr. 20, 2009, now Pat. No. 8,080,645, which is a continuation-in-part of application No. 12/243,949, filed on Oct. 1, 2008, now Pat. No. 8,084,443, application No. 13/094,809, which is a continuation-in-part of application No. 12/510,968, filed on Jul. 28, 2009, now Pat. No. 8,097,419, and a continuation-in-part of application No. 11/844,933, filed on Aug. 24, 2007, now abandoned.

(60) Provisional application No. 60/976,728, filed on Oct. 1, 2007, provisional application No. 60/843,711, filed on Sep. 12, 2006.

(51) Int. Cl.
- *C12Q 1/68* (2006.01)
- *C07H 21/04* (2006.01)

(52) U.S. Cl.
USPC ..... 435/6.12; 435/6.15; 536/23.1; 536/24.33; 536/24.32

(58) Field of Classification Search
None
See application file for complete search history.

(56) References Cited

U.S. PATENT DOCUMENTS

| | | |
|---|---|---|
| 1,307,416 A | 6/1919 | Pine |
| 4,116,777 A | 9/1978 | Takatsy et al. |
| 4,196,265 A | 4/1980 | Koprowski et al. |
| 4,235,244 A | 11/1980 | Abele et al. |
| 4,315,073 A | 2/1982 | Brown et al. |
| 4,355,102 A | 10/1982 | Quash |
| 4,356,170 A | 10/1982 | Jennings et al. |
| 4,371,091 A | 2/1983 | Gelina |
| 4,372,945 A | 2/1983 | Likhite |
| 4,474,757 A | 10/1984 | Arnon et al. |
| 4,529,702 A | 7/1985 | Bryan |
| 4,554,101 A | 11/1985 | Hopp |
| 4,559,231 A | 12/1985 | Bjerre et al. |
| 4,578,770 A | 3/1986 | Mitani |
| 4,588,680 A | 5/1986 | Bucher et al. |
| 4,596,792 A | 6/1986 | Vyas |
| 4,599,230 A | 7/1986 | Milich et al. |
| 4,601,903 A | 7/1986 | Frasch |
| 4,608,251 A | 8/1986 | Mia |
| 4,634,664 A | 1/1987 | Oestberg |
| 4,634,666 A | 1/1987 | Engleman et al. |
| 4,668,476 A | 5/1987 | Bridgham et al. |
| 4,683,195 A | 7/1987 | Mullis et al. |
| 4,683,202 A | 7/1987 | Mullis |
| 4,707,450 A | 11/1987 | Nason |
| 4,744,982 A | 5/1988 | Hunter et al. |
| 4,746,490 A | 5/1988 | Saneii |
| 4,749,490 A | 6/1988 | Smyth et al. |
| 4,800,159 A | 1/1989 | Mullis et al. |
| 4,803,998 A | 2/1989 | Kezes et al. |
| 4,816,513 A | 3/1989 | Bridgham et al. |
| 4,883,750 A | 11/1989 | Whiteley et al. |
| 4,954,449 A | 9/1990 | Hunter et al. |
| 4,981,782 A | 1/1991 | Judd et al. |
| 4,996,143 A | 2/1991 | Heller et al. |
| 5,091,316 A | 2/1992 | Monthony et al. |
| 5,108,927 A | 4/1992 | Dorn |
| 5,136,019 A | 8/1992 | Judd et al. |
| 5,149,653 A | 9/1992 | Roser |
| 5,163,441 A | 11/1992 | Monthony et al. |

(Continued)

FOREIGN PATENT DOCUMENTS

| | | |
|---|---|---|
| EP | 0313224 | 4/1989 |
| EP | 320308 | 6/1989 |

(Continued)

OTHER PUBLICATIONS

Henke et al. Nucleic Acids Research (1997) 25(19): 3957-3958.*

(Continued)

*Primary Examiner* — Angela M Bertagna

(74) *Attorney, Agent, or Firm* — Remenick PLLC

(57) ABSTRACT

Disclosed are compositions and methods for isolating, detecting, amplifying, and quantitating *Mycobacterium*-specific nucleic acids in a sample. Also disclosed are compositions and diagnostic kits comprising *Mycobacterium* IS6110-specific oligonucleotide amplification primers and labeled oligonucleotide detection probes that specifically bind to the amplification products obtained therefrom. Also disclosed are compositions and methods for the isolation and characterization of nucleic acids that are specific to one or more tubercular pathogens, including *Mycobacterium tuberculosis*, in particular, from a wide variety of samples including those of biological, environmental, clinical and/or veterinary origin.

61 Claims, 6 Drawing Sheets

(56) References Cited

U.S. PATENT DOCUMENTS

| | | | |
|---|---|---|---|
| 5,168,039 A | * | 12/1992 | Crawford et al. .......... 536/24.32 |
| 5,182,109 A | | 1/1993 | Tamura et al. |
| 5,186,898 A | | 2/1993 | Bridgham et al. |
| 5,187,060 A | | 2/1993 | Cerutti et al. |
| 5,234,809 A | | 8/1993 | Boom et al. |
| 5,243,030 A | | 9/1993 | Judd et al. |
| 5,252,458 A | | 10/1993 | Liav et al. |
| 5,290,686 A | | 3/1994 | Kendal et al. |
| 5,316,910 A | | 5/1994 | Rota et al. |
| 5,399,363 A | | 3/1995 | Liversidge et al. |
| 5,482,856 A | | 1/1996 | Fell, Jr. et al. |
| 5,503,841 A | | 4/1996 | Doyle et al. |
| 5,543,158 A | | 8/1996 | Gref et al. |
| 5,545,555 A | | 8/1996 | Racioppi et al. |
| 5,552,157 A | | 9/1996 | Yagi et al. |
| 5,565,213 A | | 10/1996 | Nakamori et al. |
| 5,565,322 A | | 10/1996 | Heller |
| 5,567,434 A | | 10/1996 | Szoka, Jr. |
| 5,571,511 A | | 11/1996 | Fischer |
| 5,589,174 A | | 12/1996 | Okuno et al. |
| 5,627,071 A | | 5/1997 | Triva |
| 5,631,350 A | | 5/1997 | Okuno et al. |
| 5,641,515 A | | 6/1997 | Ramtoola |
| 5,663,055 A | | 9/1997 | Turner et al. |
| 5,679,356 A | | 10/1997 | Bonnem et al. |
| 5,691,299 A | | 11/1997 | Fabry |
| 5,697,899 A | | 12/1997 | Hillman et al. |
| 5,702,944 A | | 12/1997 | Racioppi et al. |
| 5,719,020 A | | 2/1998 | Liav et al. |
| 5,736,333 A | * | 4/1998 | Livak et al. ............. 435/6.12 |
| 5,738,868 A | | 4/1998 | Shinkarenko |
| 5,741,516 A | | 4/1998 | Webb et al. |
| 5,766,841 A | | 6/1998 | Liav et al. |
| 5,785,975 A | | 7/1998 | Parikh |
| 5,795,582 A | | 8/1998 | Wright |
| 5,800,810 A | | 9/1998 | Doyle et al. |
| 5,849,489 A | | 12/1998 | Heller |
| 5,891,624 A | | 4/1999 | Huang |
| 5,945,515 A | | 8/1999 | Chomczynski |
| 5,955,074 A | | 9/1999 | Fischer |
| 5,958,379 A | | 9/1999 | Regenold et al. |
| 6,015,664 A | | 1/2000 | Henrickson et al. |
| 6,033,673 A | | 3/2000 | Clements |
| 6,060,068 A | | 5/2000 | Doyle et al. |
| 6,136,585 A | | 10/2000 | Ball et al. |
| 6,162,603 A | | 12/2000 | Heller |
| 6,168,915 B1 | | 1/2001 | Scholl et al. |
| 6,242,582 B1 | | 6/2001 | Reece et al. |
| 6,280,928 B1 | | 8/2001 | Scholl et al. |
| 6,306,404 B1 | | 10/2001 | LaPosta et al. |
| 6,306,582 B1 | | 10/2001 | Scholl et al. |
| 6,312,395 B1 | | 11/2001 | Tripp et al. |
| 6,376,172 B1 | | 4/2002 | Scholl et al. |
| 6,406,842 B2 | | 6/2002 | Scholl et al. |
| 6,440,423 B1 | | 8/2002 | Clements et al. |
| 6,451,325 B1 | | 9/2002 | Van Nest et al. |
| 6,458,577 B1 | | 10/2002 | Huang |
| 6,495,316 B1 | | 12/2002 | Scholl et al. |
| 6,500,432 B1 | | 12/2002 | Dalemans et al. |
| 6,503,745 B1 | | 1/2003 | Chand et al. |
| 6,534,065 B1 | | 3/2003 | Makin et al. |
| 6,572,866 B1 | | 6/2003 | Torcia |
| 6,573,080 B2 | | 6/2003 | Scholl et al. |
| 6,602,510 B1 | | 8/2003 | Fikes et al. |
| 6,603,908 B2 | | 8/2003 | Dallas et al. |
| 6,603,998 B1 | | 8/2003 | King et al. |
| 6,610,293 B1 | | 8/2003 | Fischer et al. |
| 6,610,474 B1 | | 8/2003 | Huang |
| 6,627,396 B1 | | 9/2003 | Swanson et al. |
| 6,632,432 B1 | | 10/2003 | Fischer |
| 6,680,308 B1 | | 1/2004 | Hassan |
| 6,689,363 B1 | | 2/2004 | Sette et al. |
| 6,713,068 B1 | | 3/2004 | Audonnet et al. |
| 6,720,409 B2 | | 4/2004 | Okuno et al. |
| 6,734,292 B1 | | 5/2004 | Omura et al. |
| 6,759,241 B1 | | 7/2004 | Hone et al. |
| 6,780,421 B1 | | 8/2004 | Haensler et al. |
| 6,793,928 B1 | | 9/2004 | van Scharrenburg et al. |
| 6,811,971 B2 | | 11/2004 | Klepp et al. |
| 6,855,321 B1 | | 2/2005 | Rappuoli et al. |
| 6,875,600 B2 | | 4/2005 | Scholl et al. |
| 6,881,835 B2 | | 4/2005 | Bai et al. |
| 6,893,814 B2 | | 5/2005 | Swanson et al. |
| 6,939,543 B2 | | 9/2005 | Fischer et al. |
| 6,946,291 B2 | | 9/2005 | Scholl et al. |
| 7,090,853 B2 | | 8/2006 | Kapp et al. |
| 7,122,640 B2 | | 10/2006 | Gjerde et al. |
| 7,223,409 B2 | | 5/2007 | Nagata et al. |
| 7,279,162 B1 | | 10/2007 | Fischer |
| 7,311,671 B2 | | 12/2007 | Jung et al. |
| 7,351,413 B2 | | 4/2008 | Page et al. |
| 7,357,936 B1 | | 4/2008 | Garcon |
| 7,361,352 B2 | | 4/2008 | Birkett et al. |
| 7,494,771 B2 | | 2/2009 | Picard et al. |
| 7,541,194 B2 | | 6/2009 | Mink et al. |
| 7,648,681 B2 | | 1/2010 | Meyer et al. |
| 7,718,402 B2 | | 5/2010 | Gayral et al. |
| 7,794,001 B2 | | 9/2010 | Blackwell et al. |
| 8,080,645 B2 | | 12/2011 | Fischer et al. |
| 8,084,443 B2 | * | 12/2011 | Fischer et al. ............. 514/75 |
| 8,097,419 B2 | | 1/2012 | Fischer et al. |
| 8,293,467 B2 | * | 10/2012 | Fischer et al. ............. 435/5 |
| 2001/0021501 A1 | | 9/2001 | Scholl et al. |
| 2001/0034022 A1 | | 10/2001 | Scholl et al. |
| 2001/0036628 A1 | | 11/2001 | Scholl et al. |
| 2002/0054882 A1 | | 5/2002 | Okuno et al. |
| 2002/0055094 A1 | | 5/2002 | Reece et al. |
| 2002/0081567 A1 | | 6/2002 | Henrickson et al. |
| 2002/0082395 A1 | | 6/2002 | Fischer et al. |
| 2002/0169140 A1 | | 11/2002 | Prendergast |
| 2003/0119209 A1 | | 6/2003 | Kaylor et al. |
| 2003/0203357 A1 | | 10/2003 | Huang |
| 2003/0215796 A1 | | 11/2003 | Scholl et al. |
| 2003/0219442 A1 | | 11/2003 | Mikayama et al. |
| 2004/0009126 A1 | | 1/2004 | Pilkiewicz et al. |
| 2004/0013673 A1 | | 1/2004 | Fischer et al. |
| 2004/0071757 A1 | | 4/2004 | Rolf |
| 2004/0082549 A1 | | 4/2004 | Jomaa |
| 2004/0086849 A1 | | 5/2004 | Shimasaki et al. |
| 2004/0101869 A1 | * | 5/2004 | Berg et al. ............. 435/6 |
| 2004/0126789 A1 | | 7/2004 | Park et al. |
| 2004/0142319 A1 | | 7/2004 | Yu et al. |
| 2004/0170965 A1 | | 9/2004 | Scholl et al. |
| 2004/0214272 A1 | | 10/2004 | La Rosa et al. |
| 2004/0223976 A1 | | 11/2004 | Bianchi et al. |
| 2005/0009008 A1 | | 1/2005 | Robinson et al. |
| 2005/0042229 A1 | | 2/2005 | Yang et al. |
| 2005/0090009 A1 | | 4/2005 | Cormier et al. |
| 2005/0112656 A1 | * | 5/2005 | Iwaki ............. 435/6 |
| 2005/0169941 A1 | | 8/2005 | Lees |
| 2005/0170334 A1 | | 8/2005 | Mikayama et al. |
| 2005/0181357 A1 | | 8/2005 | Peiris et al. |
| 2005/0187213 A1 | | 8/2005 | Lang et al. |
| 2005/0227269 A1 | | 10/2005 | Lloyd, Jr. et al. |
| 2006/0002939 A1 | | 1/2006 | Fischer et al. |
| 2006/0014185 A1 | | 1/2006 | Ollikka et al. |
| 2006/0105461 A1 | * | 5/2006 | Winkler et al. ............. 436/174 |
| 2006/0121468 A1 | | 6/2006 | Allnutt et al. |
| 2006/0134648 A1 | * | 6/2006 | Chou et al. ............. 435/6 |
| 2006/0286557 A1 | | 12/2006 | Basehore et al. |
| 2007/0078025 A1 | | 4/2007 | Pepe |
| 2007/0102946 A1 | | 5/2007 | Blackwell et al. |
| 2007/0172835 A1 | | 7/2007 | McBride et al. |
| 2007/0196388 A1 | | 8/2007 | Dowling et al. |
| 2007/0202497 A1 | | 8/2007 | Renuart et al. |
| 2007/0202511 A1 | | 8/2007 | Chen et al. |
| 2007/0286871 A1 | | 12/2007 | Hickle et al. |
| 2008/0032921 A1 | | 2/2008 | Alexander et al. |
| 2008/0050737 A1 | | 2/2008 | Arieli et al. |
| 2008/0069821 A1 | | 3/2008 | Yang et al. |
| 2008/0075708 A1 | | 3/2008 | Yu et al. |
| 2008/0078499 A1 | | 4/2008 | Feeney |
| 2008/0107665 A1 | | 5/2008 | Suckow et al. |
| 2008/0107687 A1 | | 5/2008 | Poulet |

(56) References Cited

U.S. PATENT DOCUMENTS

| | | |
|---|---|---|
| 2008/0118531 A1 | 5/2008 | Hoffmann et al. |
| 2008/0139789 A1 | 6/2008 | Fischer |
| 2008/0145373 A1 | 6/2008 | Arumugham et al. |
| 2008/0181914 A1 | 7/2008 | Eichhorn |
| 2008/0260763 A1 | 10/2008 | Felgner et al. |
| 2009/0081202 A1 | 3/2009 | Fischer et al. |
| 2009/0098527 A1 | 4/2009 | Fischer et al. |
| 2009/0233309 A1 | 9/2009 | Fischer et al. |
| 2009/0312285 A1 | 12/2009 | Fischer et al. |
| 2010/0009343 A1 | 1/2010 | Fischer et al. |
| 2010/0055672 A1 | 3/2010 | Saghbini |
| 2010/0151477 A1 | 6/2010 | Cawthon |
| 2010/0221822 A1 | 9/2010 | Fischer et al. |
| 2010/0311739 A1 | 12/2010 | Gunaratnam et al. |
| 2011/0281754 A1 | 11/2011 | Fischer et al. |
| 2012/0088231 A1 | 4/2012 | Fischer et al. |
| 2012/0100529 A1 | 4/2012 | Fischer et al. |
| 2012/0107799 A1 | 5/2012 | Daum |
| 2012/0115126 A1 | 5/2012 | Fischer et al. |

FOREIGN PATENT DOCUMENTS

| | | |
|---|---|---|
| EP | 0621339 | 10/1994 |
| EP | 0675199 | 10/1995 |
| EP | 0726316 | 8/1996 |
| EP | 1081496 | 3/2001 |
| RU | 2150281 | 6/2000 |
| WO | WO 91/02740 | 3/1991 |
| WO | WO9203454 | 3/1992 |
| WO | WO9216619 | 10/1992 |
| WO | WO9409035 | 4/1994 |
| WO | WO9417106 | 8/1994 |
| WO | WO 95/08348 | 3/1995 |
| WO | WO9705248 | 2/1997 |
| WO | WO 97/46707 | 12/1997 |
| WO | WO 97/46712 | 12/1997 |
| WO | WO 97/46714 | 12/1997 |
| WO | WO01/16163 | 3/2001 |
| WO | WO03026567 | 4/2003 |
| WO | WO 03/053462 | 7/2003 |
| WO | WO2004/002451 | 1/2004 |
| WO | WO2004004658 | 1/2004 |
| WO | WO 2004/043407 | 5/2004 |
| WO | WO2004055205 | 7/2004 |
| WO | WO2004072270 | 8/2004 |
| WO | WO2004084876 | 10/2004 |
| WO | WO 2005010186 A1 * | 2/2005 |
| WO | WO2005075642 | 8/2005 |
| WO | WO2005085274 | 9/2005 |
| WO | WO2006/041933 | 4/2006 |
| WO | WO 2006/138444 | 12/2006 |
| WO | WO 2007/051036 | 5/2007 |
| WO | WO 2007/056266 | 5/2007 |
| WO | WO2007056266 | 5/2007 |
| WO | WO 2007/091030 | 8/2007 |
| WO | WO2007133682 | 11/2007 |
| WO | WO 2008/079463 | 7/2008 |
| WO | WO 2009/085355 | 7/2009 |

OTHER PUBLICATIONS

Yue et al. Diagnostic Microbiology and Infectious Disease (2004) 48(1): 47-54.*

CA Office action for PCT/US08/78499, dated Mar. 29, 2012.

"Development of an Internal Positive Control for Rapid Diagnosis of Avian Influenza, etc.", A.Das, et al., Journal of Clinical Microbiology, Sep. 2006, vol. 44, No. 9, pp. 3065-3073.

De Moreau de Gerbehaye, A.I. et al., "Stable Hepatitis C Virus RNA Detection by RT-PCR During Four Days Storage," BioMed Central, BMC Infectious Diseases, 2:22 (2002).

"Evaluation of PCR Testing of Ethanol-Fixed Nasal Swab Specimens, etc." A.Krafft, et al., Journal of Clinical Microbiology, Apr. 2005, vol. 43, No. 4, pp. 1768-1775.

"Abstracts—27th Annual Meeting for the European Society for Paediatric Infectious Disease, Brussels, Belgium, Jun. 9-13, 2009," The Ped. Infect. Dis. J., 28(6):e1, e75, e229 (Jun. 2009).

"AgPath-ID One-Step RT-PCR Kit," Applied Biosystems, available at http://www.abion.com/techlib/prot/bp_1005.pdf (last visited Aug. 24, 2009).

Lin, B., et al., "Broad-Spectrum Respiratory Tract Pathogen Identification Using Resequencing DNA Microarrays." Genome Res., 16:527-35 (2006).

Buck et al. BioTechniques vol. 27, pp. 528-536, Sep. 1999.

Wolff, C. et al, "Single-Tube Nested PCR With Room-Temperature-Stable Reagents," Cold Spring Harbor Laboratory Press, PCR Methods and Appl., 4:376-79 (1995).

Schultz, C.L., et al., "A Lysis, Storage, and Transportation Buffer for Long-Term, Room-Temperature Preservation of Human Clinical Lymphoid Tissue Samples Yielding High Molecular Weight Genomic DNA Suitable for Molecular Diagnosis," Am. J. Clin. Pathol., 111(6):748-52 (1999).

"Collecting, Preserving, Shipping Specimens for the Diagnosis of Avian Influenza (H5N1) Virus Infection: Guide for Field Operations," WHO/CDS/EPR/ARO/2006.1 (2006).

Daum, et al., Abstract—"A Molecular Transport Medium (MTM) for Pathogen Inactivation, Ambient Transport and Preservation of RNA from Clinical Samples," ICAAC, Boston, MA, Sep. 12-15, 2010.

Daum, et al., Abstract and Poster—"Development of a Real Time Reverse-Transcription PCR (RRT-PCR) Assay for Detection of Influenza a H1N1 2009 from Clinical Respiratory Specimens," Pediatric Infectious Disease Conference ESPID, Nice, France, May 5-8, 2010.

De Silva at al. Influenza A virus (A/Nonthaburi/102/2009(H1N1)) segment 4 hemagglutinin (HA) gene, partial cds. Genbank Accession No. GQ 132184.1, submitted May 9, 2009.

Spackman, E., et al., "Development of a Real-Time Reverse Transcriptase PCR Assay for Type A Influenza Vrius and the Avian H5 and H7 Hemagglutinin Subtypes," J. Clinic. Mirobiol., 40(9): 3256-60 (2002).

Hindiyeh et al. Journal of Clinical Microbiology, vol. 43, No. 2, pp. 589-595, Feb. 2005.

J. Mahoney et al., "Multiplex RT-PCR for detecting nineteen respiratory viruses," Journal of Clinical Virology, vol. 36, Jan. 1, 2006, p. S9.

"Adamantane Resistance Among Influenza, etc.", JAMA, Feb. 22, 2006, vol. 295, No. 8, pp. 891-894, Bright et al.

Jamie A. Blow et al., "Viral nucleic acid stabilization by RNA extraction reagent," Journal of Virological Methods, 150 (2008), Feb. 4, 2008, pp. 41-44.

"KOD Hot Start DNA Polymerase," Novagen, available at http://www.emdbiosciences.com/ProductDisplay.asp?catno=71086 (last visited Aug. 24, 2009).

Kutyavin et al. 3'-Minor groove binder-DNA probes increase sequence specificity at PCR extension temperatures. Nucleic Acid Res. (2000) vol. 28, No. 2, pp. 655-661.

"Genetic and Antigenic Analysis of the First A/New Calendonia, etc.", L.Daum, et al., Emerging Infectious Diseases, vol. 8, No. 4, Apr. 2002, pp. 408-412.

Canas, L.C., "Clinical Laboratory: Selection, Collection and Transport of Specimens for Viral Cultures." Department of the Air Force, Air Force Institute of Operational Health (AFIOH), Epidemiological Surveillance Division, SDE O1 44/5001, Virol. Proc. Man., 1-8 (2005).

Daum, L.T. et al., "Real-Time RT-PCR Assays for Type and Subtype Detection of Influenza A and B Viruses," Influenza & Other Resp. Viruses 1(4): 167-75 (2007).

Daum, L.T., et al., "Abstract—Quantification of Influenza A Virus From Nasal and Lung Tissue of Cotton Rats Using Real-Time RT-PCR and Culture," 26th Annual Meeting of the European Society for Pediatric Infectious Diseases, Graz, Austria (2008).

Daum, L.T., et al., "Abstract—Development and Clinical Evaluation of Rapid Real-Time RT-PCR Assays for Detection of Influenza A and B Viruses," 26th Annual Meeting of the European Society for Pediatric Infectious Diseases, Graz, Austria (2008).

(56) References Cited

OTHER PUBLICATIONS

Daum, L.T., et al., "Poster—A Novel Specimen Collection Solution for Molecular Diagnostic Applications," The Pediatric Academic Societies (PAS) Annual Meeting, Honolulu, HI (2008).
Daum, L.T., et al., "Poster—A Rapid, Simplified Collection-to-Detection System for Typing and Subtyping Influenza Viruses Using Real-Time RT-PCR and Culture," American Society for Microbiology (ASM) Conference on Emerging Technologies of Medical Importance for the Diagnosis of Infectious Diseases and the Detection of Pathogenic Microbes, Beijing, China (2008).
Daum, L.T., et al., "Poster—Real-Time RT-PCR Detection of Influenza A Virus in Asymptomatic Culture-Negative Cotton Rats," The Pediatric Academic Societies (PAS) Annual Meeting, Honolulu, HI (2008).
Daum, L.T., et al., "A Rapid, Single-Step Multiplex Reverse Transcription-PCR Assay for the Detection of Human H1N1, H3N2 and B Influenza Viruses." J. of Clinic. Virol., 25(3): 345-50 (2002).
Daum, L.T., et al., "Real-Time RT-PCR Detection of Influenza Virus Within Symptomatic and Asymptomatic Family Members," The 48th Annual IDSA/ICAAC, Washington D.C. (2008).
Lowe et al. A computer program for selection of oligonucleotide primers for polymerase chain reactions. Nucleic Acids Research (1990) vol. 18, No. 7, pp. 1757-1761.
Luke T. Daum et al., "Detection and Molecular Characterization of Clinical Influenza A and B Viruses from Original Nasal Wash Specimens Preserved in PrimeStore," (2008).
Luke T. Daum et al., "Portugal Meeting Poster (Introduction, Materials, and Methods, Results, Discussion)," (2008).
"Luminex Confirms Effectiveness of xTAG Respiratory Viral Panel for Swine Flu Surveillance," Medical News Today, available at http://www.medicalnewstoday.com/printerfriendlynews.php?newsid=148498 (May 1, 2009).
"Luminex Receives FDA Clearance for an Update to the xTAG Respiratory Panel Insert Package Insert to Include Data from Two New Publications on 2009 Influenza A/H1N1," available at http://phx.corporate-ir.net/phoenix.zhtml?c=79403&p=irol-newsArticle&ID=1307416&highlight= (Jul. 14, 2009).
Borns, M. et al., "Most Accurate PCR Enzyme Inproved With Hot Start Feature," Biocompare, available at http://www.biocompare.com/technicalarticle/212/Most-Accurate-PCR-Enzyme-Improved-With-Hot-Start-Feature-from-Startagene.html (last visited Aug. 24, 2009).
Denhart, M., and Doraiswamy, V., "Master Your PCR Domain!" Promega Notes, 78: 9-12 (2001).
"Tools of Biochemistry 5A—Ways to Isolate and Purify Proteins and Other Macromolecules", Matthews, et al., Biochemistry, Second Edition, 1996, pp. 152-155.
Tortora, et al., "Tools of Biochemistry 5A—Ways to Isolate and Purify Proteins and Other Macromolecules," Microbiology—An Introduction, pp. 152-55, 4th Ed., The Benjamin/Cummings Publishing Company, Inc., United States (1992).
Matthews, et al., "Immunofluorescence and Fluorescent Antibody Techniques," Biochemistry, pp. 461-63, 2nd Ed., The Benjamin/Cummings Publishing Company, Inc., United States (1996).
Morre, et al., "RNA Amplification by Nucleic Acid Sequence-Based Amplification with an Internal Standard Enables Reliable Detection of *Chlamydia trachomatis* in Cervical Scrapings and Urine Samples," J. of Clinical Microbiol, 34(12): 3108-3114 (1996).
http://www.ncbi.nim.nih.gov/genomes/Flu/SwineFlu2009.html.
NCBI Influenza Virus Resource "CLE I. GenBank Sequence from Pandemic (H1N1) 2009 Viruses". 1237 pages.
Pheng, O.C. Et al., "Temperature Related Storage Evaluation of an RT-PCR Test Kit for the Detection of Dengue Infection in Mosquitoes," (Research Note), Tropical Biomedicine, 22(1):73-6 (2005).
"Single-Step Method of RNA Isolation by Acid Guanidinium, etc.", P. Chomczyniski, et al., Analytical Biochemistry 162, 1987, pp. 156-159.
"PCR Optimization: Reaction Conditions and Components," Applied Biosystems, Part No. 4371091, Revision C, pp. 1-6 available at http://www.appliedbiosystems.com/cms/groups/mcb_marketing/documents/generaldocuments/cms_042520.pdf (last visited Aug. 24, 2009).
"PCR-Ready Clear Supreme," Syntezza Bioscience Ltd., available at http://www.syntezza.com/egt/PCR-Ready_Clear Supreme.pdf (2006).
European Patent Office, "PCT Notification of Transmittal of the International Search Report and the Written Opinion of the International Searching Authority or the Declaration, PCT International Search Report, PCT Written Opinion of the International Searching Authority—Application No. PCT/US2007/078025," Nov. 13, 2008, 10 pages, Munich.
European Patent Office, "PCT Notification of Transmittal of the International Search Report and the Written Opinion of the International Searching Authority—Application No. PCT/US2008/078499," mailed Aug. 4, 2009, 13 pages.
Ramanujam, R. et al., "Room-Temperature-Stable PCR Reagents," Cold Spring Harbor Laboratory Press, PCR Methods and Appl., 3:75-76 (1993).
Bright, R.A., et al., "Adamantane Resistance Among Influenza A Viruses Isolated Early During the 2005-2006 Influenza Season in the United States," JAMA, 295(8):891-4 (Feb. 22, 2006).
Fouchier, R.A.M. et al., "Characterization of a Novel Influenza A Virus Hemagglutinin Subtype (H16) Obtained From Black-Headed Gulls," J. of Virol. 79(5):2814-22 (Mar. 2005).
"R.A.P.I.D System," Idaho Technology Inc., available at http://www.idahotech.com/Rapid/Rapid-Water.html (last visited Aug. 24, 2009).
Magari, R.T., Assessing shelf life using real-time and accelerated stability tests, BioPharm Nov. 2003.
Rosenstraus, et al., "An Internal Control for Routine Diagnostic PCR: Design, Properties, and Effect on Clinical Performance," J. of Clinical Microbial, 36(1): 191-197 (1998).
Blacksell, S.D. et al., "The Effect of Sample Degradation and RNA Stabilization on Classical Swine Fever Virus RT-PCR and ELISA methods," J. Virol. Methods, 118(1):33-7 (2004).
"Single Tube PCR Kit Manual," Takara Bio Inc., Cat #RR021, V.02. 09, pp. 1-6 available at http://www.takara-bio.us/files/manuels/TAK_RR021_TM.pdf (last visited Aug. 24, 2009).
"Taq PCR Master Mix (2x)," USB Corp., (2007).
"Immunoflourescence and Fluorescent-Antibody Techniques", Tortora, et al., Microbiology—An Introduction, Fourth Edition, 1992, pp. 461-463.
Wiecek, A., "Pocket PCR: The Whole Chain Reaction in His Hand," Biotechniques.com, Oct. 26, 2010.
Wang, Z., et al., "Identifying Influenza Viruses with Resequencing Microarrays," Emerg. Infect. Dis. 12(4):638-46 (2006).
Danila Valmori et al. "Use of human universally antigenic tetanus toxin T cell epitopes as carriers for human vaccination" Journal of Immunology Jul. 15, 1992.
PCT Search Report for PCT/US2008/074521 dated Feb. 13, 2009.
PCT Written Opinion for PCT/US2008/074521 dated May 3, 2009.
PCT Search Report for PCT/US10/43546 dated Nov. 16, 2010.
PCT Search Report for PCT/US10/31716 dated Jul. 28, 2010.
PCT Written Opinion for PCT/US10/31716 dated Oct. 25, 2011.
De Folette et al. Vaccine Jun. 12, 2006, vol. 24, No. 44-46, pp. 6597-6601.
Galarza et al. Viral Immunity 2005, vol. 18, No. 2, pp. 365-372.
Arend et al. Infection and Immunity, 2000, vol. 68, No. 6, pp. 3314-3321.
Geysen, et al., "Use of Peptide Synthesis to Probe Viral Antigens for Epitopes to a Resolution of a Single Amino Acid," Proc. Natl. Acad. Sci., 81, pp. 3998-4002 (1984).
Tolman, et al., "Cyclic V3-Loop Related HIV-1 Conjugate Vaccines," Int. J. Peptide Protein Res., 41, pp. 455-466 (1993).
Conley, et al., "Immunogenicity of Synthetic HIV-1 Gp120 V3-Loop Peptide-Conjugate Immunogens," Vaccine, 12(5), pp. 445-451 (1994).
Schneider, et al., "Induction of CD8+T Cells Using Heterologous Prime-Boost Immunisation Strategies," Immunol. Rev., 170, pp. 29-38 (1999).
Tanghe, et al., "Improved Immunogenicity and Protective Efficacy of a Tuberculosis DNA Vaccine Encoding Ag85 by Protein Boosting," Infect. and Immun., 69(5), pp. 3041-3047 (2001).

(56) References Cited

OTHER PUBLICATIONS

Gonzalo, et al., "A Heterologous Prime-Boost Regime Using DNA and Recombinant Vaccinia Virus Expressing the Leishmania infantum P36/LACK Antigen Protects BALB/c Mice from Cutaneous Leishmaniasis," Vaccine, 20, pp. 1226-1231 (2002).
Meyer, et al., "Complement-Mediated Enhancement of Antibody Function for Neutralization of Pseudotype Virus Containing Hepatitis C Virus E2 Chimeric Glycoprotein," J. of Virol., 76(5) pp. 2150-2158 (2002).
Robinson, "New Hope for an AIDS Vaccine," Nat. Rev. Immunol., 2, pp. 239-250 (Apr. 2002).
Lu, et al., "Multiepitope Trojan Antigen Peptide Vaccines for the Induction of Antitumor CTL and Th Immune Responses," J. of Immunol., 172, pp. 4575-4582 (2004).
Westerfield, et al., "Peptides Delivered by Immunostimulating Reconsituted Influenza Virosomes," J. of Peptide Sci., 11(11), pp. 707-712 (2005).
Gerhard, et al., "Prospects for Universal Influenza Virus," Emerging Infectious Diseases, 12(4), pp. 569-574 (Apr. 2006).
Luo, "Structural Biology: Antiviral Drugs Fit for a Purpose," Nature, 443, pp. 37-38 (Sep. 1, 2006).
PepTcell Ltd., "Technology," http://www.peptcell.com/technology.aspx (2007).
Stoloff, et al., "Synthetic Multi-Epitope Peptides Idenitifed in Silico Induce Protective Immunity Against Multiple Influenza Serotypes," Eur. J. of Immunol., 37(9), pp. 2441-2449 (Aug. 2, 2007).
Depla, et al., "Rational Design of a Multiepitope Vaccine Encoding T-Lymphocyte Epitopes for Treatment of Chronic Hepatitis B Virus Infections," J. of Virol., 82(1), pp. 435-450 (Jan. 2008).
Chien et al. J. Clin. Microbiol. 1999, vol. 37, No. 5, 1393-1397.
Ishioka et al. J. Immunol. vol. 162, pp. 3915-3925, 1999.
Lederman et al. Molecular Immunology 1991, vol. 28, No. 11, pp. 1171-1181.
PCT Search Report for PCT/US2007/078025 dated Oct. 28, 2008.
PCT Written Opinion for PCT/US2007/078025 dated Mar. 17, 2009.
PCT Search Report for PCT/US2008/078499 dated Jul. 23, 2009.
CA Office Action for PCT/US2007/078025, dated Jan. 4, 2011.
EPO Exam Report for PCT/US2007/078025, dated Dec. 30, 2011.
EPO Exam Report for PCT/US2007/078025, dated Aug. 26, 2010.
EPO Exam Report for PCT/US2007/078025, dated Jul. 6, 2009.
EPO Exam Report for PCT/US2007/078025, dated May 18, 2009.
AU Exam Report for PCT/US2007/078025, dated Nov. 19, 2010.
IL Exam Report for PCT/US2007/078025, dated Mar. 16, 2011.
NZ Exam Report for PCT/US2007/078025, dated Jul. 7, 2010.
Israel Office Action of Jul. 19, 2012.
EPO Supplementary Search Report for PCT/US10/31761, dated Jul. 13, 2012.
PCT Written Opinion for PCT/US2008/078499, dated Jul. 4, 2010.
"Monolithic Silica Extraction Tips for Sample Preparation," CP-Analytica, available at http://cp-analytica (last visited Oct. 25, 2010).
Barnard, et al., "Suitability of new chlamydia transport medium for transport of herpes simplex virus," J. of Clin. Microbiol., 24(5): 692-695 (1986).
Eroglu, et al., "Successful cyropreservation of mouse oocytes by using low concentrations of trehalose and dimethylsylfoxide," Biol. of Rep. 80:70-78 (2009).
Gelmi, et al., "Bacertial survival in different transport media," European Congress of Clinical Microbiology and Infectious Diseases (ECCMID), May 28-31, 2000 (poster).
Higashiyama, T., "Novel functions and applications of terhalose," Pure Appl. Chem. 74(7): 1263-1269.
H1N1 RTPCR Primer/Probe Sets, Intergrated DNA Technologies—H1N1, available at http://www.idtdna.com/catalog/h1n1/pagel.aspx, 2010.
Johnson, F.B., "Transport of viral specimens," Clin. Microbiol. Rev. 3(2): 120-131 (1990).
Sponseller, et al., "Influenza A pandemic (H1N1) 2009 virus infection in domestic cat," Emerg. Infect. Dis. (e-publication) (2010).
PCT Patentability Report for PCT/US2010/043546, dated Jan. 31, 2012.
PCT Search Report and Patentability Report for PCT/US2008/074521, dated Mar. 2, 2010.
Miyazaki, et al., "Development of a monolithic silica extraction top for the analysis of proteins," J. Chromatogr. A., 1043(1): 19-25 (2004) [abstract only].
PCT Patentability Report for PCT/US2012/35253, dated Sep. 21, 2012.
Taiwan Office Action dated Aug. 20, 2012.
IL Exam Report for PCT/US2007/078025, dated Mar. 7, 2013.
EPO Exam Report for EP12180376, dated Feb. 8, 2013.
Canadian Office Action for application No. 2759028, dated Apr. 12, 2013.
Fouchier, et al., "Characterization of Novel Influenza A Virus Hemagglutinin Subtype (H16) Obtained from Black-Headed Gulls," J. Virol. 79(5):2814-2822 (2005).
Daum, et al., Abstract and Poster—"Development of a Real Time Reverse-Transcription PCR (RRT-PCR) Assay for Detection of Influenza A H1N1 2009 From Clinical Respiratory Specimens," Pediatric Infectious Disease Conference ESPID, Nice, France, May 5-8, 2009.
Daum L.T., et al., "Molecular Analysis of Isolates From Influenza B Outbreaks in the U.S. and Nepal, 2005," Arch. of Virol., 151:1863-1874 (2006).
USB Corp., "USB Taq PCR Master in qPCR," Tech Tip 207 (2005).
World Health Organization, "CDC protocol of realtime RTPCR for influenza A (H1N1)," Apr. 28, 2009.
Canadian Office Action for application No. 2697373, dated Feb. 19, 2013.

\* cited by examiner

SEQUENCE LISTING

<160> NUMBER OF SEQ ID NOS: 21

<210> SEQ ID NO 1
<211> LENGTH: 180
<212> TYPE: DNA
<213> ORGANISM: Mycobacterium tuberculosis

<400> SEQUENCE: 1

```
gtcccgccga tctcgtccag cgccgcttcg gaccaccagc acctaaccgg ctgtgggtag      60
cagacctcac ctatgtgtcg acctgggcag ggttcgccta cgtggccttt gtcaccgacg     120
cctacgtcgc aggatcctgg gctggcgggt cgcttccacg atggccacct ccatggtcct    180
```

<210> SEQ ID NO 2
<211> LENGTH: 18
<212> TYPE: DNA
<213> ORGANISM: Artificial Sequence
<220> FEATURE:
<223> OTHER INFORMATION: Synthetic Oligonucleotide Forward Primer

<400> SEQUENCE: 2

```
ctcgtccagc gccgcttc                                                     18
```

<210> SEQ ID NO 3
<211> LENGTH: 19
<212> TYPE: DNA

```
<213> ORGANISM: Artificial Sequence
<220> FEATURE:
<223> OTHER INFORMATION: Synthetic Oligonucleotide Reverse Primer

<400> SEQUENCE: 3
acaaaggcca cgtaggcga                                                   19

<210> SEQ ID NO 4
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 4
accaccagca cctaaccggc tgtgggta                                          28

<210> SEQ ID NO 5
<211> LENGTH: 18
<212> TYPE: DNA
<213> ORGANISM: Artificial Sequence
<220> FEATURE:
<223> OTHER INFORMATION: Synthetic Oligonucleotide Forward Primer

<400> SEQUENCE: 5
accagcacct aaccggct                                                    18

<210> SEQ ID NO 6
<211> LENGTH: 18
<212> TYPE: DNA
<213> ORGANISM: Artificial Sequence
<220> FEATURE:
<223> OTHER INFORMATION: Synthetic Oligonucleotide Reverse Primer

<400> SEQUENCE: 6
accgacgcct acgtcgca                                                    18

<210> SEQ ID NO 7
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 7
agggttcgcc tacgtggcct ttgt                                             24

<210> SEQ ID NO 8
<211> LENGTH: 124
<212> TYPE: DNA
<213> ORGANISM: Artificial Sequence
<220> FEATURE:
<223> OTHER INFORMATION: Synthetic Oligonucleotide

<400> SEQUENCE: 8
gggatcgtat aatcgtcgtg cagtcagtcc ctcggttaaa gtctcgagtc gctctgtcaa       60
aatatccgta ccgtagtcga tgcgagcgag tccgatcagt ccaggtttca aagtcaaatg      120
acta                                                                  124

<210> SEQ ID NO 9
<211> LENGTH: 21
<212> TYPE: DNA
<213> ORGANISM: Artificial Sequence
<220> FEATURE:
<223> OTHER INFORMATION: Synthetic Oligonucleotide Forward Primer
```

```
<400> SEQUENCE: 9
gtgcagtcag tccctcggtt a                                              21

<210> SEQ ID NO 10
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 10
ttgactttga aacctggact gatc                                           24

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 11
aaatatccgt accgtagtcg                                                20

<210> SEQ ID NO 12
<211> LENGTH: 126
<212> TYPE: DNA
<213> ORGANISM: Artificial Sequence
<220> FEATURE:
<223> OTHER INFORMATION: Synthetic Oligonucleotide  N = any nucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t

<400> SEQUENCE: 12
ntattaatac gactcactat agggngtgca gtcagtccct cggttaaagt ctcgagtcgc     60
tctgtcaaaa tatccgtacc gtagtcgatg cgagcgagtc cgatcagtcc aggtttcaaa    120 gtcaan                                                              126

<210> SEQ ID NO 13
<211> LENGTH: 141
<212> TYPE: DNA
<213> ORGANISM: Artificial Sequence
<220> FEATURE:
<223> OTHER INFORMATION: Synthetic Oligonucleotide

<400> SEQUENCE: 13
atcgtattaa tacgactcac tatagggaat cgtcgtgcag tcagtccctc ggttaaagtc     60
tcgagtcgct ctgtcaaaat atccgtaccg tagtcgatgc gagcgagtcc gatcagtcca    120
ggtttcaaag tcaaatgact a                                             141

<210> SEQ ID NO 14
<211> LENGTH: 141
<212> TYPE: DNA
<213> ORGANISM: Artificial Sequence
<220> FEATURE:
<223> OTHER INFORMATION: Synthetic Oligonucleotide
```

```
<400> SEQUENCE: 14
atcgtattaa tacgactcac tatagggaat cgtcgtgcag tcagtccctc ggttaaagtc      60
tcgagtcgct ctgtcaaaat atccgtaccg tagtcgatgc gagcgagtcc gatcagtcca     120
ggtttcaaag tcaaatgact a                                               141

<210> SEQ ID NO 15
<211> LENGTH: 141
<212> TYPE: DNA
<213> ORGANISM: Artificial Sequence
<220> FEATURE:
<223> OTHER INFORMATION: Synthetic Oligonucleotide

<400> SEQUENCE: 15
atcgtattaa tacgactcac tatagggaat cgtcgtgcag tcagtccctc ggttaaagtc      60
tcgagtcgct ctgtcaaaat atccgtaccg tagtcgatgc gagcgagtcc gatcagtcca     120
ggtttcaaag tcaaatgact a                                               141

<210> SEQ ID NO 16
<211> LENGTH: 127
<212> TYPE: DNA
<213> ORGANISM: Artificial Sequence
<220> FEATURE:
<223> OTHER INFORMATION: Synthetic Oligonucleotide

<400> SEQUENCE: 16
atattaatac gactcactat agggagtgca gtcagtccct cggttaaagt ctcgagtcgc      60
tctgtcaaaa tatccgtacc gtagtcgatg cgagcgagtc cgatcagtcc aggtttcaaa    120
gtcaaat                                                               127

<210> SEQ ID NO 17
<211> LENGTH: 127
<212> TYPE: DNA
<213> ORGANISM: Artificial Sequence
<220> FEATURE:
<223> OTHER INFORMATION: Synthetic Oligonucleotide

<400> SEQUENCE: 17
atattaatac gactcactat agggagtgca gtcagtccct cggttaaagt ctcgagtcgc      60
tctgtcaaaa tatccgtacc gtagtcgatg cgagcgagtc cgatcagtcc aggtttcaaa    120
gtcaaat                                                               127

<210> SEQ ID NO 18
<211> LENGTH: 127
<212> TYPE: DNA
<213> ORGANISM: Artificial Sequence
<220> FEATURE:
<223> OTHER INFORMATION: Synthetic Oligonucleotide

<400> SEQUENCE: 18
atattaatac gactcactat agggagtgca gtcagtccct cggttaaagt ctcgagtcgc      60
tctgtcaaaa tatccgtacc gtagtcgatg cgagcgagtc cgatcagtcc aggtttcaaa    120
gtcaaat                                                               127

<210> SEQ ID NO 19
<211> LENGTH: 123
<212> TYPE: DNA
<213> ORGANISM: Artificial Sequence
<220> FEATURE:
<223> OTHER INFORMATION: Synthetic Oligonucleotide
```

```
<400> SEQUENCE: 19
tattaatacg actcactata ggggtgcagt cagtccctcg gttaaagtct cgagtcgctc    60
tgtcaaaata tccgtaccgt agtcgatgcg agcgagtccg atcagtccag gtttcaaagt   120
caa                                                                 123

<210> SEQ ID NO 20
<211> LENGTH: 123
<212> TYPE: DNA
<213> ORGANISM: Artificial Sequence
<220> FEATURE:
<223> OTHER INFORMATION: Synthetic Oligonucleotide

<400> SEQUENCE: 20
tattaatacg actcactata ggggtgcagt cagtccctcg gttaaagtct cgagtcgctc    60
tgtcaaaata tccgtaccgt agtcgatgcg agcgagtccg atcagtccag gtttcaaagt   120
caa                                                                 123

<210> SEQ ID NO 21
<211> LENGTH: 123
<212> TYPE: DNA
<213> ORGANISM: Artificial Sequence
<220> FEATURE:
<223> OTHER INFORMATION: Synthetic Oligonucleotide

<400> SEQUENCE: 21
tattaatacg actcactata ggggtgcagt cagtccctcg gttaaagtct cgagtcgctc    60
tgtcaaaata tccgtaccgt agtcgatgcg agcgagtccg atcagtccag gtttcaaagt   120
caa                                                                 123
```

COMPOSITIONS AND METHODS FOR DETECTING, IDENTIFYING AND QUANTITATING MYCOBACTERIAL-SPECIFIC NUCLEIC ACIDS

CROSS-REFERENCE TO RELATED APPLICATIONS

The present invention is a continuation-in-part of U.S. application Ser. No. 12/916,263 filed Oct. 29, 2010, now pending; a continuation-in-part of U.S. application Ser. No. 12/426,890 filed Apr. 20, 2009, which issued as U.S. Pat. No. 8,080,645 on Dec. 20, 2011, which is a continuation-in-part of U.S. application Ser. No. 12/243,949 filed Oct. 1, 2008, which issued as U.S. Pat. No. 8,084,443 on Dec. 27, 2011, which claims priority to U.S. Provisional Application No. 60/976,728 filed Oct. 1, 2007, now expired, all of the proceeding of which are specifically incorporated by reference, and a continuation-in-part of U.S. application Ser. No. 12/510,968 filed Jul. 28, 2009, which issued as U.S. Pat. No. 8,097,419 on Jan. 17, 2012 specifically incorporated by reference, which is a continuation-in-part of U.S. application Ser. No. 11/844,933, filed Aug. 24, 2007, now abandoned, which claims priority to U.S. Provisional Application No. 60/843,711, filed Sep. 12, 2006, now expired.

FIELD OF THE INVENTION

The present invention generally relates to the fields of molecular biology and medical diagnostics. In particular embodiments, compositions and methods are provided for identifying, quantitating, and detecting mycobacterial-specific nucleic acid segments within a population of isolated polynucleotides. In illustrative embodiments, compositions and methods are provided for rapidly and accurately identifying species and strains of the genus *Mycobacterium*, and in particular, strains of *M. tuberculosis*, the causative agent of TB, in biological and environmental samples, clinical specimens, and the like.

BACKGROUND

Mycobacteria are unicellular, aerobic, Gram-positive bacteria. Typically, mycobacteria have a thick hydrophobic cell wall and lack an outer cell membrane. Infections caused by mycobacteria can be active within a host, or latent and asymptomatic. The emergence of multi-drug resistant strains, the need for prolonged antibacterial therapy, and poor patient compliance, has made treatment of mycobacterial infections difficult, particularly in developing nations. The emergence of multidrug resistant (MDR) strains of *M. tuberculosis*, in particular, has made diagnosis and treatment of TB a high priority in developing African populations.

The primary consequence of mycobacterial infection (and particularly, infection by one or more species of *Mycobacterium* genus) in humans is tuberculosis (TB), a contagious infection caused by members of the "*M. tuberculosis* complex," which include, e.g., pathogenic strains of the species *M. tuberculosis, M. bovis, M. africanum, M. microti, M. cannetti, M. caprae* and *M. pinnipedi*. TB typically attacks the lungs in mammalian hosts, but can also spread to other organs and regions of the body including, for example, bone, joints, kidneys, and the abdomen, etc. Members of the *M. tuberculosis* complex are closely related genetically, and possess highly-conserved 16S rRNA sequences across the genus.

TB can be acquired by breathing in air droplets from a cough or sneeze of an infected person. Symptoms of an active tubercular infection can include chronic cough (typically with blood-tinged sputum), fever, nocturnal hyperhidrosis, chronic fatigue, pallor, weight loss, and cachectic wasting ("consumption"). Other symptoms can include breathing difficulties, thoracic pain and wheezing ("Pulmonary Tuberculosis," PubMed Health). If an inhaled tubercle bacillus settles in a lung alveolus, infection occurs, followed by alveolocapillary dilation, and endothelial cell swelling. Alveolitis results with intracellular replication of the tubercle bacilli, and an influx of polymorphonuclear leukocytes to the alveoli. The organisms then spread through the lymph system to the circulatory system, and then throughout the body.

Although *M. tuberculosis* infects less than 200,000 people annually in the United States, according to the World Health Organization (WHO) nearly two billion people worldwide may be infected, 90% of whom can remain asymptomatic for years following infection. Left untreated, TB is fatal in >50% of the infected population, and in disseminated forms of the disease, the mortality rate approaches 90%.

Because of the chronic and debilitating persistence of TB infection, co-infection with one or more secondary pathogens, including in particular, human immunodeficiency virus (HIV), is also widespread. In 2007, there were at least 1.37 million cases of HIV-positive TB, concentrated primarily in emerging populations where diagnosis and treatment are often limited, ineffective, and/or cost-prohibitive.

Conventional diagnosis of a TB infection typically relies on a combination of physical examination (e.g., chronic persistent cough, enlarged or tender lymph nodes, pleural effusion, unusual breath sounds, and, in later stages of the disease, characteristic "clubbing" of the fingers or toes) and diagnostic testing (e.g., sputum examination, microbial culture and nucleic acid testing of specimens, bronchoscopy, CT scan or X-ray of the chest, pulmonary biopsy, thoracentesis, interferon-γ (gamma) blood test, and tuberculin skin test).

The Mantoux tuberculin skin test, or purified protein derivative (PPD) skin test, is performed by intradermally injecting about 0.1 mL of tuberculin PPD into the inner surface of the forearm. Tuberculin PPD is a precipitate of non-species-specific molecules obtained from filtrates of sterilized, concentrated TB cultures. Immune reaction by the patient to PPD is measured within 48 to 72 hours of injection, as millimeters of induration (i.e., a palpable raised hardened area on the skin), which is dependent on the individual's risk factors for acquiring the disease. Both false-positive and false-negative results are fairly common, especially amongst those infected with either non-TB or TB mycobacteria, or a viral illness such as measles or chicken pox, or those previously vaccinated with BCG (Bacille Calmette-Guérin) or live-virus ("Tuberculin Skin Testing for TB," Centers for Disease Control and Prevention).

Acid-fastness is a physical property of some bacterial species that refers to their resistance to decolorization by acids during microscopic staining procedures. In the most common of these procedures, the Ziehl-Neelsen test, the specimen is spread onto a microscope slide, exposed to particular dyes, and then decolorized with a dilute acid or alcohol. Because of the high mycolic acid content of mycobacterial cell walls, these so-called "acid-fast" organisms resist destaining, thus a smear-positive result is presumptively indicative of the presence of tubercle bacilli. Because other non-mycobacterial species may also appear acid-fast in this test, however, sensitivities of less than 50% have been reported when using acid-fastness as an identification criterion. Culture of the specimen and further biochemical testing are therefore required to definitively confirm the presence of TB.

Both the tuberculin skin test and the smear tests are used as screening methods and are not usually determinative of a TB infection, therefore even those individuals with smear-negative results can be further tested for TB, depending upon the individual's risk factors and availability of testing. *M. tuberculosis* detection using the GeneXpert® (Cepheid, Calif., USA) platform has been widely implemented throughout Africa and appears to detect a high percentage of smear-negative cases. However, this also has limitations that include reduced sensitivity compared to other nucleic acid approaches, increased platform and testing costs and constraints for use in remote and point of care settings.

The "standard" of TB diagnostics, cell culturing of mycobacterial organisms, is difficult, due in part to their long generation times, i.e., twenty-four hours for *M. tuberculosis*. In addition, mycobacteria are typically present at low levels in infected individuals. Culturing from a clinical specimen can therefore take anywhere between four to eight weeks, during which time a patient may become seriously ill and contagious to others. In addition, cell culturing requires the collection, transport and maintenance of viable mycobacterial organisms in a sample until such time as the sample can be analyzed in a lab setting. In countries where TB is prevalent, and health care is minimal, this may not be an option, thus increasing the risk of spreading infection.

Interferon-γ tests, such as QuantiFERON® TB Gold (Cellestis Limited, Victoria, Australia), measure the amount of the cytokine, interferon-γ (IFN-γ) (a component of cell-mediated immune reactivity to the *M. tuberculosis* complex) and can detect both latent and active tuberculosis infections. Heparinized whole blood obtained from a person suspected of TB infection is incubated for 16-24 hours with ESAT-6 and CFP-10, two synthetic proteins derived from *M. tuberculosis*, and control antigens. The level of IFN-γ produced by the lymphocytes upon recognizing the synthetic proteins is measured, and results are unaffected by previous BCG vaccination or cross-reactivity with other mycobacteria. Results of the IFN-γ test can be later confirmed by standard culture methods, if necessary. Unfortunately for regions with limited access to medical care, the whole blood must be analyzed within 12 hours of obtaining the sample, and the effectiveness of the test has not been analyzed on patients with other medical conditions such as HIV, AIDS, diabetes, silicosis, chronic renal failure, hematological disorders, individuals that have been treated for TB infection, nor has it been tested on pregnant individuals or minors ("Clinicians Guide to QuantiFERON®-TB Gold," Cellestis). Other non-culture methods such as radioimmunoassays, latex agglutination, and enzyme-linked immunosorbent assays (ELISAs) have been used with limited degrees of success to confirm the presence of tubercle bacilli in biological samples.

Nucleic acid amplification testing for TB includes the use of standard polymerase chain reaction (PCR) techniques to detect mycobacterial DNA in patient specimens, nucleic acid probes to identify mycobacteria in culture, restriction fragment length polymorphism (RFLP) analysis to compare different strains of TB for epidemiological studies, and genetic-based susceptibility testing to identify drug-resistant strains of mycobacteria. The complete genome of *M. tuberculosis* has been sequenced and published; currently two nucleic acid amplification-based tests for TB have been approved for use in the United States by the Food and Drug Administration (FDA). The first, known as the "Enhanced Amplified *Mycobacterium Tuberculosis* Direct Test" (E-MTD, Gen-Probe, San Diego, Calif., USA), is approved for detection of *M. tuberculosis* complex bacteria in acid-fast bacilli in both smear-positive and smear-negative respiratory specimens from patients suspected of having TB. The E-MTD test combines isothermal transcription-mediated amplification of a portion of the 16S rRNA with a detection method that uses a hybridization probe specific for *M. tuberculosis* complex bacteria. The second, known as the AMPLICOR® *Mycobacterium tuberculosis* Test (AMPLICOR®, Roche Diagnostics, Basel, Switzerland), has been approved for the detection of *M. tuberculosis* complex bacteria only in smear-positive respiratory specimens from patients suspected of having TB. This test uses PCR to amplify a portion of the 16S rRNA gene that contains a sequence that hybridizes with an oligonucleotide probe specific for *M. tuberculosis* complex bacteria. ("Report of an Expert Consultation on the Uses of Nucleic Acid Amplification Tests for the Diagnosis of Tuberculosis," Centers for Disease Control and Prevention).

Results have indicated that the sensitivity and specificity of these tests tends to vary depending on geographical location and risk factors. In addition, these techniques require complex laboratory conditions and equipment to be performed, thus reducing the speed and sensitivity of the test. For these and other reasons, there remains a need in the art for reliable and accurate methods for detection of Mycobacterial pathogens in clinical samples, and in particular, methods for rapidly identifying such pathogens in field applications, remote locations, and in developing countries where conventional laboratories are lacking, and financial resources are limited. In particular, compositions for the safe collection, handling, and transport of pathogenic specimens, as well as molecular biology-based methods for the rapid detection and accurate identification of TB-specific nucleic acids in such specimens are highly desired.

BRIEF SUMMARY OF THE INVENTION

The present invention overcomes these and other inherent limitations in the prior art by providing useful, non-obvious, and novel compositions to safely collect, handle and transport biological samples suspected of containing pathogenic organisms, as well as methods for rapidly detecting, identifying and quantitating those pathogens through molecular biology-based nucleic acid testing. In particular, methods are provided for specifically detecting one or more strains of pathogenic bacteria from the *M. tuberculosis* complex to aid in the diagnosis of TB. In particular applications, the invention encompasses a diagnostic product that permits the collection of a target specimen, preparation of the target specimen for assaying, isolation of genomic material from the specimen, and subsequent processing of the genomic material to identify one or more organisms, if present, in the biological sample. When coupled with one or more specimen collection devices, the compositions disclosed herein permit safe, collection, transport and storage of biological specimens, even for those collected in remote or "field" applications, wherein the time from sample collection to sample assay may be hours to days, or even weeks.

The invention further encompasses compositions and methods that simplify and expedite specimen collection, preparation and molecular detection of microorganisms, specifically those in the *M. tuberculosis* complex. In particular applications, the invention encompasses a diagnostic product whereby the specimen is collected, transported and rapidly prepared for downstream PCR without the need for a cold chain or costly and time-consuming sample decontamination and specimen emulsification. The molecular diagnostic product includes a thermo-stabile, all-inclusive PCR mixture of primers, probes and enzymes in a ready-to-use solution or suspension. This diagnostic product can be used in central labs and with high through-put systems or in rural or mobile clinics with minimal capabilities and in the absence of reliable community electric power, or even with a hand-held device. The invention also encompasses a method for epidemiologic and outbreak surveillance, pandemic and epidemic tracking and microbial sequencing directly from field samples at the site of collection or by using inexpensive, simplified, safe shipping through standard mail at ambient temperature. This invention also encompasses a diagnostic molecular detection kit for safe site of care collection, rapid extraction and rapid PCR detection of microbes, specifically members of the *M. tuberculosis* complex.

Using the TB-specific nucleic acid detection probes and amplification primers disclosed herein, the present invention also provides facile identification of mycobacteria in collected samples, and permits a safe, cost-effective, and near-term assessment of TB infection, including, for example, as a tool in surveillance against potential epidemics, monitoring of TB outbreaks, assessment of TB disease progression in affected or at-risk populations, and/or identification of particular species and/or strains of the *M. tuberculosis* complex for diagnostic testing or determining particular therapeutic modalities.

In one embodiment, the invention provides a method for obtaining a population of mycobacterial-specific polynucleotides from a sample suspected of containing one or more pathogenic mycobacterial cells. In an overall sense, this method generally involves contacting a sample suspected of containing one or more pathogenic mycobacterial cells for an effective amount of time and with a sufficient amount of a composition that includes: a) one or more chaotropes; b) one or more detergents; c) one or more reducing agents; d) one or more chelators; and e) one or more surfactants, to kill substantially all, and preferably to kill all of the pathogenic organisms therein, including, for example, pathogenic bacteria, fungi, viruses, and in particular mycobacterial cells (if present in the sample). In the practice of the method, substantially all (and preferably, all) of the cells and microorganisms contained therein are lysed, and their cellular contents liberated into the solution. Preferably, substantially all (and more preferably, all) of the cellular enzymes, proteins, peptides, lipoproteins, and other cellular contents are denatured and/or inactivated, including any exogenous or endogenous nucleases that may be present in the sample, such that the resulting mixture is rendered substantially safe (and preferably, safe) for handling, storage, and/or transport by workers without undue effects, and without the need for concern over pathogenicity, toxicity, or danger of handling the sample now that it has been decontaminated and any pathogenic organisms originally present therein, destroyed, inactivated, killed, and/or lysed to render them harmless.

Preferably the population of polynucleotides so obtained from the method will preferably be substantially stable, such that the nucleic acids do not substantially degrade, and the integrity of the obtained population of polynucleotides will preferably be at least substantially maintained, so that the obtained polynucleotides are substantially intact, and present in the sample in the form that they were in when the cells containing them were initially liberated/lysed by the action of the components present in the composition. As noted herein, in preferred applications of the invention, the population of mycobacterial-specific polynucleotides obtained using the disclosed methods are substantially stable and non-degraded such that they can be maintained for significant periods of time even at less-than-ideal ambient temperatures (e.g., at a temperature of about 0° C. to even about 40° C. or more) for extended periods of time (e.g., for periods of several hours to several days to several week or months even) without significantly degrading the liberated nucleic acids, thereby making them suitable for downstream molecular analysis (e.g., template-dependent amplification reactions et al.) days to weeks after extraction of the nucleic acids takes place, even when it is not possible to store the populations of polynucleotides extracted from the samples frozen, on ice, or refrigerated between initial sample collection and subsequent molecular analysis.

As noted herein, in preferred embodiments, the (i) the one or more chaotropes preferably include guanidine thiocyanate, guanidine isocyanate, guanidine hydrochloride, or any combination thereof; (ii) the one or more detergents preferably include sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, or any combination thereof; (iii) the one or more reducing agents preferably include 2-mercaptoethanol, tris(2-carboxyethyl)phosphine, dithiothreitol, dimethylsulfoxide, or any combination thereof; (iv) the one or more chelators preferably include ethylene glycol tetraacetic acid, hydroxyethylethylenediaminetriacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, or any combination thereof; or (v) the one or more buffers preferably include tris(hydroxymethyl)aminomethane, citrate, 2-(N-morpholino)ethanesulfonic acid, N,N-Bis(2-hydroxyethyl)-2-aminoethanesulfonic acid, 1,3-bis(tris(hydroxymethyl) methyl amino)propane, 4-(2-hydroxyethyl)-1-piperazine ethanesulfonic acid, 3-(N-morpholino)propanesulfonic acid, bicarbonate, phosphate, or any combination thereof.

In particular illustrative embodiments, the inventors have prepared formulations that preferably include: (a)(i) about 3 M guanidine thiocyanate; (ii) about 1 mM TCEP; (iii) about 10 mM sodium citrate; (iv) about 0.5% N-lauroyl sarcosine; (v) about 0.0002% silicone polymer; (vi) about 100 mM 2-amino-2-hydroxymethyl-propane-1,3-diol (TRIS); and (vii) about 0.1 mM EDTA; or (b) (i) about 3 M guanidine thiocyanate; (ii) 1 mM TCEP; about 10 mM sodium citrate; (iii) about 0.5% N-lauroyl sarcosine, sodium salt; (iv) about 0.0002% of a silicone polymer; (v) about 100 mM TRIS; (vi) about 0.1 mM EDTA; and (vii) about 10% to about 25% ethanol (vol./vol.).

Because of the remarkable effectiveness of the disclosed formulations in readily killing, and lysing the cells, denaturing the proteinaceous cellular components and inactivating enzymes such as endogenous and exogenous nucleases that are deleterious to the preservation of intact nucleic acids, the inventors have demonstrated that in certain instances, substantially all of the microorganisms present in a sample are killed and/or lysed within the first few minutes it is contacted with the composition. In some instances, the killing and lysing of the cells is substantially complete within about 3 or about 4 or about 5 or so minutes of contacting the sample with the composition. Likewise, in other instances, contacting the sample with the composition for a period of about 6, or about 7, or about 8, or about 9, or about 10 minutes or so is sufficient to substantially kill and/or lyse all of the pathogens that may be present in the collected sample.

Likewise, the inventors have demonstrated that in certain instances, substantially all of the proteins, enzymes, nucleases, and the like liberated from the lysed cells present in a sample are substantially all inactivated and/or denatured within only a few minutes of contacting the sample with the composition.

Preferably the samples will be of biological, clinical, veterinary, or environmental origin, and in certain embodiments, the samples are preferably of human origin, and in particular, from humans that have, are suspected of having, or are at risk for developing a microbial infection, such as a tubercular infection caused by one or more strains or species of the genus *Mycobacterium*.

In certain instances, the individuals from which the samples are taken may be patients that also have, are suspected of having, or are at risk for developing one or more secondary or tertiary medical conditions, and in particular, a secondary and/or tertiary infection by one or more non-*Mycobacterium* species of bacteria, or one or more pathogenic species of fungal or viral origin, or any combination thereof.

Preferably the population of nucleic acid segments contained with the plurality of isolated and purified polynucleotides obtained from a sample will be suitable for primer-dependent amplification, and particularly so, when the polynucleotides are stored in the composition for a period of about 1 to about 90 days between the time of sample collection and molecular analysis, even when stored at less-than-ideal storage conditions, including, for example, storage under ambient temperature of about 0° C. to about 40° C.

In some embodiments, the method further includes the step of detecting within the obtained population of mycobacterial-specific polynucleotides the presence of at least a first *Mycobacterium*-specific nucleic acid segment by contacting the population with a labeled oligonucleotide detection probe, wherein the presence of a labeled hybridization product is indicative of the presence of one or more *Mycobacterium*-specific nucleic acid segments in the obtained population of polynucleotides.

In exemplary embodiments, the labeled oligonucleotide detection probe includes at least a first sequence region that consists of the sequence of SEQ ID NO:4 or SEQ ID NO:7.

In further embodiments, the composition may further initially include a known quantity of at least a first internal positive control nucleic acid segment of about 50 to about 500, alternatively, about 70 to about 250, or alternatively still, about 90 to about 150 nucleotides in length, wherein the internal positive control nucleic acid segment does not substantially hybridize to genomic nucleic acids of the host from which the sample was obtained, nor to genomic nucleic acids of a mycobacterial pathogen. Such IPCs are disclosed herein in detail, and may include a single-stranded DNA, a double-stranded DNA, a single-stranded RNA, a double-stranded RNA, or a double-stranded DNA:RNA hybrid. In certain embodiments, the IPC nucleic acid segment includes an at least 40-contiguous nucleotide sequence, an at least 50-contiguous nucleotide sequence, an at least 60-contiguous nucleotide sequence, an at least 70-contiguous nucleotide sequence, or an at least 80-contiguous nucleotide sequence from SEQ ID NO:8, or the complement thereof.

In exemplary embodiments, the IPC includes (a) a first sequence domain that specifically binds to a labeled oligonucleotide detection probe of from about 15 to about 40 nucleotides in length, from about 18 to about 35 nucleotides in length, or from about 20 to about 30 nucleotides in length, that is specific for the first internal positive control nucleic acid segment; (b) a second sequence domain that specifically binds to a forward PCR amplification primer of about 15 to about 45 nucleotides in length, about 25 to about 35 nucleotides in length, or about 20 to about 30 nucleotides in length; and (c) a third sequence domain that specifically binds to a reverse PCR amplification primer of about 15 to about 45 nucleotides in length, about 18 to about 40 nucleotides in length, about 21 to about 35 nucleotides in length, or about 24 to about 30 nucleotides in length, wherein the second and third sequence domains are operably positioned upstream, and downstream, respectively, of the first sequence domain to facilitate a PCR-directed amplification of at least a first portion of the internal positive control nucleic acid segment from the forward and reverse primers under conditions effective to amplify the at least a first portion.

In certain aspects, the invention may further employ the use of an extraction apparatus, or an automated high-throughput system, including, for example, portable, bench-top, and/or handheld extraction devices that include, without limitation, (a) a filtration vessel that has at least one receiving end and that comprises a membrane filter adapted to bind the population of polynucleotides thereto, wherein the membrane filter is disposed at least substantially across a width of the filtration vessel and at least partially therein; and (b) a volume-dispensing mechanism adapted to controllably dispense and forcibly inject an amount of liquid operably associated with the filtration vessel to filter the liquid therethrough.

The method may also preferably further include at least the steps of (a) performing at least one thermal cycling step, wherein the cycling comprises at least a first amplifying step and at least a first hybridizing step, wherein the at least a first amplifying step comprises contacting the obtained population of polynucleotides with a composition that comprises at least a pair of distinct, independently-selected, *Mycobacterium*-specific amplification primers, a thermostable polymerase, a first osmolarity agent comprising betaine, at least a first reference dye, and a plurality of deoxynucleoside triphosphates to produce at least a first *Mycobacterium*-specific amplification product; and (b) detecting the presence of the amplification product so produced by contacting it with a first labeled *Mycobacterium*-specific oligonucleotide detection probe, wherein the presence of a labeled hybridization product is indicative of the presence of one or more *Mycobacterium*-specific nucleic acid segments in the obtained population of polynucleotides. In such embodiments, the pair of distinct, independently-selected, *Mycobacterium*-specific amplification primers may preferably include a first oligonucleotide primer of 18 to about 30 nucleotides in length, and a second oligonucleotide primer of 18 to about 30 nucleotides in length, wherein each of the first and second primers specifically hybridize to a first, and a second distinct sequence region, respectively, within the sequence of 5'-SEQ ID NO:1, or the complement thereof.

In related embodiments, the method of the present invention may further optionally include the step of performing a primer-dependent amplification of at least a first sequence region of the internal positive control nucleic acid segment in the obtained population of polynucleotides, and quantitating the amount of the internal positive control nucleic acid segment present in the obtained population of polynucleotides.

Likewise, the method may further optionally include the step of comparing the amount of the internal positive control nucleic acid segment present in the composition at one or more steps along the analytical process, to the amount of IPC that was present in the original composition before the sample was initially added to the lysis/storage/transport medium, or to the amount of target nucleic acids that were present in the original composition. Such comparison may serve to demonstrate that the amount of IPC still contained in the sample in a downstream point of assay is comparable to, or substantially the same as, the known amount of IPC that was present in the MTM composition before the sample was added to it, and may serve to quantitate the amount of target nucleic acids of interest in the collected samples, or downstream assayed components. Such information may also be indicative of the amount of the nucleic acids remaining in the sample as compared to what was originally present, and may provide an estimate of the degree of sample degradation of the polynucleotides originally present over time.

In some applications of the present technology, the primer-dependent amplification of the least a first sequence region of the internal positive control nucleic acid segment is performed subsequent to the amplification of the *Mycobacterium*-specific nucleic acid segment, while in other aspects, the primer-dependent amplification of the least a first sequence region of the internal positive control nucleic acid segment is performed substantially simultaneously with the amplification of the *Mycobacterium*-specific nucleic acid segment.

The amplification product of the internal positive control nucleic acid segment may be detected with a suitable oligonucleotide detection probe comprising a first detectable label, and the amplification product of the *Mycobacterium*-specific nucleic acid segment is detected with an oligonucleotide detection probe comprising a second distinct detectable label.

Such primer-dependent amplification of at least a first sequence region of the internal positive control nucleic acid segment may preferably be performed in accordance with the invention using (a) a forward amplification primer that comprises a sequence region that consists essentially of the sequence of SEQ ID NO:9 (5'-GTGCAGTCAGTCCCTCG-GTTA-3'), or the complement thereof; (b) a reverse amplification primer that comprises a sequence region that consists essentially of the sequence of SEQ ID NO:10 (5'-TTGACTTTGAAACCTGGACTGATC-3') or the complement thereof; and (c) a labeled oligonucleotide detection probe that comprises a sequence region that consists essentially of the sequence of SEQ ID NO:11 (AAATATCCGTAC-CGTAGTCG), or the complement thereof.

Such method may also further optionally include detecting the presence of one or more drug resistance genes within the population of obtained polynucleotides.

The invention further provides a method for detecting the presence of a *Mycobacterium*-specific nucleic acid segment in a population of polynucleotides obtained from a sample. In an overall sense, the method generally includes (a) performing at least one thermal cycling step, wherein the cycling comprises at least a first amplifying step and at least a first hybridizing step, wherein the at least a first amplifying step comprises contacting a population of polynucleotides obtained from a sample suspected of containing a *Mycobacterium*-specific nucleic acid segment with a composition that comprises at least a pair of distinct, independently-selected, *Mycobacterium*-specific amplification primers, a polymerase, a first osmolarity agent comprising betaine, (optionally at least a first reference dye, such as ROX), and a plurality of deoxynucleoside triphosphates to produce a *Mycobacterium*-specific amplification product when a *Mycobacterium*-specific nucleic acid segment is present in the sample; and (b) detecting the presence of the amplification product by contacting the amplification product with a labeled *Mycobacterium*-specific oligonucleotide detection probe, wherein the presence of a labeled hybridization product is indicative of the presence of one or more *Mycobacterium*-specific nucleic acid segments in the population of polynucleotides, wherein the pair of distinct, independently-selected, *Mycobacterium*-specific amplification primers comprises a first oligonucleotide primer of 18 to about 30 nucleotides in length, and a second oligonucleotide primer of 18 to about 30 nucleotides in length, wherein each of the first and second primers specifically hybridize to a first, and a second distinct sequence region, respectively, within the sequence of SEQ ID NO:1, or the complement thereof.

In illustrative embodiments, (a) at least one of the pair of amplification primers preferably includes: (i) a first oligonucleotide primer of 18 to about 30 nucleotides in length that preferably includes at least a first sequence region consisting of a sequence that is at least 90% identical to the nucleic acid sequence of 5'-CTCGTCCAGCGCCGCTTC-3' (SEQ ID NO:2), or 5'-ACCAGCACCTAACCGGCT-3' (SEQ ID NO:5), or the complement thereof; or (ii) a second oligonucleotide primer of 18 to about 30 nucleotides in length that preferably includes at least a second sequence region consisting of a sequence that is at least 90% identical to the nucleic acid sequence of 5'-TCGCCTACGTGGCCTTTGT-3' (SEQ ID NO:3), or 5'-ACCGACGCCTACGTCGCA-3' (SEQ ID NO:6), or the complement thereof; and (b) a *Mycobacterium*-specific oligonucleotide detection probe of 24 to about 35 nucleotides in length that preferably includes at least a third sequence region consisting of a sequence that is at least 90% identical to the nucleic acid sequence of 5'-ACCAGCAC-CTAACCGGCTGTGGGTA-3' (SEQ ID NO:4), or 5'-AGGGTTCGCCTACGTGGCCTTTGT-3' (SEQ ID NO:7), or the complement thereof. Preferably, such a method is compatible with at least one high throughput polymerase chain reaction technology, and may further optionally include determining the nucleic acid sequence of all or part of the detected *Mycobacterium*-specific nucleic acid segments using one or more conventional sequence analysis methodologies that are known to those of ordinary skill in the molecular biological arts.

The invention also provides a primer-dependent amplification reaction-compatible composition that preferably includes (a) one or more buffers; (b) one or more osmolarity agents; (c) one or more chelators; (d) one or more salts; (e) at least a pair of distinct, independently-selected, *Mycobacterium*-specific amplification primers, wherein each of the first and second primers specifically hybridize to a first, and a second distinct sequence region, respectively, within the sequence of SEQ ID NO:1, or the complement thereof; (f) a *Mycobacterium*-specific oligonucleotide detection probe comprising a first detectable label, that specifically hybridizes to a third sequence region within the sequence of SEQ ID NO:1, or the complement thereof; (g) at least one primer-dependent amplification reaction-capable thermostable polymerase; and (h) a plurality of deoxynucleoside triphosphates, each present in an amount sufficient to enable the amplification of at least a first *Mycobacterium*-specific amplification product.

In illustrative embodiments, (a) the one or more buffers preferably include tris(hydroxymethyl)aminomethane (TRIS); (b) the one or more polymerase chain reaction osmolarity agents preferably include N,N,N-trimethylglycine (betaine), dimethyl sulfoxide (DMSO), foramide, glycerol, nonionic detergents, bovine serum albumin (BSA), polyethylene glycol, tetramethylammonium chloride, or any combination thereof; (c) the one or more chelators preferably include ethylene glycol tetraacetic acid, hydroxyethylethylenediaminetriacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, or any combination thereof; and (d) the one or more salts preferably include potassium chloride, magnesium sulfate, potassium glutamate, or any combination thereof, and the pair of primers preferably includes: (i) a first oligonucleotide primer of 18 to about 30 nucleotides in length that preferably includes at least a first sequence region that consists of a sequence that is at least 95% identical to the nucleic acid sequence of SEQ ID NO:2, or SEQ ID NO:5, or a complement thereof; and (ii) a second oligonucleotide primer of 18 to about 30 nucleotides in length that preferably includes at least a first sequence region that consists of a sequence that is at least about 90% identical, preferably at least about 95% identical to, and more preferably, at least about 98% identical the nucleic acid sequence of SEQ ID NO:3, or SEQ ID NO:6, or a complement thereof.

The *Mycobacterium*-specific oligonucleotide detection probe preferably is from 24 to about 35 nucleotides in length, and more preferably includes at least a first sequence region that consists of a sequence that is at least 85% identical, at least 90% identical, at least 95% identical, or at least 98% or greater identical to at least a first contiguous nucleic acid sequence from SEQ ID NO:4, or SEQ ID NO:7, or a complement thereof. The composition may further optionally include one or more internal reference dyes compatible with a polymerase chain reaction, such as those that include one or more fluorophores, one or more quenchers, one or more reporter molecules, one or more nucleic acid intercalating agents, or any combination thereof.

In illustrative embodiments, the composition preferably includes (a) about 50 mM of TRIS; (b) about 70 mM of potassium chloride; (c) about 3 mM of magnesium sulfate; (d) about 45 mM betaine; (e) about 0.03 µg/mL of bovine serum albumin; (f) about 0.1 mM of EDTA; (g) about 0.01 µM to about 1 µM of dye; (h) about 4 µM of a first oligonucleotide primer of 18 to about 30 nucleotides in length that comprises at least a first sequence region consisting essentially of the nucleic acid sequence of SEQ ID NO:2, or SEQ ID NO:5, or the complement thereof; (i) about 4 µM of a second oligonucleotide primer of 18 to about 30 nucleotides in length that comprises at least a second sequence region consisting essentially of the nucleic acid sequence of SEQ ID NO:3, or SEQ ID NO:6, or the complement thereof; (j) about 6 µM of a *Mycobacterium*-specific oligonucleotide detection probe of 24 to about 35 nucleotides in length that comprises at least a third sequence region consisting essentially of a nucleic acid sequence of SEQ ID NO:4, or SEQ ID NO:7, or the complement thereof; (k) about 1 unit of Taq polymerase; and (l) about 0.2 mM of deoxynucleoside triphosphates.

The detectable label may preferably include one or more radioactive labels, one or more luminescent labels, one or more chemiluminescent labels, one or more fluorescent labels, one or more phosphorescent labels, one or more magnetic labels, one or more spin-resonance labels, one or more enzymatic labels, or any combination thereof. Exemplary detectable labels include, without limitation, fluorescein, 6-carboxyfluorescein (6-FAM), 6-carboxyfluorescein-N-succinimidyl ester (6-FAMSE), a VIC dye, or any combination thereof.

As noted herein, the invention also provides diagnostic kits that preferably include one or more of the compositions disclosed herein, and instructions for using the kit in the detection of a *Mycobacterium*-specific nucleic acid segment in an aqueous sample; optionally the kit may further include (typically in a separate, distinct container), a first MTM composition that comprises: a) one or more chaotropes; b) one or more detergents; c) one or more reducing agents; d) one or more chelators; and e) one or more surfactants, each present in an amount to substantially kill or lyse one or more pathogenic mycobacterial cells, or to denature or inactivate one or more proteins, enzymes, or nucleases liberated therefrom when placed in the composition for an effective amount of time. In certain embodiments, the kit may also further include (preferably within the MTM composition) a known quantity of at least a first internal positive control nucleic acid segment (and preferably one of from about 50 to about 500 nucleotides in length), wherein the internal positive control nucleic acid segment does not substantially hybridize (and preferably, does not specifically hybridize) to the genomic nucleic acids of the host from which the sample was obtained, nor to genomic nucleic acids of the one or more microbiological pathogens suspected within the sample. As noted herein, such kits may also further optionally include one or more extraction apparatuses for isolating and purifying the population of polynucleotides from the lysed/liberated/denatured sample contacted with the MTM formulation. Such an extraction apparatus may be a portable, bench-top, or even a handheld device that preferably includes: (i) a filtration vessel that has at least one receiving end and that comprises a membrane filter adapted to bind the population of polynucleotides thereto, wherein the membrane filter is disposed at least substantially across a width of the filtration vessel and at least partially therein; and (ii) a volume-dispensing mechanism adapted to controllably dispense and forcibly inject an amount of liquid operably associated with the filtration vessel to filter the liquid therethrough; and b) instructions for using the extraction apparatus to obtain the population of purified polynucleotides from an aqueous sample suspected of comprising at least a first mycobacterial pathogen.

The invention also provides a method for obtaining a primer-dependent amplification reaction-compatible population of mycobacterial-specific nucleic acid segments from an aqueous sample suspected of containing a plurality of pathogenic mycobacterial cells. Such a method generally includes (a) contacting the aqueous sample with an amount of a composition comprising: (i) one or more chaotropes; (ii) one or more detergents; (iii) one or more reducing agents; (iv) one or more chelators; and (v) one or more surfactants, for a time effective to lyse substantially all of the population of pathogenic mycobacterial cells, to substantially denature all of the proteins liberated therefrom, and substantially inactivate all of the endogenous and exogenous nucleases present therein; and subsequently (b) isolating therefrom a purified population of primer-dependent amplification reaction-compatible mycobacterial-specific nucleic acid segments, that remains substantially stable, and substantially non-degraded, when the aqueous sample is contacted with the composition substantially for a period of about 1 to about 60 days, at an ambient temperature substantially of from about 0° C. to about 40° C.

The present invention advantageously improves conventional specimen collection, ensures lysis of any microbial pathogens contained therein, and facilitates safe and effective transport and storage of such samples from the point of collection to the point of identification and assay. Moreover, the molecular transport media compositions disclosed herein facilitate stabilization of nucleic acids liberated from the collected microorganisms, as well as maintain the fidelity and preserve the integrity of the liberated nucleic acids for extended periods of time, even under ambient, or less-than-ideal storage conditions.

Accordingly, the present invention advantageously provides a collection and preservation formulation that lyses biological pathogens, stabilizes the liberated nucleic acids (both RNAs and DNAs), and preferably at least substantially maintains, and preferably entirely maintains, the integrity of the collected polynucleotides such that at least a first portion of which is readily available, and ideally suited for downstream molecular diagnostic analysis of the nucleic acids contained within the collected specimen.

The "one-step" isolation/storage/transport formulations disclosed herein advantageously accomplish at least one or more, and preferably, all of, the following principal functions: inactivation or killing of pathogens within the sample; lysis of cells and release of nucleic acids from within the cells; inactivation of cellular enzymes, including endogenous and exogenous nucleases, to prevent degradation of the liberated nucleic acids; facilitation of facile collection and safe handling/transport of the sample of isolated polynucleotides at ambient temperatures for extended periods of time without the need for refrigeration or conventional sub-zero storage temperatures; effective stabilization of the nucleic acids during subsequent handling, transport and/or storage of the sample; and preservation and/or maintenance of the integrity of at least a first portion of the population of polynucleotides contained therein for a time sufficient to permit molecular characterization and identification of at least a first nucleic acid segment contained therein.

In particular aspects as described herein, and particularly when performing the method for the analysis of specimens that are acquired in either remote or "field" sites, the molecular transport medium (MTM) compositions of the present invention preferably stabilize the collected biological sample for at least a period of time sufficient to facilitate subsequent molecular analysis, without substantial degradation or loss of at least a first population of nucleic acids obtained from the collected sample. Preferably, the MTM compositions herein facilitate collection/transport/storage of the biological specimens collected therein for extended periods of time (from a few hours to a few days, or even a few weeks or months or more) at ambient environmental temperatures, such that the collected samples do not require refrigeration and/or freezing in order to preserve them for subsequent molecular testing. More preferably still, the MTM formulations disclosed herein stabilize and preserve the collected nucleic acids in sufficient fashion to permit subsequent amplification and identification of at least a first nucleic acid sequence from at least a first microbial pathogen present in the collected sample.

In illustrative embodiments, the MTM formulations described herein further optionally include at least a first internal positive control (IPC) to facilitate improved recovery of the microbial-specific polynucleotides, and to permit determination of sequence fidelity and preservation of the collected specimen. Exemplary known polynucleotide sequences may be present in the collection reagent at the time of specimen collection, and the subsequent analysis of this known quantity of IPC may be used to accurately monitor the fidelity of the population of polynucleotides throughout the collection/transport/analysis phases of the described identification methods.

In the practice of the invention, exemplary pathogens to be identified using the transport media disclosed herein include, but are not limited to, one or more mycobacteria, including, without limitation, one or more species or strains of the genus *Mycobacterium*, including one or more causal agents of tuberculosis. Preferably, a first population of polynucleotides is obtained from a biological or environmental sample suspected of containing such pathogens, generally by contacting the biological sample with an amount of a MTM composition that includes a) at least one or more chaotropes; b) at least one or more detergents; c) at least one or more reducing agents; d) at least one or more chelators; and e) at least one or more surfactants, each present in an amount sufficient to denature one or more proteins present in the sample, inactivate one or more nucleases present in the sample, kill, neutralize, and/or lyse substantially all of the microbial pathogens present in the sample, and substantially inhibit or prevent the activity of endogenous or exogenous nucleases from degrading the population of nucleic acids liberated from the organism(s) present in the sample.

Particular compositions and methods of use can be found in Applicant's co-pending U.S. Patent Appl. Publ. No. 2009/0312285 (filed Oct. 1, 2008), the contents of which is expressly incorporated herein in its entirety by express reference thereto. In illustrative embodiments, the one or more chaotropes preferably include guanidine thiocyanate, guanidine isocyanate, guanidine hydrochloride, or any combination thereof; the one or more detergents preferably include sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, or any combination thereof; the one or more reducing agents preferably include 2-mercaptoethanol, tris(2-carboxyethyl)phosphine, dithiothreitol, dimethylsulfoxide, or any combination thereof; the one or more chelators preferably include ethylene glycol tetraacetic acid, hydroxyethylethylenediaminetriacetic acid, diethylene triamine pentaacetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, or any combination thereof; or the one or more buffers preferably include tris(hydroxymethyl)aminomethane, citrate, 2-(N-morpholino)ethanesulfonic acid, N,N-Bis(2-hydroxyethyl)-2-aminoethanesulfonic acid, 1,3-bis(tris(hydroxymethyl)methyl amino)propane, 4-(2-hydroxyethyl)-1-piperazine ethanesulfonic acid, 3-(N-morpholino)propanesulfonic acid, bicarbonate, phosphate, or any combination thereof.

In yet other embodiments, the integrity of the population of polynucleotides is at least substantially maintained, and the population of polynucleotides remains substantially non-degraded, when the population of polynucleotides is stored at a temperature of about 10° C. to about 40° C. for a period of about 1 to about 30 days prior to the step of thermal cycling in the composition that includes (a)(i) about 3 M guanidine thiocyanate; (ii) about 1 mM TCEP; (iii) about 10 mM sodium ciliate; (iv) about 0.5% N-lauroyl sarcosine; (v) about 0.0002% silicone polymer; (vi) about 100 mM 2-amino-2-hydroxymethyl-propane-1,3-diol (TRIS); and (vii) about 0.1 mM EDTA; or (b) (i) about 3 M guanidine thiocyanate; (ii) 1 mM TCEP; about 10 mM sodium citrate; (iii) about 0.5% N-lauroyl sarcosine, sodium salt; (iv) about 0.0002% of a silicone polymer; (v) about 100 mM TRIS; (vi) about 0.1 mM EDTA; and (vii) about 10% to about 25% ethanol (vol./vol.). In some embodiments, the integrity of the population of polynucleotides is at least substantially maintained, and the population of polynucleotides remains substantially non-degraded, when the composition containing the population of polynucleotides is stored at a temperature of from about 10° C. to about 40° C. for a period of from about 1 to about 7 days or from a period from about 7 days to about 14 days, or 14 days to about 28 days.

In particular embodiments, the integrity of the polynucleotides within the population is substantially maintained such that at least about 75%, or at least about 80%, at least about 85% or at least about 90%, at least about 95%, at least about 98% and in some instances at least about 99%, of the initial polynucleotides remain at least substantially full-length upon storage of the composition at a temperature of about 10° C. to about 40° C. for a period of about 1 to about 30 days, and, in some embodiments for a period about 1 to 14 days.

In the practice of the invention, the population of polynucleotides so analyzed will preferably be obtained from a biological sample, with biological samples obtained from a mammal (including e.g., humans, non-human primates, domesticated livestock, and the like). Samples may be obtained at any suitable time prior to the amplification protocol, and subsequent detection of amplification products, but in particular aspects, the time between sample collection, isolation of a population of polynucleotides from the sample, and the amplification/detection analysis of the target nucleic acids of interest is quite short, such as, on the order of minutes to hours from specimen collection to amplification product detection, while in other embodiments, the amplification/detection analysis of the target nucleic acids of interest may be longer.

In one embodiment, a method of collecting a biological sample suspected of containing at least a first population of polynucleotides isolated from a member of the genus *Mycobacterium* includes: placing the biological sample in a first collection device that contains at least a first solution comprising a) one or more chaotropes; b) one or more detergents; c) one or more reducing agents; d) one or more chelators; and e) one or more surfactants, each present in an amount sufficient to denature one or more proteins, or inactivate one or more nucleases; wherein the collection solution kills, inactivates or decontaminates any members of *Mycobacterium tuberculosis* complex that are present in the specimen for safe handling and transport; and wherein the integrity of the population of polynucleotides is at least substantially maintained and the population of polynucleotides remains substantially non-degraded when the collection solution containing the population of polynucleotides is stored at a temperature of about 10° C. to about 40° C. for a period of about 1 to about 42 days prior to extracting the population of polynucleotides from the collection solution.

In a further embodiment, the killing, inactivation or decontamination occurs within about five minutes of coming into contact with the collection solution. In some embodiments, the killing, inactivation or decontamination occurs within about two minutes of coming into contact with the collection solution. In other embodiments, the killing, inactivation or decontamination occurs within about one minute of coming into contact with the collection solution.

In other embodiments, the sputum is solubilized so that the specimen can be extracted in less than about 1 hour, more preferably less than about 10 minutes, and in one more preferred embodiment, less than about 5 minutes. The invention provides a method to solubilize a sputum sample by disaggregating, degrading or depolymerizing mucoid or sputum components.

In certain applications of the present invention, particular advantages may be obtained when the collected population of polynucleotides is processed using at least a first nucleic acid extraction apparatus that is adapted and configured to facilitate recovery of substantially all of the nucleic acids present in a collected sample.

Exemplary extraction apparatuses and their methods of use include, without limitation, those devices and methods described in Applicants' commonly-owned U.S. patent application Ser. No. 12/916,263 (filed Oct. 29, 2010), which is specifically incorporated herein in its entirety by express reference thereto. Preferably, such an apparatus is a handheld device that isolates, separates or extracts nucleic acids from the collection solution and other cellular and microbial components in a matter of minutes without the need for devices requiring electricity and includes at least a first filtration vessel that has at least one receiving end and includes at least a first membrane filter adapted and configured to substantially bind at least a first population of nucleic acids thereto, wherein the first membrane filter is disposed at least substantially across a width of the filtration vessel and at least partially therein, a volume-dispensing mechanism adapted to contain, controllably dispense, and then forcibly inject at least a first amount of liquid operably associated with the filtration vessel to filter the liquid therethrough, and a collection container adapted to receive the filtered liquid.

In some embodiments, the population of polynucleotides obtained from the biological sample is further analyzed. The invention also encompasses a reagent mix for detection of a microbial sequence, preferably mycobacterial sequences, the reagent mix including one or more microbe-specific primers, probes, or enzymes, or a combination thereof, present in a mixture that is at least substantially stable at room temperature and is adapted and configured for use with a polymerase chain reaction (PCR) device. In one embodiment, the reagent mix is substantially stable at room temperature for at least about 5 days and up to two weeks. In another embodiment, the detection of the microbial sequence occurs within about 90 minutes after the microbial sequence is extracted from a sample. The reagent mix can be used to identify a microbial sequence, such as a pathogen, bacterial or viral sequence, or combination thereof. The reagent mix of the present invention, also referred to herein as a "PrimeMix®," and in some instances "PrimeMix® Universal MTB," can also be used to identify strains of a viral or bacterial sequence, or even species-specific tuberculin strains. Particular embodiments of compositions and methods of use can be found in Applicants' co-pending U.S. Patent Application Publication No. 2009/0098527 (filed Aug. 24, 2007), which is specifically incorporated herein in its entirety by express reference thereto.

A further embodiment can include a composition including at least one microbial-specific nucleic acid sequence or a biological sample suspected of containing at least one microbial-specific nucleic acid sequence; a solution comprising: (i) one or more buffers (each preferably present in the composition in an amount from about 1 mM to about 1M); (ii) one or more osmolarity agents at least one of which comprises betaine (each preferably present in the composition in an amount from about 1 mM to about 1M); (iii) one or more chelators (each preferably present in the composition in an amount from about 0.01 mM to about 1 mM); (iv) one or more reference dyes (each preferably present in the composition in an amount from about 0.01 µM to about 50 mM, more preferably about 0.02 µM to about 1 µM); and (v) one or more salts (each preferably present in the composition in an amount from about 50 mM to about 1M); and a first pair of Mycobacterial species-specific amplification primers. In some embodiments, the composition further includes at least a first Mycobacterial species-specific probe. In one embodiment, the reference dye is present in an amount of about 0.01 µM to about 1 µM.

The inclusion of one or more of such optional but preferred buffers is desirable to control the pH of the formulations, since it has been found that further processing of the nucleic acid, such as by polymerase chain reaction methodologies, is optimal in a pH range of about 7.5 to about 9.5. Exemplary buffers include, without limitation, tris(hydroxymethyl)aminomethane (Tris), citrate, 2-(N-morpholino)ethanesulfonic acid (MES), N,N-Bis(2-hydroxyethyl)-2-aminoethanesulfonic acid (BES), 1,3-bis(tris(hydroxymethyl)methylamino)propane (Bis-Tris), 4-(2-hydroxyethyl)-1-piperazineethanesulfonic acid (HEPES), 3-(N-morpholino)

propanesulfonic acid (MOPS), N,N-bis(2-hydroxyethyl) glycine (Bicine), N-[tris(hydroxymethyl)methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), bicarbonate, phosphate, or any combination thereof. In a preferred embodiment, the buffer includes TRIS.

At least a first osmolarity agent can be used within the method to optimize reaction conditions, especially when a high content of guanine and cytosine are present in the sequences, and can include, without limitation, betaine, trimethylglycine, glycine betaine, dimethylsulfoxide (DMSO), foramide, deoxyinosine, glycerine, 7-deaza deoxyguanosine triphosphate, or sodium hydroxide, or any combination thereof.

Exemplary chelators include, without limitation, ethylene glycol tetraacetic acid (EGTA), hydroxyethylethylenediaminetriacetic acid (HEDTA), diethylene triamine pentaacetic acid (DTPA), N,N-bis(carboxymethyl)glycine (NTA), ethylenediaminetetraacetic (EDTA), citrate anhydrous, sodium citrate, calcium citrate, ammonium citrate, ammonium bicitrate, citric acid, diammonium citrate, potassium citrate, magnesium citrate, ferric ammonium citrate, lithium citrate, or any combination thereof. In preferred embodiments, the chelator includes EDTA, a citrate, or a combination thereof. In a more preferred embodiment, the chelator includes EDTA.

At least a first reference dye, preferably an inert chemical, can optionally be used within the method to normalize the results obtained when using fluorescent compounds, such as those used in FRET technologies. The reference dye, when included, can provide an internal reference to which the reporter dye signal can be normalized. Such a reference dye can include, without limitation, passive reference dyes such as fluorescein, 5-carboxy-X-rhodamine and commercial formulations such as ROX™, or a combination thereof. In a more preferred embodiment, the reference dye includes ROX™.

Preferably, the compositions further include the addition of deoxynucleotide triphosphates (dNTPs), such as deoxyadenosine triphosphate, deoxyguanosine triphosphate, deoxycytidine triphosphate, deoxythymidine triphosphate, or deoxyurosine triphosphate, or a combination thereof, in an amount from about 0.1 mM to about 50 mM.

The compositions of the invention can further include one or more additional compounds or reagents including, but not limited to, bovine serum albumin (BSA), magnesium sulfate, water and acids or bases, such as hydrochloric acid and sodium hydroxide. The acids or bases can be added to the final solution to adjust the pH. Preferably, BSA is added in a concentration of about 0.01 µg/µL to about 0.5 µg/µL. Preferably, magnesium sulfate is added in a concentration of about 0.5 mM to about 50 mM.

The compositions of the invention can further include one or more polymerases. The one or more polymerases can include, but are not limited to, Taq polymerase, and high fidelity polymerases. Preferably, the one or more polymerases are present in an amount of about 1 U of enzyme to about 10 through about 50 µL of final solution.

In some embodiments, the preferable primer concentration for each primer is between about 1 pmol and about 10 µM.

In particular embodiments, the composition will further preferably include at least a first oligonucleotide detection probe that includes a radioactive, luminescent, chemiluminescent, fluorescent, enzymatic, magnetic, or spin-resonance label, or combination thereof. Fluorescent labels can include fluoroscein, 6-carboxyfluorescein (6-FAM), or 6-carboxyfluorescein-N-succinimidyl ester (6-FAMSE), or the like, or a combination thereof.

The invention further provides for a method for detecting the presence or absence of a *Mycobacterium*-specific nucleic acid segment in a population of polynucleotides obtained from a biological sample, the method including: (a) performing at least one thermal cycling step, wherein the cycling comprises at least a first amplifying step and at least a first hybridizing step, wherein the at least a first amplifying step comprises contacting a population of polynucleotides obtained from a biological sample suspected of containing a *Mycobacterium*-specific nucleic acid segment with a composition that comprises at least a pair of distinct, independently-selected, *Mycobacterium*-specific amplification primers, a polymerase, a first osmolarity agent comprising betaine, optionally (but preferably) at least a first reference dye, and a plurality of deoxynucleoside triphosphates to produce a *Mycobacterium*-specific amplification product when a *Mycobacterium*-specific nucleic acid segment is present in the sample; and (b) detecting the presence of the amplification product by contacting the amplification product with a *Mycobacterium*-specific oligonucleotide detection probe comprising a first detectable label, wherein the presence of a labeled hybridization product is indicative of the presence of one or more *Mycobacterium*-specific nucleic acid segments in the population of polynucleotides, wherein the pair of distinct, independently-selected, *Mycobacterium*-specific amplification primers comprises a first oligonucleotide primer of 18 to about 30 nucleotides in length, and a second oligonucleotide primer of 18 to about 30 nucleotides in length, wherein each of the first and second primers specifically hybridize to a first, and a second distinct sequence region, respectively, within the sequence of SEQ ID NO:1, or the complement or reverse complement thereof. In some embodiments, the method is compatible with at least one high throughput polymerase chain reaction technology. In other embodiments, the method further includes the sequencing of the detected *Mycobacterium*-specific nucleic acid segment.

Primers/Probes

In some embodiments, the pair of amplification primers includes a first, forward oligonucleotide primer of about 18 to about 30 nucleotides in length, wherein the first primer specifically hybridizes to a first distinct sequence region within the sequence 5'-GTCCCGCCGATCTCGTCCAGCGC-CGCTTCGGACCACCAGCACCTAACCGGCTGTG GGTAGCAGACCTCACCTATGTGTCGAC-CTGGGCAGGGTTCGCCTACGTGGCCTTTGT CAC-CGACGCCTACGTCGCAGGATC-CTGGGCTGGCGGGTCGCTTCCACGATGGCCACC TCCATGGTCCT-3' (SEQ ID NO:1), or the complement or reverse complement thereof. In other aspects, the pair of amplification primers includes a second, reverse oligonucleotide primer of about 18 to about 30 nucleotides in length, wherein the second primer specifically hybridizes to a second distinct sequence region within the sequence of SEQ ID NO:1, or the complement or reverse complement thereof. In yet further aspects, the pair of amplification primers includes a first oligonucleotide primer of about 18 to about 30 nucleotides in length, and a second oligonucleotide primer of about 18 to about 30 nucleotides in length, wherein each of the first and second primers specifically hybridize to a first, and a second distinct sequence region, respectively, within the sequence of SEQ ID NO:1, or the complement or reverse complement thereof.

In some aspects, the *Mycobacterium*-specific oligonucleotide detection probe includes a first oligonucleotide of about 24 to about 35 nucleotides in length that specifically hybridizes to at least a third sequence region of SEQ ID NO:1, or the complement or reverse complement thereof.

In particular aspects, the pair of amplification primers includes a first oligonucleotide primer of about 12 to about 50 nucleotides in length, in other aspects of about 14 to about 45 nucleotides in length, in yet other aspects of about 16 to about 40 nucleotides in length, in still yet other aspects of about 18 to about 30 or so nucleotides in length comprising a nucleic acid sequence that is at least 90% identical to one or more of the sequences of 5'-CTCGTCCAGCGCCGCTTC-3' (SEQ ID NO:2), or 5'-ACCAGCACCTAACCGGCT-3' (SEQ ID NO:5), or the complement thereof.

In particular aspects, the pair of amplification primers includes a first oligonucleotide primer of less than about 50, preferably less than about 40, and more preferably still, less than about 30 nucleotides in length that comprises, consists essentially of, or alternatively, consists of a nucleic acid sequence that is at least 90% identical to one or more of the sequences of 5'-ACAAAGGCCACGTAGGCGA-3' (SEQ ID NO:2), or 5'-TGCGACGTAGGCGTCGGT-3' (SEQ ID NO:5), or the complement thereof.

Likewise, in certain aspects, the pair of amplification primers includes a second oligonucleotide primer of 12 to about 50 nucleotides in length, in other aspects of about 14 to about 45 nucleotides in length, in yet other aspects of about 16 to about 40 nucleotides in length, in still yet other aspects of about 18 to about 30 or so nucleotides in length comprising a nucleic acid sequence that is at least 90% identical to one or more of the sequences of 5'-ACAAAGGCCACGTAGGCGA-3' (SEQ ID NO:3), or 5'-ACCGACGCCTACGTCGCA-3' (SEQ ID NO:6), or the complement or reverse complement thereof.

In some embodiments, the pair of amplification primers includes a second oligonucleotide primer of less than about 50, preferably less than about 40, and more preferably still, less than about 30 nucleotides in length that comprises, consists essentially of, or alternatively, consists of, a nucleic acid sequence that is at least 90% identical to one or more of the sequences of 5'-ACAAAGGCCACGTAGGCGA-3' (SEQ ID NO:3), or 5'-ACCGACGCCTACGTCGCA-3' (SEQ ID NO:6), or the complement or reverse complement thereof.

In particular aspects, the pair of amplification primers includes a first oligonucleotide primer of about 12 to about 50 nucleotides in length, in other aspects of about 14 to about 45 nucleotides in length, in yet other aspects of about 16 to about 40 nucleotides in length, in still yet other aspects of about 18 to about 30 or so nucleotides in length comprising a nucleic acid sequence that is at least 95% identical to one or more of the sequences of 5'-ACAAAGGCCACGTAGGCGA-3' (SEQ ID NO:2), or 5'-TGCGACGTAGGCGTCGGT-3' (SEQ ID NO:5), or the complement thereof.

In particular aspects, the pair of amplification primers includes a first oligonucleotide primer of less than about 50, preferably less than about 40, and more preferably still, less than about 30 nucleotides in length that comprises, consists essentially of, or alternatively, consists of a nucleic acid sequence that is at least 95% identical to one or more of the sequences of 5'-ACAAAGGCCACGTAGGCGA-3' (SEQ ID NO:2), or 5'-TGCGACGTAGGCGTCGGT-3' (SEQ ID NO:5), or the complement thereof.

Likewise, in certain aspects, the pair of amplification primers includes a second oligonucleotide primer of 12 to about 50 nucleotides in length, in other aspects of about 14 to about 45 nucleotides in length, in yet other aspects of about 16 to about 40 nucleotides in length, in still yet other aspects of about 18 to about 30 or so nucleotides in length comprising a nucleic acid sequence that is at least 95% identical to one or more of the sequences of 5'-ACAAAGGCCACGTAGGCGA-3' (SEQ ID NO:3), or 5'-ACCGACGCCTACGTCGCA-3' (SEQ ID NO:6), or the complement or reverse complement thereof.

In some embodiments, the pair of amplification primers includes a second oligonucleotide primer of less than about 50, preferably less than about 40, and more preferably still, less than about 30 nucleotides in length that comprises, consists essentially of, or alternatively, consists of, a nucleic acid sequence that is at least 95% identical to one or more of the sequences of 5'-ACAAAGGCCACGTAGGCGA-3' (SEQ ID NO:3), or 5'-ACCGACGCCTACGTCGCA-3' (SEQ ID NO:6), or the complement or reverse complement thereof.

In particular aspects, the pair of amplification primers includes a first oligonucleotide primer of about 12 to about 50 nucleotides in length, in other aspects of about 14 to about 45 nucleotides in length, in yet other aspects of about 16 to about 40 nucleotides in length, in still yet other aspects of about 18 to about 30 or so nucleotides in length comprising a nucleic acid sequence that is at least 98% identical to one or more of the sequences of 5'-ACAAAGGCCACGTAGGCGA-3' (SEQ ID NO:2), or 5'-TGCGACGTAGGCGTCGGT-3' (SEQ ID NO:5), or the complement thereof.

In particular aspects, the pair of amplification primers includes a first oligonucleotide primer of less than about 50, preferably less than about 40, and more preferably still, less than about 30 nucleotides in length that comprises, consists essentially of, or alternatively, consists of a nucleic acid sequence that is at least 98% identical to one or more of the sequences of 5'-ACAAAGGCCACGTAGGCGA-3' (SEQ ID NO:2), or 5'-TGCGACGTAGGCGTCGGT-3' (SEQ ID NO:5), or the complement thereof.

Likewise, in certain aspects, the pair of amplification primers includes a second oligonucleotide primer of 12 to about 50 nucleotides in length, in other aspects of about 14 to about 45 nucleotides in length, in yet other aspects of about 16 to about 40 nucleotides in length, in still yet other aspects of about 18 to about 30 or so nucleotides in length comprising a nucleic acid sequence that is at least 98% identical to one or more of the sequences of 5'-ACAAAGGCCACGTAGGCGA-3' (SEQ ID NO:3), or 5'-ACCGACGCCTACGTCGCA-3' (SEQ ID NO:6), or the complement or reverse complement thereof.

In some embodiments, the pair of amplification primers includes a second oligonucleotide primer of less than about 50, preferably less than about 40, and more preferably still, less than about 30 nucleotides in length that comprises, consists essentially of, or alternatively, consists of, a nucleic acid sequence that is at least 98% identical to one or more of the sequences of 5'-ACAAAGGCCACGTAGGCGA-3' (SEQ ID NO:3), or 5'-ACCGACGCCTACGTCGCA-3' (SEQ ID NO:6), or the complement or reverse complement thereof.

Preferably, when the first primer in the amplification primer pair comprises, consists essentially of, or alternatively consists of a sequence that is at least 90% identical to the sequence of 5'-ACAAAGGCCACGTAGGCGA-3' (SEQ ID NO:2), the second primer in the amplification pair comprises, consists essentially of or alternatively consists of a sequence that is at least 90% identical to the sequence of 5'-ACAAAG-GCCACGTAGGCGA-3' (SEQ ID NO:3), or the complement or reverse complement thereof. In such embodiments, a preferred oligonucleotide detection probe is one that comprises, consists essentially of, or alternatively consists of a sequence that is at least 90% identical to the sequence of 5'-ACCAC-CAGCACCTAACCGGCTGTGGGTA-3' (SEQ ID NO:4), or the complement thereof.

Preferably, when the first primer in the amplification primer pair comprises, consists essentially of, or alternatively consists of a sequence that is at least 90% identical to the sequence of 5'-TGCGACGTAGGCGTCGGT-3' (SEQ ID NO:5), the second primer in the amplification pair comprises, consists essentially of or alternatively consists of a sequence that is at least 90% identical to the sequence of 5'-ACCGACGCCTACGTCGCA-3' (SEQ ID NO:6). In such embodiments, a preferred oligonucleotide detection probe is one that comprises, consists essentially of, or alternatively consists of a sequence that is at least 90% identical to the sequence of 5'-AGGGTTCGCCTACGTGGCCTTTGT-3' (SEQ ID NO:7).

In certain illustrative aspects, the presence of an amplification product so produced in an amplification of the subject population of polynucleotides (such as for example, by using one or more PCR-based amplification methodologies) may be detected through the use of a labeled oligonucleotide probe that is specific for the amplification product so produced. In illustrative examples presented herein, the detection probe includes a first oligonucleotide probe of 24 to about 35 nucleotides in length, and further wherein the detection probe includes a nucleic acid sequence that comprises at least a first sequence region that is at least 85%, in other instances 90%, in other aspects at least 95%, and in yet other aspects at least 98% identical to a contiguous nucleic acid sequence as set forth in 5'-ACCAGCACCTAACCGGCTGTGGGTA-3' (SEQ ID NO:4), or 5'-AGGGTTCGCCTACGTGGCCTTTGT-3' (SEQ ID NO:7). In some embodiments presented herein, the detection probe includes a first oligonucleotide probe of less than about 50 nucleotides in length, preferably of less than about 40 nucleotides in length, and more preferably still of less than about 30 nucleotides in length, and further wherein the detection probe includes a nucleic acid sequence that comprises, consists essentially of, or alternatively consists of, the nucleic acid sequence of 5'-ACCAGCACCTAACCGGCTGTGGGTA-3' (SEQ ID NO:4), or 5'-AGGGTTCGCCTACGTGGCCTTTGT-3' (SEQ ID NO:7).

Exemplary formulations of the *Mycobacterium* PrimeMix® of the invention are described in the examples herein, and include, without limitation, a composition that includes: (a) about 1 U of Taq Polymerase; (b) about 6 µM of the detection probe which includes a nucleic acid sequence that comprises, consists essentially of, or alternatively consists of the nucleic acid sequence of 5'-ACCAGCACCTAACCGGCTGTGGGTA-3' (SEQ ID NO:4), or 5'-AGGGTTCGCCTACGTGGCCTTTGT-3' (SEQ ID NO:7); (c) about 4 µM of a reverse oligonucleotide primer of less than about 50, preferably less than about 40, and more preferably still, less than about 30 nucleotides in length that comprises, consists essentially of, or alternatively, consists of, a nucleic acid sequence that is at least 98% identical to one or more of the sequences of ACAAAGGCCACGTAGGCGA-3' (SEQ ID NO:3), or 5'-ACCGACGCCTACGTCGCA-3' (SEQ ID NO:6), or the complement thereof; (d) about 4 µM of a forward oligonucleotide primer of less than about 50, preferably less than about 40, and more preferably still, less than about 30 nucleotides in length that comprises, consists essentially of, or alternatively, consists of, a nucleic acid sequence that is at least 98% identical to one or more of the sequences of 5'-CTCGTCCAGCGCCGCTTC-3' (SEQ ID NO:2), or 5'-ACCAGCACCTAACCGGCT-3' (SEQ ID NO:5), or the complement thereof; (e) about 50 mM of Tris; (f) about 70 mM of KCl; (g) about 3 mM of MgSO4; (h) about 45 mM of Betaine; (i) about 0.05 µM of ROX or comparable reference dye; (j) about 0.025 µg/µl of ultra pure BSA; (k) about 0.2 mM of dNTPs; and (l) about 0.1 mM of EDTA.

A further embodiment of the invention includes a method for detection of a microbial sequence that includes obtaining genomic nucleic acid from a biological sample and assaying the genomic material by adding the nucleic acid to the reagent mix of one or more microbe-specific primers, probes, or enzymes, or a combination thereof, wherein the mix is substantially stable at room temperature and is adapted for use with a PCR device. In another embodiment, the PCR device includes fluorescence detection equipment for real-time PCR detection.

In a further embodiment, the invention provides a method for detecting the presence or absence of a Mycobacterial-specific nucleic acid segment, and in particular aspects, provides a method for detecting the presence or absence of a particular type, subtype, or strain of *M. tuberculosis*. In exemplary embodiments, the invention provides a method of identifying Mycobacterial species and strains that contain one or more IS6110-specific nucleic acid segments in a population of polynucleotides that is preferably obtained from a biological sample.

In another aspect, the present invention provides a method for rapidly detecting in a biological sample, a particular polynucleotide sequence, such as that of the *Mycobacterium*-specific IS6110 sequence. In an overall and general sense, this method comprises amplification of a population of nucleotides suspected of containing the particular sequence using conventional methods such as PCR and forward and reverse primers that are specific for the target sequence, hybridization of a specific probe set with the resulting single-stranded PCR product, performing melting curve analysis and analyzing the $T_m$ change of the hybrid of the single-stranded PCR product with the hybridization probes.

In an overall and general sense the method includes performing at least one cycling step, wherein the cycling step includes at least a first amplifying and at least a first hybridizing step, wherein the at least a first amplifying includes contacting a population of polynucleotides obtained from a biological sample suspected of containing a selected Mycobacterial-specific nucleic acid segment with a composition that includes at least a pair of distinct, independently-selected, Mycobacterial-specific amplification primers, a polymerase, a first osmolarity agent comprising betaine, and deoxynucleoside triphosphates to produce a Mycobacterial-specific amplification product if a Mycobacterial-specific nucleic acid segment is present in the sample; and detecting the presence of an amplification product so produced by contacting the amplification product with a Mycobacterial-specific oligonucleotide probe including a first detectable label, and wherein the presence of the labeled hybridization product is indicative of the presence of one or more Mycobacterial-specific nucleic acid segments in the population of polynucleotides. Preferably, the composition further includes at least a first reference dye.

The label on the probe can include, without limitation, radioactive, luminescent, chemiluminescent, fluorescent, enzymatic, magnetic, or spin-resonance labels known to those of ordinary skill in the molecular arts. In illustrative embodiments, the labeled probe contains at least a first minor groove binder. One such method for the detection of polynucleotides using a labeled "probe" sequence utilizes the process of fluorescence resonance energy transfer (FRET). Exemplary FRET detection methodologies often involve pairs of fluorophores comprising a donor fluorophore and acceptor fluorophore, wherein the donor fluorophore is capable of transferring resonance energy to the acceptor fluorophore. In exemplary FRET assays, the absorption spectrum of the donor fluorophore does not substantially overlap the absorption spectrum of the acceptor fluorophore. As used herein, "a donor oligonucleotide probe" refers to an oligonucleotide that is labeled with a donor fluorophore of a fluorescent resonance energy transfer pair. As used herein, "an acceptor oligonucleotide probe" refers to an oligonucleotide that is labeled with an acceptor fluorophore of a fluorescent resonance energy transfer pair. As used herein, a "FRET oligonucleotide pair" will typically comprise an "anchor" or "donor" oligonucleotide probe and an "acceptor" or "sensor" oligonucleotide probe, and such pair forms a FRET relationship when the donor oligonucleotide probe and the acceptor oligonucleotide probe are both hybridized to their complementary target nucleic acid sequences. Acceptable fluorophore pairs for use as fluorescent resonance energy transfer pairs are well known to those of ordinary skill in the art and include, but are not limited to, fluorescein/rhodamine, phycoerythrin/Cy7, fluorescein/Cy5, fluorescein/Cy5.5, fluorescein/LC Red 640, and fluorescein/LC Red 705, and the like.

In another embodiment, the invention provides an article of manufacture that includes a pair of Mycobacterial-specific oligonucleotide amplification primers; and a first Mycobacterial-specific oligonucleotide detection probe; wherein the detection probe includes at least one detectable label. Such article of manufacture may optionally further include, for example, one or more package insert(s) having instructions for using the pair of primers and the detection probe to detect the presence or absence of a Mycobacterial-specific nucleic acid segment within a population of polynucleotides obtained from a biological sample that was collected from a human subject.

In particular embodiments, the invention also provides a composition that includes:

(a) a population of polynucleotides isolated from a biological sample suspected of containing a Mycobacterial-specific nucleic acid segment;

(b) a first pair of amplification primers that specifically bind to a Mycobacterial-specific nucleic acid segment; and (c) a first labeled oligonucleotide detection probe that specifically binds to a Mycobacterial-specific amplification product; wherein the integrity of the population of polynucleotides is at least substantially maintained when the isolated polynucleotides are stored at a temperature of about 10° C. to about 40° C. for a period of about 1 to about 7 days. In some embodiments, the integrity of the population of polynucleotides is at least substantially maintained when the isolated polynucleotides are stored at a temperature of about 10° C. to about 40° C. for a period of about 7 to about 14 days, in other embodiments for a period of about 14 to about 30 days, and in yet other embodiments for 1 month up to about 4 months. In some embodiments, the composition further includes one or more components, buffers, enzymes, deoxynucleoside triphosphates, polymerases, reagents, or the like, or a combination thereof, wherein the composition is adapted to perform thermal cycling or a polymerase chain reaction. In related embodiments, the polynucleotide is amplified from a population of polynucleotides obtained from a human suspected of infection by one or more strains, subtypes, types, or species of Mycobacteria, including, without limitation, M. tuberculosis, M. Bovis, M. africanum, M. microti, M. cannetti, M. caprae and M. pinnipedi, or a combination thereof.

In particular embodiments, the first pair of amplification primers of the composition includes: (a) a first oligonucleotide primer of 18 to about 30 nucleotides in length including at least a first sequence region that consists of a sequence that is at least about 90% identical to the nucleic acid sequence of SEQ ID NO:2; and (b) a second oligonucleotide primer of 18 to about 30 nucleotides in length including at least a first sequence that consists of a sequence that is at least about 90% identical to the nucleic acid sequence of SEQ ID NO:3. In some embodiments the primers are at least about 80% identical, or at least about 85% identical to the above-mentioned nucleic acid sequences. In other embodiments, the primers are at least 95% identical, or at least 98% identical to the above-mentioned nucleic acid sequences. In particular embodiments, the composition includes a first oligonucleotide detection probe of 24 to about 35 nucleotides in length that includes at least a first sequence region that consists of a sequence that is at least about 90% identical to the nucleic acid sequence of SEQ ID NO:4. In related embodiments, the oligonucleotide detection probe further includes a radioactive, luminescent, chemiluminescent, fluorescent, enzymatic, magnetic or spin-resonance label, or a combination thereof.

In a related aspect, the invention also provides a composition that includes:

(a) a first pair of Mycobacterial-specific amplification primers, wherein the pair of primers includes:
(i) a first oligonucleotide primer of less than about 30 nucleotides in length that includes the nucleic acid sequence of SEQ ID NO:2; and
(ii) a second oligonucleotide primer of less than about 30 nucleotides in length that includes the nucleic acid sequence of SEQ ID NO:3; and (b) a first Mycobacterial-specific oligonucleotide detection probe, including:
(i) a first oligonucleotide detection probe of less than about 35 nucleotides in length, wherein the probe includes the nucleic acid sequence of SEQ ID NO:4; and
(ii) at least a first detection reagent operably linked to the oligonucleotide detection probe.

In particular embodiments, the first pair of amplification primers of the composition includes: (a) a first oligonucleotide primer of 18 to about 30 nucleotides in length including at least a first sequence region that consists of a sequence that is at least about 90% identical to the nucleic acid sequence of SEQ ID NO:5; and (b) a second oligonucleotide primer of 18 to about 30 nucleotides in length including at least a first sequence that consists of a sequence that is at least about 90% identical to the nucleic acid sequence of SEQ ID NO:6. In some embodiments the primers are at least about 80% identical, or at least about 85% identical to the above-mentioned nucleic acid sequences. In other embodiments, the primers are at least 95% identical, or at least 98% identical to the above-mentioned nucleic acid sequences. In particular embodiments, the composition includes a first oligonucleotide detection probe of 24 to about 35 nucleotides in length that includes at least a first sequence region that consists of a sequence that is at least about 90% identical to the nucleic acid sequence of SEQ ID NO:7. In related embodiments, the oligonucleotide detection probe further includes a radioactive, luminescent, chemiluminescent, fluorescent, enzymatic, magnetic or spin-resonance label, or a combination thereof.

In a related aspect, the invention also provides a composition that includes:

(a) a first pair of Mycobacterial-specific amplification primers, wherein the pair of primers includes:
(i) a first oligonucleotide primer of less than about 30 nucleotides in length that includes the nucleic acid sequence of SEQ ID NO:5; and
(ii) a second oligonucleotide primer of less than about 30 nucleotides in length that includes the nucleic acid sequence of SEQ ID NO:6; and (b) a first Mycobacterial-specific oligonucleotide detection probe, including:
    (i) a first oligonucleotide detection probe of less than about 35 nucleotides in length, wherein the probe includes the nucleic acid sequence of SEQ ID NO:7; and
    (ii) at least a first detection reagent operably linked to the oligonucleotide detection probe.

IPC

In the regular practice of the method, one may also perform the cycling step on one or more "negative" and/or "positive" control sample(s) as is routinely done in the molecular genetic assay arts to ensure integrity, fidelity, and accuracy of the method. The use of such controls is routine to those of ordinary skill in the art and need not be further described herein. Likewise, in the practice of the invention, it may also be desirable to incorporate one or more known "internal positive controls" (IPCs) into the population of polynucleotides to be isolated, to further ensure the integrity, fidelity, and/or accuracy of the disclosed method.

In certain embodiments, the addition of nucleic acids (e.g., RNA and/or DNA) is contemplated to be beneficial for a variety of purposes and applications of the disclosed methods: a) as a "carrier" (The addition of small amounts of supplemental RNA/DNA has been previously been shown to augment/increase the overall yield of samples/specimens, particularly original specimens that may contain low amounts of target, i.e., cells, viruses, bacteria); b) as an IPC for downstream molecular processes and to track or monitor the fidelity of the nucleic acid preparation from sample collection to detection; and c) for comparison to a 'calibrator' for downstream quantitative analysis, e.g., qRT-PCR and the like. In such embodiments, one or more known or "control" nucleic acids could be added to the compositions in a final concentration of from about 1 ag to about 1 mg, more preferably from about 1 fg to about 1 µg, and more preferably still, from about 1 pg to about 1 ng.

In an illustrative embodiment, the invention provides an isolated single-stranded (ss) or double-stranded (ds) RNA, DNA, PNA, or hybrid thereof that is useful: (a) as a carrier molecule for aiding in the recovery of polynucleotides from a biological sample suspected of containing nucleic acids, and/or (b) as an IPC (i.e., a "known," "reporter," "control," "standard," or "marker") sequence to monitor the integrity and fidelity of specimen collection and polynucleotide isolation/stabilization. In certain embodiments, the invention provides an isolated ds-RNA, ds-DNA, ds-PNA, or a hybrid thereof that is useful as a carrier molecule and/or an IPC. In other embodiments, the invention provides an isolated ssRNA, ssDNA, ssPNA, or a hybrid thereof that is useful as a carrier molecule and/or as an IPC sequence. In exemplary embodiments, the invention provides an isolated ssRNA molecule that is useful as both a carrier molecule and an IPC sequence.

Such molecules can be isolated from natural sources, prepared in the laboratory, or alternatively, a hybrid containing both native- and non-native sequences. As noted herein, because the compositions of the invention are particularly useful for the isolation and characterization of biological specimens obtained from mammalian (and in particular, human) sources that are suspected of containing polynucleotides of pathogen-origin, it is preferable that the sequence(s) employed as carrier and/or positive control compounds substantially contain a primary nucleotide sequence that is not ordinarily found within the genome of a mammal, or within the genome of an organism that is pathogenic to such a mammal. Exemplary mammals include, without limitation, bovines, ovines, porcines, lupines, canines, equines, felines, arsines, murines, leonines, leporines, hircines, and non-human primates.

Preferably, this non-mammalian, non-pathogen-specific carrier/reporter sequence is not cross-reactive, i.e., does not substantially, or preferably, do(es) not, hybridize to, mammalian or pathogen-specific sequences, and as such, non-coding, non-degenerate (i.e., nonsense) sequences are particularly preferred in the formulation of control carrier sequences to minimize hybridization of the control/carrier sequence to a member of the isolated population of polynucleotides obtained from the collected specimen. Exemplary carrier/control sequences therefore, do not substantially, or preferably, do(es) not, bind (e.g., hybridize under stringent hybridization conditions) to a population of polynucleotides isolated from a mammalian genome, or to a population of polynucleotides isolated from the genome of a bacterium, fungus, virus that is pathogenic to a mammal. Exemplary stringent hybridization conditions known to those of ordinary skill in the art include, without limitation, (a) pre-washing in a solution containing about 5×SSC, 0.5% SDS, and 1.0 mM EDTA (pH 8.0); (b) hybridizing at a temperature of from about 60° C. to about 70° C. in 5×SSC overnight; and (c) subsequently washing at about 65 to about 70° C. for 20 min. with each of 2×, 0.5× and 0.2×SSC containing 0.1% SDS), or equivalent hybridization conditions thereto. Particular compositions and methods of use can be found in Applicant's co-pending U.S. application Ser. No. 12/426,890, filed Apr. 20, 2009, which is incorporated by reference herein in its entirety.

In some embodiments, the method of collecting a biological sample suspected of containing at least a population of polynucleotides that is member of a *Mycobacterium tuberculosis* complex further includes an internal positive control that comprises an isolated, single- or double-stranded nucleic acid molecule of about 40 to 500 nucleotides in length, or a derivative thereof. In some embodiments, the internal positive control is a single stranded deoxyribonucleic acid that further includes: (a) at least 30 contiguous nucleotides from the sequence: 5'-GGGATCGTATAATCGTCGTGCAGT-CAGTCCCTCGGTTAAAGTCTCGAGTCGCTCTGT CAAAATATCCGTACCGTAGTCGATGC-GAGCGAGTCCGATCAGTCCAGGTTTCAAAGT CAAATGACTA-3' (SEQ ID NO:8), or the complement thereof; (b) a first sequence domain that specifically binds to a labeled probe of from about 15 to about 35 nucleotides in length that is specific for the detection of the nucleic acid segment; (c) a second sequence domain that specifically binds to a forward PCR amplification primer of about 15 to about 35 nucleotides in length; and (d) a third sequence domain that specifically binds to a reverse PCR amplification primer of about 15 to about 35 nucleotides in length; wherein the isolated deoxyribonucleic acid molecule remains at least substantially non-degraded when placed in the collection solution, and wherein the second and third sequence domains are operably positioned to facilitate a PCR-directed amplification of at least a first portion of the nucleic acid segment from the forward and reverse primers under conditions effective to amplify the at least a first portion.

In other embodiments, the invention provides for a method of determining the stability of a population of polynucleotides suspected of containing a *Mycobacterium tuberculosis* complex-specific nucleic acid segment by: (a) placing a known amount of the internal positive control of claim 7, a first forward polymerase chain reaction (PCR) amplification primer and a second reverse PCR amplification primer each of about 15 to about 35 nucleotides in length that is specific to SEQ ID NO:8, or the complement thereof, and a positive internal control-specific oligonucleotide detection probe of 24 to about 35 nucleotides in length that is specific to SEQ ID NO: 8, or the complement thereof into the composition containing the population of polynucleotides prior to amplification; (b) analyzing or quantitating the internal positive control and the population of polynucleotides obtained from the sample; and (c) comparing the known amount of the internal positive control to the amount of internal positive control present after amplification to ascertain the amount of nucleic acid degradation. In some embodiments, the first forward PCR amplification primer consists essentially of the nucleic acid segment of 5'-GTGCAGTCAGTCCCTCGGTTA-3' (SEQ ID NO:9), or the complement thereof; the second reverse PCR amplification primer consists essentially of the nucleic acid segment of 5'-TTGACTTTGAAACCTGGACT-GATC-3' (SEQ ID NO:10), or the complement thereof; and the positive internal control-specific oligonucleotide detection probe consists essentially of the nucleic acid segment of AAATATCCGTACCGTAGTCG (SEQ ID NO:11), or the complement thereof.

Kits

Another aspect of the invention provides for a reagent mixture incorporating the aforementioned primers and probes, and kits comprising such compositions for performance of a thermal cycling amplification method. In one embodiment, the invention provides a diagnostic nucleic acid amplification/detection kit that generally includes, in a suitable container, a Mycobacterial-specific oligonucleotide amplification primer set as described herein, and instructions for using the primer set in a PCR amplification of a population of polynucleotides obtained from a biological sample or specimen. Such kits may further optionally include, in the same, or in distinct containers, an oligonucleotide detection probe that specifically binds to the amplification product produced from PCR amplification of a population of polynucleotides obtained from a biological sample or specimen that contains, or is suspected of containing, a Mycobacterial-specific nucleic acid segment. Such kits may also further optionally include, in the same, or in a distinct container, any one or more of the reagents, diluents, enzymes, detectable labels (including without limitation, one or more radioactive, luminescent, chemiluminescent, fluorescent, enzymatic, magnetic, or spin-resonance labels), dNTPs, and such like that may be required to perform one or more thermal cycling amplifications of a population of polynucleotides as described herein.

Another aspect of the invention provides a kit for the collection and/or storage, and/or transport of the biological sample prior to genetic analysis of the population of polynucleotides encompassed therein. In such embodiments, a kit preferably includes one or more buffers, surfactants, chaotropes, DNAses, RNAses, or other such nucleic acid isolation and/or purification reagents as may be required to prepare a sample for analysis, such as those described above.

In further embodiments, the kits of the invention may also optionally further include one or more extraction devices or apparatuses, as described above, to facilitate the isolation or separation of the nucleic acids from the collected biological sample.

In certain embodiments, the kits of the invention may also optionally further include one or more portable, ruggedized, or field-employable thermal cycling, PCR amplification systems and/or one or more systems, devices, or instruments to facilitate detection, quantitation, and/or distribution of the detectable label(s) employed for visualization of the amplification products produced during the practice of the method.

The diagnostic reagents and kits of the present invention may be packaged for commercial distribution, and may further optionally include one or more collection, delivery, transportation, or storage devices for sample or specimen collection, handling, or processing. The container(s) for such kits may typically include at least one vial, test tube, flask, bottle, specimen cup, or other container, into which the composition(s) may be placed, and, preferably, suitably aliquoted for individual specimen collection, transport, and storage. The kit may also include a larger container, such as a case, that includes the containers noted above, along with other equipment, instructions, and the like. The kit may also optionally include one or more additional reagents, buffers, or compounds, and may also further optionally include instructions for use of the kit in the collection of a clinical, diagnostic, environmental, or forensic sample, as well as instructions for the storage and transport of such a sample once placed in one or more of the disclosed compositions.

It is contemplated that in certain embodiments, the compositions disclosed herein may be formulated such that the entire specimen collection and nucleic acid amplification/detection process may be accomplished in remote, field, battlefield, rural, or otherwise non-laboratory conditions without significantly limiting the fidelity, accuracy, or efficiency of the amplification/detection methodology. Such aspects of the invention provide particular advantages over conventional laborious isolation/collection/transport/storage/analysis protocols that require several days to several weeks to achieve, and must often be conducted under conditions that require refrigeration or freezing of the sample and/or assay reagents in order to properly complete the analysis. By providing reagent mixtures that include a mixture with all of the necessary isolation, storage, and polynucleotide stabilization components, as well as mixtures with all of the necessary reagents for amplification of selected target nucleotides (including, without limitation, the amplification primers and detection probes described herein, alone or in combination with one or more PCR buffers, diluents, reagents, polymerases, detectable labels, and such like), in a shelf-stable, ambient-temperature facile reagent mix, significant cost savings, time-reduction, and other economies of scale may be achieved using the present invention as compared to many of the conventional oligonucleotide probe-based thermal cycling assays commercially available. When a real-time PCR methodology is employed for the amplification, the detecting may optionally performed at the end of a given number of cycles, or alternatively, after one or more of each cycling step in the amplification protocol.

Any of the embodiments illustrated herein stand independently, and any features or embodiments may be combined in any way, unless expressly excluded, to achieve a preferred embodiment. Additional advantages and embodiments of the invention will also become more apparent to those of ordinary skill in the art based on the teachings of the present application.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which.

DESCRIPTION OF ILLUSTRATIVE EMBODIMENTS

Figure 1:
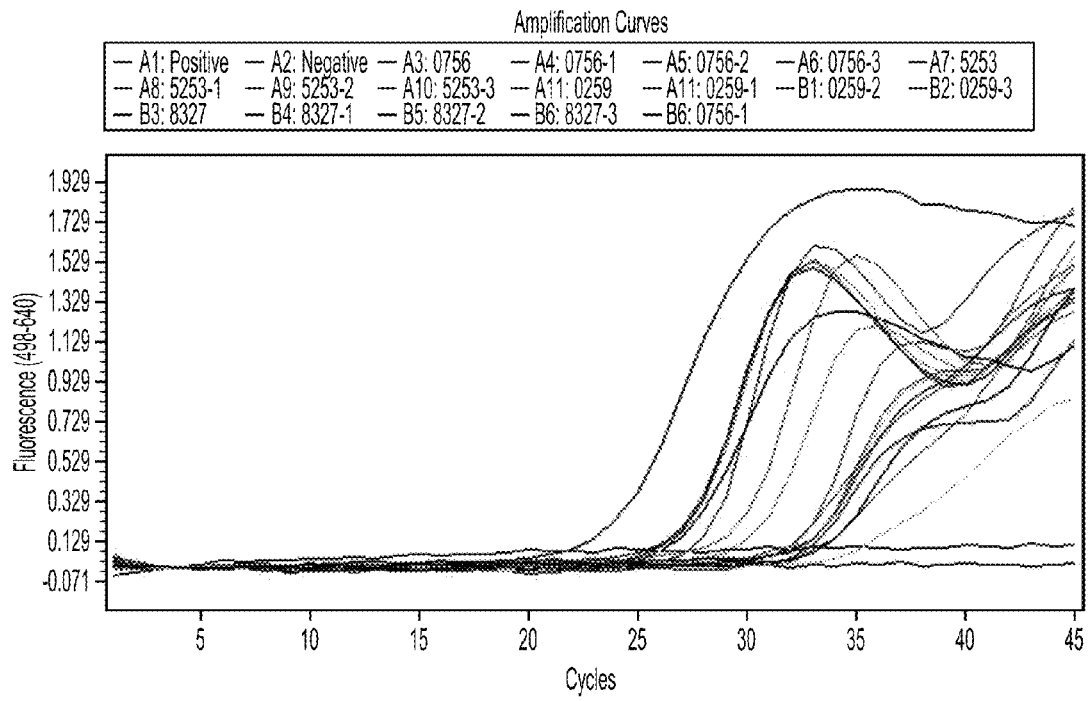
FIG. 1 illustrates the real time (RT) PCR analysis of tuberculin DNA from positive smear sputum samples preserved in PrimeStore® in a 1:1 ratio. In addition, the same smear positive sputum samples were swabbed, resulting in about 50 to about 400 microliters of sample on the swab, and the swabs placed in 1.5 mL of PrimeStore®. DNA was extracted from each sputum sample in PrimeStore® using the AMPLICOR® Respiratory Specimen Preparation Kit (AMPLICOR®, Roche Diagnostics, Basel, Switzerland) according to manufacturer's instructions. Four microliters of extracted DNA was used for real-time PCR using the LightCycler® *Mycobacterium* detection kit, according to the manufacturer's instructions. The resulting Cτ values for each of the samples is shown in Table 2.

Specimen Collection of Pathogen(s) from Biological Samples

Until recently, the majority of clinical diagnostic laboratories employed traditional culture for pathogen identification that typically requires 3-7 days for most viruses and longer for some bacterial strains, including up to about 21 days for the culturing of *M. tuberculosis*. Traditional culture requires specimen collection of viable microbes, frozen transport, and propagation and handling of potentially infectious and often unknown biological microbes. Furthermore, many infectious agents, e.g., highly pathogenic avian influenza, SARS, *M. tuberculosis* complex, etc., are BSL-3 level pathogens that require specialized facilities and precautions for analysis. There are challenges in obtaining, shipping and maintaining high-quality, viable biological specimens for culture. Specimens must be shipped using a cold chain, most often dry ice. Transporting potentially infectious samples from remote sites or across international borders using commercial transit can be costly and tedious, particularly when specimens must be received frozen.

The field of clinical molecular diagnostics changed drastically with the advent of polymerase chain reaction (PCR), and subsequently, real-time PCR. Real-time (RT-PCR) and real-time reverse transcription PCR (rRT-PCR) can deliver superior sensitivity and specificity results in hours. Thus, the majority of current diagnostic laboratories have transitioned from traditional culture to nucleic acid testing (NAT) such as real-time PCR.

Collection is the first step in diagnostic platforms or molecular protocols requiring the detection of potentially minute amounts of nucleic acids from microbes. Regardless of the nucleic acid test used or the RNA/DNA extraction protocol, specimen collection, specifically the inactivation of potentially infectious agents and the preservation and stability of pathogen RNA/DNA remains a critical gap in clinical diagnostics, especially for use around the world.

Mycobacteria are typically classified as an acid-fast Gram-positive bacteria due to their lack of an outer cell membrane. Acid-fast staining methods that are frequently used are the Ziehl-Neelsen stain or the Kinyoun method. They do not, generally, retain the crystal violet stain well and so are not considered a typical representative of Gram-positive bacteria. They do, however, contain a unique cell wall structure, which is thicker than that present in most other bacterial species. Typically, rod shaped, the cell wall consists of a hydrophobic mycolate layer (containing mycolic acids) and a peptidoglycan layer which is held together by arabinogalactan, a polysaccharide. This cell wall structure aids the mycobacteria in their ability to survive drastic environmental changes and contributes to the hardiness of the *Mycobacterium* species, as well in the difficulty in treating tuberculosis and leprosy patients, both of which are caused by different *Mycobacterium* species. Mycolic acids are strong hydrophobic molecules that form a lipid shell around the organism and affect permeability properties at the cell surface. Mycolic acids are thought to be a significant determinant of virulence in some *Mycobacterium* species. Most likely, they prevent attack of the mycobacteria by cationic proteins, lysozyme, and oxygen radicals in the phagocytic granule. They also protect extracellular mycobacteria from complement deposition in serum.

Additionally, mycobacteria are typically slow growing organisms, contributing to the difficulty of culturing the species. Due to their unique cell wall, they can survive long exposure to acids, alkalis, detergents, oxidative bursts, lysis by complement, and many antibiotics. Most mycobacteria are susceptible to the antibiotics clarithromycin and rifamycin, but antibiotic-resistant strains have emerged.

Members of the *Mycobacterium tuberculosis* complex, i.e., *M. tuberculosis, M. bovis, M. africanum, M. microti, M. cannetti, M. caprae* and *M. pinnipedi*, the causative agents of tuberculosis, have all of the above stated characteristics of mycobacteria. Typically, collection of biological samples suspected of containing members of the *M. tuberculosis* complex involves the collection of sputum from patients suspected of being infected with the same. Sputum is coughed up expectorate from the airways and ideally contains little to no saliva or nasal secretion, so as to avoid contamination of the sputum sample with oral bacteria. Sputum mainly contains mucus, a viscous colloid which is rich in glycoproteins. Patients suspected of having tuberculosis typically have an increased mucus viscosity, as well as increased production of mucus. In addition to mucus, sputum may contain blood, i.e., hemoptysis may occur, and/or pus, i.e., be purulent in nature.

Typically, patients suspected of having tuberculosis are asked to cough hard and then expectorate into a specimen cup in order to obtain a sputum sample. Usually, this procedure is done in a well ventilated area so as to minimize the potential for spreading infective mycobacteria. Patients may be asked to repeat this procedure in order to collect enough sputum for analysis, typically in amounts from about 5 mL to about 20 mL. The methods of the present invention allow for a minimal collection of sputum, i.e., about 0.01 mL to about 25 mL may be used, preferably about 0.05 mL to about 10 mL, more preferably 0.1 mL to about 5 mL. Typically, collected sputum samples are refrigerated until further analytic procedures, such as cell culturing or decontamination procedures to inactivate or kill any microorganisms contained within the sample, can be performed. In order to detect *Mycobacterium tuberculosis* in a sputum sample, an excess of 10,000 organisms per mL of sputum are needed to visualize the bacilli with a 100× microscope objective (1000× magnification). Direct smear microscopy of sputum samples from tuberculosis patients is typically regarded as an effective tool for monitoring patient response to treatment. Typically, more acid fast bacilli will be found in the purulent portions of the sputum.

The compositions and methods of the present invention are directed to the collection of a clinical or veterinary specimen or a forensic or environmental sample collection system and may include one or more collection tools and one or more reagents for efficiently: 1) obtaining a high yield of suitable specimen beyond what is currently available in the art; 2) inactivating potentially infectious biological pathogens, such as members of the *M. tuberculosis* complex, so that they are no longer viable and can be handled; shipped, or transported with minimal fear of pathogen release or contamination; or 3) effectively stabilizing and preserving lysed 'naked' RNA/DNA polymers from hydrolysis or nuclease degradation for prolonged periods at ambient temperatures until samples can be processed at a diagnostic laboratory, and preferably for achieving two or more, or all three, of these goals. The collection solutions of the present invention provide the following benefits: inactivation, killing, and/or lysis of microbes, viruses, or pathogens; destruction and/or inactivation of exogenous or endogenous nucleases, including, without limitation, RNase and/or DNase; compatibility with a variety of conventional nucleic acid extraction, purification, and amplification systems; preservation of RNA and/or DNA integrity within the sample; facilitation of transport and shipping at ambient or tropical temperatures, even over extended periods of time, or extreme temperature variations; and suitability for short—(several hours to several days), intermediate—(several days to several weeks), or long—(several weeks to several months) term storage of the isolated nucleic acids. Suitable compositions (also referred to as "PrimeStore®") and methods can be found in commonly owned U.S. Patent Pub. No. 2009-0312285, filed Oct. 1, 2008 (the entire contents of which is specifically incorporated herein in its entirety by express reference thereto).

In exemplary embodiments, the integrity of a population of polynucleotides in the biological sample, and/or the fidelity of at least a first sequence of at least one of the polynucleotides obtained from the sample is at least substantially maintained (i.e., at least 75%, in some cases about 80%, in other embodiments at least about 85%, or even at least about 90%, at least about 95% or at least about 98% of the nucleotides within the population are substantially full-length) when the composition including the sample is stored at a temperature of from about −20° C. to about 40° C., or from about −10° C. to about 40° C., or from about 0° C. to about 40° C., or from about 10° C. to about 40° C., for a period of from about 1 to about 7 days or longer; alternatively at a temperature of from about −20° C. to about 40° C., or from about −10° C. to about 40° C., or from about 0° C. to about 40° C., or from about 10° C. to about 40° C., for a period of from about 7 to about 14 days or longer; or alternatively at a temperature of from about or from about −10° C. to about 40° C., or from about 0° C. to about 40° C., or from about 10° C. to about 40° C. or from about 20° C. to about 40° C. for a period of from about 14 to about 42 days or more. In addition, the integrity of the polynucleotides within a population can be substantially maintained such that at least about 80% of the initial polynucleotides remain at least substantially full-length upon storage of the composition at a temperature from about −20° C. to about 40° C., preferably about 10° C. to about 40° C., for a period of from about 1 to about 14 days or longer; or alternatively at a temperature of from about −20° C. to about 40° C., preferably about 10° C. to about 40° C., for a period of from about 14 to about 42 days or longer.

Alternatively, the integrity of a population of polynucleotides in the biological sample is at least substantially maintained such that at least about 80%, at least about 85%, at least about 90%, or at least about 95%, 96%, 97%, 98% or 99% or more of the nucleotides within the population are present in the solution when compared to the amount present in the solution when the sample was initially collected. In preferred embodiments, the integrity of the sample will be substantially maintained such that all, or almost all of the bacteria-specific polynucleotides present in the initial sample will be maintained (i.e., not detectably degraded) over time.

In the practice of the disclosed methods, preferably from the time of collection to the time of isolating, purifying, or characterizing a population of polynucleotides therein, less than about 20% of the population of polynucleotides originally present in the collected sample will be degraded over time during subsequent storage. Preferably, substantially less than about 15% of the population of polynucleotides originally present in the collected sample will be degraded over time during subsequent storage, more preferably, less than about 10% of the population of polynucleotides originally present in the collected sample will be degraded over time during subsequent storage, and more preferably still, less than about 5% of the population of polynucleotides originally present in the collected sample will be degraded over time during subsequent storage. In particularly preferred embodiments, not more than about 5%, about 4%, about 3%, about 2% or about 1% of the population of polynucleotides originally present in the collected sample will be degraded over time during subsequent storage. Such high-integrity preservation of sample quality is preferable, regardless of the conditions under which the sample is stored, and will be substantially maintained for a period of time of at least about 1 day, at least about 5 days, at least about 7 days, at least about 14 days, at least about 21 days, at least about 30 days, at least about 45 days, at least about 60 days, at least about 90 days, or even at least about 120 days or more.

While the presence of, integrity of, or sequence fidelity of, a particular polynucleotide sequence obtained from, or utilized in the practice of the present invention may be determined using any conventional methodology known to those of ordinary skill in the molecular arts, in one embodiment, PCR amplification is utilized. Likewise, determination of the integrity of a polynucleotide of interest may include determination of the PCR cycle threshold ($C_T$) under given conditions, and determination of the sequence fidelity, qualitative integrity of collected nucleic acids may be determined by conventional DNA or RNA sequencing methods, including, without limitation, the chemical-based methods of Maxam-Gilbert, the dideoxy chain termination method of Sanger et al., the dye fluorophore-based method of Mathies et al., or pyrosequencing techniques as described by Nyren and Ronaghi. For example, nucleotide sequencing may be conducted by cloning purified amplicons using a TOPO® 2.0 Cloning Kit (Invitrogen™) and then sequenced using the BigDye® Terminator v3.1 reagent kit. Unincorporated fluorescent nucleotides can be removed using a DyeEx® 96-well plate kit per manufacturer's recommendations (Qiagen®). Nucleotide sequencing could further be performed using an ABI 3100 Genetic Analyzer (ABI Inc., Foster City, Calif., USA).

In certain embodiments, the target nucleic acids to be assayed for *M. tuberculosis* complex bacteria, will be obtained using a one-step sample collection/storage/transport medium that includes: a) one or more chaotropes (each preferably present in the composition an amount from about 0.5 M to about 6 M); b) one or more detergents (each preferably present in the composition an amount from about 0.1% to about 1%); c) one or more chelators (each preferably present in the composition in an amount from about 0.01 mM to about 1 mM); d) one or more reducing agents (each preferably present in the composition in an amount from about 0.05 M to about 0.3 M); and e) one or more defoaming agents (each preferably present in the composition in an amount from about 0.0001% to about 0.3%) to release such nucleic acids from a first biological sample suspected of containing one or more such target nucleic acids.

Methods of the present invention typically include collecting a biological sample suspected of containing at least a population of polynucleotides that is a member of a *Mycobacterium tuberculosis* complex by placing the biological sample into the collection solution of the invention. For sputum samples, this may be accomplished by coughing and expectorating into a specimen cup, vial, or collection container as described above, and then placing a portion of the expectorated sample into the collection solution of the present invention by swabbing or pipetting the sample. Alternatively, the patient may expectorate directly into the collection solution.

The amount of sputum sample as compared to the amount of collection solution can be minimal. For example, about 0.05 mL of sputum can be placed into about 1.2 mL of collection solution (about a 24-fold difference) and the population of polynucleotides contained within the sample can still be used in a variety of subsequent methodologies, including, without limitation, nucleic acid isolation, purification, amplification, and molecular analytical and/or diagnostic testing, assay, analysis, or characterization, and the like. In other words, the polynucleotides remain substantially, preferably entirely, maintained or substantially, preferably entirely, non-degraded. In addition, the amount of sputum sample as compared to the amount of collection solution can be about or greater than equal. For example, a 1:1 ratio of sputum to collection solution can also yield polypeptides that are substantially maintained or substantially non-degraded and able to be used in further analysis. Ratios of sputum to collection solution between about 1:1 and about 1:24 are also within the scope of this invention. Thus, the amount of collection solution used for a particular sputum sample can vary, providing extra flexibility of use.

Advantageously, by immersing the sputum sample into the collection solution, the viscosity of the sputum is reduced, thereby increasing the amount of bacilli that are accessed or contacted with the collection solution. In some embodiments, the viscosity of the sputum is decreased by up to about 50%. In other embodiments, the viscosity of the sputum is decreased by up to about 60%, by up to about 70%, by up to about 80%, or by up to about 90%. In yet still other embodiments, the viscosity of the sputum is reduced by about 95% when contacted with the collection solution. The addition of more collection solution increasingly reduces the viscosity of the sputum. Additionally, the tough cell wall of the *M. tuberculosis*-complex members is substantially broken down or degraded, resulting in the release of any polynucleotides contained therein.

Additionally, the inactivation, killing or decontamination of the *M. tuberculosis*-complex members may occur within about ten minutes or less of coming into contact with the sample. Preferably, this occurs within about five minutes or less. In other embodiments, this occurs within about 2 minutes or less. In some embodiments, this occurs within about 1 minute or less, in other embodiments, this occurs within about 30 seconds or less. In preferred embodiments, this occurs almost immediately upon contact of the *M. tuberculosis*-complex members with the collection solution.

Thus, the collection solutions and methods of the present invention provide a one-step procedure for inactivating, decontaminating and/or killing *M. tuberculosis*-complex members while releasing and preserving the polynucleotides contained therein. In a preferred embodiment, only one specimen cup, vessel, tube, vial or container for holding the sputum and one cup, vessel, tube, container or vial for holding the collection solution is necessary. In another embodiment, the patient may use the cup, vessel, tube, vial or container for holding the collection solution to expectorate into. This avoids the multi-step, multi-part and multi-component methodology of NaLc-NaOH decontamination, as presently used as a first step in possessing biological samples for nucleic acid analysis and as known to those of ordinary skill in the art.

Although the collection of sputum samples is described herein, the collection solutions and methods of the present invention may be used on any biological sample, such as, but not limited to, blood, bronchial lavage, plasma, pulmonary aspirates, cells, tissues, or serum, or any combination thereof.

Use of an Internal Positive Control ("IPC")

In some embodiments, the collection solution and methods may further include at least one internal positive control (IPC) to monitor fidelity of the processed samples, to monitor the integrity and fidelity of specimen collection and polynucleotide isolation/stabilization and/or to monitor downstream molecular processes or analysis. Methods include placing at least one IPC nucleic acid segment into the collection solutions of the present invention or combining the IPC nucleic acid segment with the extracted population of polynucleotides to monitor downstream molecular processing of the sample and/or extracted nucleic acid. In some embodiments, the IPC is present as a component of the PrimeStore® solution and, as such is substantially stable, and substantially non-degraded when stored in the solution for extended time periods at ambient temperatures. In these instances, the IPC may be considered part of the population of polynucleotides when extracted from the collection solution.

Preferably, the IPC sequence is not cross-reactive, i.e., does not substantially, or preferably, do(es) not, hybridize to, mammalian or pathogen-specific sequences, and as such, non-coding, non-degenerate (i.e., nonsense) sequences are particularly preferred in the formulation of control/carrier sequences to minimize hybridization of the control/carrier sequence to a member of the isolated population of polynucleotides obtained from the collected specimen. Exemplary carrier/control sequences therefore, do not substantially, or preferably, do(es) not, bind (e.g., hybridize under stringent hybridization conditions) to a population of polynucleotides isolated from a mammalian genome, or to a population of polynucleotides isolated from the genome of a bacterium, fungus, protozoan, virus that is pathogenic to a mammal.

In certain embodiments, the invention provides an isolated single stranded (ss)-RNA, ss-DNA, ss-PNA, double stranded (ds)-RNA, ds-DNA, ds-PNA, or a hybrid thereof, that is useful as an IPC. In preferred embodiments, where the isolation and detection of *M. tuberculosis*-complex specific nucleic acid is desired, a single stranded deoxyribonucleic acid segment is used. In illustrative embodiments, the invention provides for IPC sequences that comprise, consist essentially of, or consists of, nucleic acid sequences that are preferably at least about 80%, at least about 85%, at least about 90%, at least about 95%, at least about 96%, at least about 97%, at least about 98%, or at least about 99% or more identical to any one of SEQ ID NO:8, and SEQ ID NO:12 through SEQ ID NO:21.

Where further molecular processing of the sample or extracted nucleic acid consists of identification of *M. tuberculosis*-complex specific nucleic acids, the IPC sequences of the present invention should contain at least a first sequence domain that specifically hybridizes (i.e., binds) to a suitably-detectable probe, including, without limitation, molecularly-labeled probes and derivatives thereof. Exemplary labeled probes are those that include radioactive, luminescent, chemiluminescent, fluorescent, enzymatic, magnetic, or spin-resonance labels known to those of ordinary skill in the molecular arts. In preferred embodiments, the probe is labeled with 6-FAM or VIC™ dye. In illustrative embodiments, the labeled probe contains at least a first minor groove binder. In further embodiments, wherein amplification strategies such as PCR will be employed, the IPC sequences of the present invention contain at least a second sequence domain that specifically binds to a forward PCR amplification primer and a third sequence domain that specifically binds to a reverse PCR amplification primer.

Further suitable compositions and methods can be found in Applicants' commonly-owned U.S. Patent Appl. Publ. No. 2009/0233309 (filed Apr. 20, 2009), the contents of which is specifically incorporated herein in its entirety by express reference thereto.

Extraction of Nucleic Acids from Solutions Containing Biological Samples and the Collection Solution(s) of the Invention Following collection of the population of polynucleotides from a biological sample, any method of nucleic acid extraction or separation from the collection solution and microorganism debris, such as proteins, lipids and carbohydrates, may be performed, as would be known to one of ordinary skill in the art, including, but not limited to, the use of the standard phenol/chloroform purification, silica-based methods, and extraction methods based on magnetic glass particles. Compositions and methods used in the present invention are compatible with most, if not all, commercially available nucleic acid extraction compositions and methods, such as, but not limited to QiaAmp® DNA Mini kit (Qiagen®, Hilden, Germany), MagNA Pure 96 System (Roche Diagnostics, USA), and the NucliSENS® easyMAG® extraction system (bioMérieux, France). Generally, the extracted genomic nucleic acid is present in an amount from about 0.1 microliters to about 10,000 microliters, more preferably from about 1 microliter to about 1000 microliters, and more preferably from about 10 microliters to 100 microliters. An exemplary amount of nucleic acid is 25 microliters.

Suitable compositions and methods can be found in Applicants' commonly-owned U.S. patent application Ser. No. 12/916,263 (filed Oct. 29, 2010), the contents of which is specifically incorporated herein in its entirety by express reference thereto.

Compositions and Methods for Identification of M. Tuberculosis Complex-Specific Nucleic Acids The present invention also provides for compositions and methods of detecting *M. tuberculosis* complex-specific nucleic acid sequences present in a population of polynucleotides that has been isolated or extracted from a biological sample.

The polynucleotide compositions of the present invention, and particularly those useful in the detection of *M. tuberculosis* complex-specific nucleic acid sequences (including, for example, any one of or a combination of *M. tuberculosis, M. bovis, M. africanum, M. microti, M. cannetti, M. caprae* and *M. pinnipedi*-specific nucleic acids), preferably contain at least a single primer, or alternatively, two or more primers (e.g., "forward" and "reverse" primers) that may be used to facilitate amplification of the particular target nucleic acid sequence to be amplified. Exemplary primers useful in the practice of the invention include, but are in no way limited to, those primer sequences that specifically bind to the target nucleic acid sequence itself or to one or more regions immediately upstream (5') and or downstream (3') of the actual target nucleic sequence. In illustrative embodiments, the target sequence will also contain at least a first region to which a first detection probe (including, without limitation, luminescent, fluorescent, chemiluminescent, or FRET probes, or the like, as described herein) specifically binds.

The target sequence preferably includes at least a first nucleic acid that is specific for a *Mycobacterium*, and preferably one that is specific for at least first member of the *M. tuberculosis* complex. In illustrative embodiments, the at least a first nucleic acid is specific for the IS6110 insertion sequence found within members of the genus *Mycobacterium*. Preferably, the target sequence shares at least about 85%, at least about 90% or at least about 95% or greater sequence identity to at least a first contiguous nucleic acid segment of 5'-GTCCCGCCGATCTCGTCCAGCGCCGCT-TCGGACCACCAGCACCTAACCGGCTGTG GGTAG-CAGACCTCACCTATGTGTCGAC-CTGGGCAGGOTTCGCCTACGTGGCCTTTGT CACCGACGCCTACGTCGCAGGATC-CTGGGCTGGCGGGTCGCTTCCACGATGGCCACC TCCATGGTCCT-3' (SEQ ID NO:1).

The polynucleotides useful in the preparation of *M. tuberculosis* complex-specific probes and/or primer sequences described herein may also further optionally include one or more native, synthetic, homologous, heterologous, or hybrid promoter(s), enhancer(s), regulatory element(s), linker(s), spacer(s), binding domain(s), or transcription activation site(s), etc.

Primers useful in amplification of a particular sequence of interest may be designed using, for example, a computer program such as OLIGO® (Molecular Biology Insights Inc., Cascade, Colo., USA). Typically, oligonucleotide primers are from about 10 to about 60 or so nucleotides in length (including, without limitation, all intermediate integers, e.g., 10, 11, 12, etc., or even 60 or more nucleotides in length), although primers of any practical length may be useful in the practice of certain embodiments of the invention.

In one embodiment, the present invention provides oligonucleotide probes and primer sequences specific for tuberculosis-causing *mycobacterium*, and in particular, *M. tuberculosis* complex-specific nucleic acid segments. In illustrative embodiments, exemplary oligonucleotide primer sequences are disclosed that are useful in the detection and amplification of nucleic acid segments that are unique to particular types, subtypes and/or strains of tuberculosis or *M. tuberculosis* complex-specific bacteria. In additional embodiments, exemplary oligonucleotide detection probe sequences are disclosed that are particularly useful in the detection and quantitation of amplification products arising from such polynucleotides. Detection of these products when indicative of the presence of these *M. tuberculosis* complex-specific polynucleotides in a clinical sample can provide clinical diagnosticians and other medical professionals with a means for predicting and/or confirming the likelihood of particular tuberculosis infection in patients from whom such samples are collected. Such information may also be useful in the management of care for such individuals, and may also serve as molecular markers for determining the extent, significance, and/or rate of disease progression.

The oligonucleotide primers and probes of the present invention are designed for the selective amplification and detection of tuberculosis bacteria-encoding nucleic acid segments, and *M. tuberculosis*-encoding polynucleotides in particular. The disclosed primer sequences are suitable for use in hybridization methods, and in DNA amplification methods such as PCR-based amplification methods (including, for example, real-time PCR analyses). Likewise, the disclosed oligonucleotide detection probes are suitable for labeling with an appropriate label means for detection and quantitation of the products resulting from the amplification of nucleic acids using one or more pairs of the amplification primers disclosed herein.

In general, the oligonucleotide probes and primers finding particular utility in the practice of the disclosed methods should be of sufficient length to selectively hybridize to a complementary nucleic acid sequence, such as for example, a region of mycobacterial DNA, e.g., an IS6110 insertion sequence, obtained from a clinical isolate of a mammalian patient that is suspected of having, or at risk for developing, a tubercular infection, and an infection by *M. tuberculosis* in particular.

In particular, oligonucleotide primers and probes are selected such that they selectively hybridize to specific complementary nucleic acid sequences upstream and downstream of a region of DNA that encompasses a nucleic acid sequence from *M. tuberculosis* that is diagnostic of the *M. tuberculosis* genomic sequence. The selection of oligonucleotide probe and primer lengths is a process well-known in the molecular biological arts, and depends upon a number of parameters.

For most embodiments, the inventors contemplate that the length of the selected probe and primer compositions of the invention will preferably be less than about 50 to 60 or so nucleotides in length, and more preferably, will be less than about 40 to 45 or so nucleotides in length, while other probes and primers of the invention may be on the order of about 30 to 35 or so nucleotides in length. In some embodiments, the length of the selected oligonucleotide primer sequences (e.g., "forward" and "reverse" primers) and/or the length of the selected detection probe sequences (e.g., "anchor" and "sensor" probes), will likely be on the order of about 20 to 40 or so nucleotides in length, in some cases about 23 to about 40 nucleotides in length, or about 20 to about 30 nucleotides in length, although in some cases, the sizes of particular probes and primer sequences may be larger than that, and on the order of about 60 to 70 nucleotides in length. Alternatively, in some embodiments, it may be desirable to employ shorter probe and/or primer sequences, and as such, the oligonucleotides selected for practice of the invention may be on the order of about 15 to 28 or so nucleotides in length or even slightly shorter, such as about 15 to about 25 nucleotides, in some embodiments.

In the context of the present application, it is understood that all intermediate oligonucleotide lengths within the various ranges stated herein are contemplated to expressly fall within the scope of the present invention. To that end, oligonucleotides that are less than about 60, less than about 59, less than about 58, less than about 57, less than about 56, less than about 55, less than about 54, less than about 53, less than about 52, less than about 51, etc. are expressly within the scope of the present disclosure, as are oligonucleotides that are less than about 50, less than about 49, less than about 48, less than about 47, less than about 46, less than about 45, less than about 44, less than about 43, less than about 42, less than about 41, as well as oligonucleotides that are less than about less than about 40, less than about 39, less than about 38, less than about 37, less than about 36, less than about 35, less than about 34, less than about 33, less than about 32, less than about 31, as well as oligonucleotides that are less than about less than about 30, less than about 29, less than about 28, less than about 27, less than about 26, less than about 25, less than about 24, less than about 23, less than about 22, less than about 21, less than about 20, less than about 19, less than about 18, less than about 17, less than about 16, less than about 15, less than about 14, and so forth.

In the practice of the invention, forward and reverse amplification primers for use in the amplification of *M. tuberculosis* complex-specific polynucleotide sequences, and *M. tuberculosis*-encoding polynucleotide sequences in specific, preferably include at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23 or more contiguous nucleic acids from any one of the "forward" oligonucleotide primer sequence disclosed in SEQ ID NO:2 or SEQ ID NO:5 or the "reverse" oligonucleotide primer sequence disclosed in SEQ ID NO:3 or SEQ ID NO:6; or from oligonucleotide sequences that are at least about 80% identical, 90% identical, in some embodiments 95% identical and in other embodiments at least about 96% identical to the "forward" oligonucleotide primer sequence disclosed in SEQ ID NO:2 or SEQ ID NO:5, or the "reverse" oligonucleotide primer sequence disclosed in SEQ ID NO:3 or SEQ ID NO:6; or even from oligonucleotide sequences that are at least about 98% identical to the "forward" oligonucleotide primer sequence disclosed in SEQ ID NO:2 or SEQ ID NO:5, or the "reverse" oligonucleotide primer sequence disclosed in SEQ ID NO:3 or SEQ ID NO:6.

In some embodiments, the first oligonucleotide primer sequences are of 17 to about 60 nucleotides, or about 23 to about 50 nucleotides, in some embodiments 23 to about 40 nucleotides, and in yet other embodiments 23 to about 25 nucleotides, in length and include at least a first sequence region that consists of a sequence that is at least about 80% identical, at least about 85% identical, at least about 90% identical, in some embodiments at least about 95% identical and in yet other embodiments at least about 98% identical to the nucleic acid sequence of SEQ ID NO:2 or SEQ ID NO:5. Similarly, or in addition to the first oligonucleotide primer sequence, particular embodiments include a second oligonucleotide primer sequence of 20 to about 60 nucleotides, 25 to about 55 nucleotides, in some embodiments 25 to about 45 nucleotides, and in yet other embodiments 25 to about 30 nucleotides, in length and include at least a second sequence region that consists of a sequence that is at least 80% identical, at least about 85% identical, at least about 90% identical, in some embodiments at least about 95% identical and in yet other embodiments at least about 98% identical to the nucleic acid sequence of SEQ ID NO:3 or SEQ ID NO:6.

In other embodiments, the preferred oligonucleotide forward and reverse amplification primer sequences of the invention may comprise, consist essentially of, or alternatively consist of, the "forward" oligonucleotide primer sequence disclosed in SEQ ID NO:2 or SEQ ID NO:5 and the "reverse" oligonucleotide primer sequence disclosed in SEQ ID NO:3 or SEQ ID NO:6.

In yet additional embodiments, the forward and reverse amplification primer compositions preferred for the practice of the methods of the present invention may consist of a nucleic acid sequence that represents a contiguous nucleic acid sequence of about 6, about 7, about 8, about 9, about 10, about 11, about 12, about 13, about 14, or about 15, about 16, about 17, about 18, about 19, about 20, about 21, about 22, about 23, about 24, about 25, about 26, about 27, or more nucleotides as disclosed in SEQ ID NO:2, SEQ ID NO:3, SEQ ID NO:5 or SEQ ID NO:6.

In the practice of the invention, detection probes for use in the detection of *M. tuberculosis* complex-specific polynucleotide sequences, and *M. tuberculosis* strain in specific, using PCR, Real-time PCR, and/or FRET-based thermal cycling analyses described herein, will preferably include at least about 6, at least about 7, at least about 8, at least about 9, at least about 10, at least about 11, at least about 12, at least about 13, at least about 14, at least about 15, at least about 16, at least about 17, at least about 18, or more contiguous nucleic acids from the oligonucleotide detection probe sequence disclosed in SEQ ID NO:4 or SEQ ID NO:7; or from oligonucleotide sequences that are at least about 80%, at least about 85%, at least about 90%, at least about 95% identical to the oligonucleotide detection probe sequence disclosed in SEQ ID NO:4 or SEQ ID NO:7; or even from oligonucleotide sequences that are at least about 98% identical to the oligonucleotide probe sequence disclosed in SEQ ID NO:4 or SEQ ID NO:7.

As used herein, "nucleic acid" or "polynucleotide" compositions include, but are not limited to, those that contain either single-stranded or double-stranded polynucleotides, such as for example, deoxyribonucleic acids (DNA), ribonucleic acids (RNA), peptide nucleic acids (PNA), or any combinations or derivatives thereof (including, e.g., genomic, extragenomic, plasmid, cosmid, recombinant, artificial, and/or synthetic). Such sequences may be coding or non-coding sequences, sense, non-sense, or anti-sense sequences, and may, but need not, be present within one or more populations or pluralities of polynucleotides (either of the present invention, and a polynucleotide may, but need not, be linked to other molecules and/or support materials.

Likewise, polynucleotides of the present invention, and particularly those functioning as probes and/or primers specific for one or more particular types, subtypes, or strains of *M. tuberculosis* complex, need not be identical, or even substantially homologous to the particular sequences employed in the various embodiments of the invention illustrated herein. While the inventors have illustrated the use of particular probe and primer sequences as tools for identifying, amplifying, and quantitating a particular *M. tuberculosis* complex subtype or strain, such primers and/or probe sequences need not contain the particular nucleotide sequences employed in the illustrative examples provided herein.

In fact, in certain circumstances, polynucleotides useful as probe and/or primer sequences in the disclosed *M. tuberculosis* detection/identification system may include any suitable sequences that may be obtained, prepared, modified, or synthesized for such purpose. Moreover, in some instances, it is preferable that the probe and primer sequences utilized specifically hybridize to their particular target sequences, and do not share significant homology or substantially bind to other viral, bacterial, or fungal species, or to the genome of the host organism from which the biological sample was originally obtained. Likewise, it is desirable that the various probes and primer compositions used for the detection of particular subtypes and/or strains of a given *M. tuberculosis* complex also not cross-react, or hybridize to other or non-related nucleic acids that may also be present in the sample under assay.

As noted herein, the invention provides detection probes that contain at least a first sequence domain that specifically hybridizes (i.e., binds) to a suitably-detectable probe, including, without limitation, molecularly-labeled probes and derivatives thereof. Exemplary labeled probes are those that include radioactive, luminescent, chemiluminescent, fluorescent, enzymatic, magnetic, or spin-resonance labels known to those of ordinary skill in the molecular arts. In illustrative embodiments, the labeled probe contains at least a first minor groove binder. In certain embodiments, the detection probe may include a fluorescent label such as fluorescein, 6-carboxyfluorescein (6-FAM), or 6-carboxyfluoroscein-N-succinimidyl ester (6-FAMSE), VIC™ dye and the like, or a combination thereof.

In certain embodiments, to facilitate the binding of conventional detectable-label probes, the detection probes of the invention will contain at least a first sequence domain of from about 10 to about 60 nucleotides, in some instances about 10 to about 50 nucleotides, or about 10 to about 40 nucleotides, or about 10 to about 30 nucleotides, or about 10 to about 20 nucleotides in length that specifically binds to at least a first detectable probe. While the first sequence domain may be of any practical length within the entirety of the carrier sequence, preferably, the first sequence domain will be from about 12 to about 50 nucleotides in length; more preferably, from about 14 to about 45 nucleotides in length; still more preferably, from about 16 to about 40 or so nucleotides in length, and more preferably still, from about 18 to about 30 or so nucleotides in length.

In some embodiments, the oligonucleotide detection probe is from 18 to about 50 nucleotides in length and includes at least a first sequence region that includes a sequence that is at least 90% identical, in some embodiments at least 95% identical, to the nucleic acid sequence of SEQ ID NO:4 or SEQ ID NO:7.

As such, all intermediate lengths of probe-hybridizing sequence domains are contemplated to fall within the scope of the present disclosure, including, without limitation, probe-binding domains that are about 13 nucleotides in length, about 14 nucleotides in length, about 15 nucleotides in length, about 16 nucleotides in length, about 17 nucleotides in length, about 18 nucleotides in length, about 19 nucleotides in length, about 20 nucleotides in length, about 21 nucleotides in length, about 22 nucleotides in length, about 23 nucleotides in length, about 24 nucleotides in length, about 25 nucleotides in length, about 26 nucleotides in length, about 27 nucleotides in length, about 28 nucleotides in length, about 29 nucleotides in length, about 30 nucleotides in length, about 31 nucleotides in length, about 32 nucleotides in length, about 33 nucleotides in length, about 34 nucleotides in length, about 35 nucleotides in length, or even about 36, 37, 38, 39 or 40 or so nucleotides in length.

In exemplary embodiments, the amplification primers and detection probes may be prepared by one or more suitable molecular biology techniques, including, e.g., by the in vitro transcription of a polynucleotide that includes the sequence, or alternatively, includes a nucleic acid sequence that is complementary to the sequence.

In exemplary compositions and methods of PrimeMix®, the primers and probes of the invention are added to a particular formulation so that PCR may be performed. Preferably, about 8 μM of forward and reverse primers, about 6 μM of probe and about 1 unit of Taq are present in PrimeMix®. Exemplary concentration ranges of additional components of PrimeMix® can be seen in Table 1:

TABLE 1

FORMULATION RANGES OF EXEMPLARY COMPONENTS FOR THE PREPARATION OF PRIMEMIX ® COMPOSITIONS

| Reagent | Component Final Concentration Ranges |
|---|---|
| 1. One or more buffers, e.g.: Tris, citrate, MES, BES, Bis-Tris, HEPES, MOPS, Bicine, Tricine, ADA, ACES, PIPES, bicarbonate, phosphate | about 1 mM to about 1M |
| 2. One or more polymerase chain reaction osmolarity agents, e.g.: betaine, DMSO, foramide, glycerol, nonionic detergents, BSA, polyethylene glycol, tetramethylammonium chloride | about 1 mM to about 1M |
| 3. One or more chelators, e.g.: EGTA, HEDTA, DTPA, NTA, EDTA, citrate anhydrous, sodium citrate, calcium citrate, ammonium citrate, ammonium bicitrate, citric acid, diammonium citrate, potassium citrate, magnesium citrate, ferric ammonium citrate, lithium citrate | about 0.01 mM to about 1 mM |
| 4. One or more dyes, e.g.: fluorescein, 5-carboxy-X-rhodamine, ROX ™ | about 0.01 mM to about 50 mM |
| 5. One or more salts, e.g.: potassium chloride, magnesium sulfate, potassium glutamate | about 50 mM to about 1M |
| 6. One or more polymerases, e.g.: Taq, Pfu, KOD, Hot start polymerases, next gen. polymerases | about 0.05 U to about 1 U |
| 7. Deoxynucleoside triphosphates, e.g.: dATP, dTTP, dGTP, dCTP, dUTP | about 0.1 mM to about 1 mM |

Preferably, to this formulation a sufficient amount of primers and probe are added so as to amplify and detect the desired target.

2-amino-2-hydroxymethyl-propane-1,3-diol (TRIS) was obtained from Applied Biosystems/Ambion (Austin, Tex., USA). 2-[2-(Bis(carboxymethyl)amino)ethyl(carboxymethyl)amino]acetic acid (EDTA) GIBCO® UltraPure BSA was obtained from Invitrogen™ Corp. (Carlsbad, Calif., USA). All other reagents are available commercially from Sigma-Aldrich or USB Corporation.

In one embodiment, a 10× buffer solution is prepared as follows:

1—Add 2500 μL of 2 M Tris (pH 8.0) to a sterile 5.0 mL cryovial.
2—Add 3500 μL of 2 M KCl to the vial.
3—Add 300 μL of $MgSO_4$ to the vial.
4—Add 900 μL of 5M Betaine to the vial.
5—Add 200 μL of ROX™ to the vial.
6—Add 50 μL of BSA to the vial.
7—Add 800 μL of dNTP Mix to the vial.
8—Add 20 μL of 0.5 M EDTA to the vial.
9—Add 1600 μL+130 μL of nuclease-free water to the vial.
10—Close the vial and pulse vortex to thoroughly mix the contents.
11—Adjust the pH of the solution to pH 8.1-8.3 using 38% HCl.
12—Aliquot or transfer solution to a sterile container. Store at about −20° C. until ready to use.

When used within PrimeMix®, this 10× buffer solution is diluted to about 0.5× to about 2×, preferably, about 1×.

Compositions and Methods for Multiplex Analysis of Biological Samples

In some embodiments, it may be desirable to provide reagent mixtures that include more than a single pair of amplification primers and a detection probe that is specific for a given target nucleic acid sequence. For example, when it is desirable to determine the presence of two or more different types of mycobacteria, the composition of the invention may be formulated to contain a first pair of amplification primers that specifically bind to at least a first target region of an *M. tuberculosis*-specific polynucleotide, and a second pair of amplification primers that specifically bind to at least a first target region of an *M. bovis*-specific polynucleotide.

Alternatively, when it is desirable to determine the presence of two or more different tuberculosis causing mycobacteria, the composition of the invention may be formulated to contain a first pair of amplification primers that specifically bind to at least a first target region of a particular *M. tuberculosis*-specific polynucleotide, and a second pair of amplification primers that specifically bind to at least a first target region of a second, distinct, *M. tuberculosis, M. Bovis, M. africanum, M. microti, M. cannetti, M. caprae*, or *M. pinnipedi*-specific polynucleotide.

Additionally, when it is desirable to determine the presence of one or more additional microorganisms, i.e., to identify whether a patient is co-infected, with other bacterial, or fungal, or viral infections, for example, gram-positive and gram-negative bacteria, human immunodeficiency virus, pneumococcus, influenza, *Yesinia pestis, Pseudomonas* sp., *Stenotrophomonas maltophilia, Burkholderia cepacia, Streptococcus* sp., *Moraxella catarrhalis, Enterobacteriaceae, Haemophilus* sp., *Staphylococcus* sp., Rhinovirus, Respiratory syncytial virus, Coronavirus, Adenovirus, *Chlamydophila pneumoniae, Mycoplasma pneumoniae, Pneumocystis jiroveci*, and the like.

In some instances, it is desirable to test for drug resistance genes or mutations within the *M. tuberculosis* complex-specific polynucleotide. Multi-drug resistant (MDR)-TB strains could arise as a consequence of sequential accumulation of mutations conferring resistance to single agents, or by a single step process such as acquisition of an MDR element. A series of distinct mutations conferring resistance to Rifampin, INH, Streptomycin, Ethambutol, ETH, PZA, Kanamycin, and quinolones has been identified. Some of these MDR isolates arise because random mutations in genes that encode targets for the individual anti-microbial agents are selected by sub-therapeutic drug levels resulting from treatment errors, poor adherence to treatment protocols, or other factors.

In these embodiments, the composition of the invention may be formulated to contain a first pair of amplification primers that specifically bind to at least a first target region of a particular *M. tuberculosis* complex-specific polynucleotide, and a second pair of amplification primers that specifically bind to at least a first target region of a drug resistance-polynucleotide found within, for example, multi-drug resistant tuberculosis strains or extensively-drug resistance tuberculosis strains. This can include resistance to rifampicin and/or isoniazid (resistance to these first-line anti-TB drugs classically defines a multi-drug resistant [MDR] tuberculosis), as well as to one or more members of the quinolone family, or kanamycin, capreomycin or amikacin, or any combination thereof.

In addition, when an IPC is added to an initial collection solution or the extracted nucleic acid sample, the composition may be further or additionally formulated to include a first pair of amplification primers that specifically bind to at least a first target region of a particular IPC polynucleotide.

For detection of the particular amplification product(s) produced from such compositions, the compositions will also further include a first detection probe that specifically binds to the amplification product produced from the first pair of amplification primers, and a second distinct detection probe that specifically binds to the amplification product produced from the second pair of amplification primers. In such compositions, it is preferable that the two, three or four detection probes present in the formulation be distinct, such that each of the probes (if specifically bound to a target in the resulting amplification mixture) may be individually detectable using conventional methodologies. Such probe distinctiveness is readily achievable in the conventional arts, using, for example, detection probes that include detection moieties that fluoresce at two, three or four distinctly-different wavelengths.

In some aspects of the invention, the amplification and/or detection of target nucleic acids may be done sequentially, while in other aspects, it may be desirable to amplify and/or detection multiple target nucleic acids simultaneously. For example, a given biological sample could first be screened for the presence of *M. tuberculosis*-specific target sequence(s), and if none are found, the sample then secondarily screened for the presence of *M. bovis, M. africanum, M. microti, M. cannetti, M. caprae* and *M. pinnipedi*-specific target sequence(s).

The methods for nucleic acid hybridization are considered routine to those of ordinary skill in the molecular biological arts, and as such, a detailed discussion of analytical methods employing them need not be provided herein. However, as a guidance, "moderately stringent" hybridization conditions popularized by Southern et al. are generally considered in the art to include, e.g., pre-washing in a solution containing about 5× standard sodium citrate buffer (SSC), 0.5% sodium dodecyl sulfate (SDS), 1.0 mM ethylenediaminetetraacetic acid (EDTA) (e.g., pH 8.0); hybridizing at a temperature of from about 50° C. to about 60° C. in 5×SSC overnight; followed by washing twice at about 60 to 65° C. for 20 min. with each of 2×, 0.5× and 0.2×SSC containing 0.1% SDS). Likewise, "stringent" hybridization conditions typically include, e.g., pre-washing in a solution containing about 5×SSC, 0.5% SDS, 1.0 mM EDTA (pH 8.0); hybridizing at a temperature of from about 60° C. to about 70° C. in 5×SSC overnight; followed by washing twice at about 65 to 70° C. for 20 min with each of 2×, 0.5× and 0.2×SSC containing 0.1% SDS). Similarly, representative examples of "highly-stringent" hybridization conditions include, but are not limited to, pre-washing in a solution containing about 5×SSC, 0.5% SDS, 1.0 mM EDTA (pH 8.0); hybridizing at a temperature of from about 70° C. to about 75° C. in 5×SSC overnight; followed by washing twice at about 70° C. to about 75° C. for 20 mM. with each of 2×, 0.5× and 0.2×SSC containing 0.1% SDS).

It will also be appreciated by those of ordinary skill in the art that, as a result of the degeneracy of the genetic code, there are many nucleotide sequences that encode a given primary amino acid sequence. Some of these polynucleotides bear minimal homology to the nucleotide sequence of any native gene. Nonetheless, polynucleotides that vary due to differences in codon usage are specifically contemplated by the present invention.

Detection probes and amplification primers may be prepared by conventional molecular biology recombination methodologies, or alternatively synthesized in whole or in part by conventional methods known in the art, including chemical synthesis (e.g., solid phase phosphoramidite chemical synthesis) and the like. Modifications in a polynucleotide sequence may also be introduced using standard mutagenesis techniques, such as oligonucleotide-directed site-specific mutagenesis. RNA molecules for use as detection probes or primers may also be directly synthesized, or alternatively, be prepared by in vitro or in vivo transcription of DNA sequences using suitable systems (such as T3, T7, and SP6 polymerases and the like).

Polynucleotides of the present invention may be modified to increase stability either in vitro and/or in vivo. Such modifications include, without limitation, the addition of flanking sequences at the 5'-end, 3'-end, or both; the use of phosphorothioate or 2'-o-methyl rather than phosphodiesterase linkages in the backbone; and/or the inclusion of nontraditional bases such as inosine, queosine and wybutosine, as well as acetyl-, methyl-, thio-, or otherwise-modified forms of adenine, cytidine, guanine, thymine and uridine, or any combination thereof.

Nucleotide sequences as described herein may be joined or linked to a variety of other nucleotide sequences using established recombinant techniques. For example, a polynucleotide useful as an amplification probe or detection primer may be produced by cloning into any of a variety of cloning vectors, including one or more of plasmids, phagemids, lambda phage derivatives and cosmids. Vectors of particular interest include expression vectors, replication vectors, probe generation vectors, and sequencing vectors. In general, a vector will contain an origin of replication functional in at least one organism, convenient restriction endonuclease sites and one or more selectable markers. Other elements will depend upon the desired use, and will be apparent to those of ordinary skill in the art. Alternatively, probe and primer-specific oligonucleotide sequences may be prepared through one or more template-dependent or amplicon-directed recombinant production methodologies that are known to those of ordinary skill in the arts.

In particular embodiments, the present invention provides polynucleotide compositions that may be added to the disclosed collection/storage/transport media to provide one or more amplification primer(s) and or detection probe(s) to analyze and/or characterize a population of target polynucleotides isolated, for example, from a biological sample or specimen. Such polynucleotide compositions may contain one or more sequence domains to which specific polymerases may bind, and may serve as suitable amplification primers, and/or detection probes.

Oligonucleotide primers and probes of the present invention may be designed for the selective amplification and detection of one or more specific target nucleic acids, including, for example, those sequences that are specific for a single strain, subtype, or type of Influenza virus. Such primer sequences are suitable for use in hybridization methods, and in amplification methods such as PCR-based amplification methods (including, for example, real-time PCR analyses, RT-PCR and the like). Likewise, the disclosed oligonucleotide detection probes are suitable for labeling with an appropriate label for detection and quantitation of the products resulting from the amplification of nucleic acids using one or more pairs of the amplification primers disclosed herein.

Exemplary Definitions

In accordance with long standing patent law convention, the words "a" and "an" when used in this application, including the claims, denotes "one or more."

As used herein, the terms "about" and "approximately" are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

The terms "e.g.," and "i.e." as used herein, is used merely by way of example, without limitation intended, and should not be construed as referring only those items explicitly enumerated in the specification.

As used herein, the term "infection," "mycobacterial infection," "bacterial infection," "tubercular infection," and the like are used consistently with their accepted meanings in the art, but can also encompass the detrimental effect of a biological organism that does not result in an infection as conventionally understood. The term "methods of treating" includes methods of managing, and when used in connection with the biological organism or infection, includes the amelioration, elimination, reduction, prevention, or other relief or management from the detrimental effects of a biological organism. In a preferred embodiment, these detrimental effects include a mycobacterial infection, symptoms characterizing and/or effects associated with tuberculosis in the subject, or a combination thereof.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained, and also in the case of pathogens, optionally isolated away from, or purified free from total mammalian (preferably human) genomic DNA of the infected individual. Included within the term "DNA segment," are DNA segments and smaller fragments of such segments, as well as recombinant vectors, including, for example, plasmids, cosmids, phage, viruses, and the like.

Similarly, the term "RNA segment" refers to an RNA molecule that has been isolated free of total cellular RNA of a particular species. Therefore, RNA segments obtained from a biological sample using one of the compositions disclosed herein, refers to one or more RNA segments (either of native or synthetic origin) that have been isolated away from, or purified free from, other RNAs. Included within the term "RNA segment," are RNA segments and smaller fragments of such segments.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

The phrase "substantially identical," in the context of two nucleic acids refers to two or more sequences or subsequences that have at least about 90%, preferably 91%, most preferably about 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide residue identity, when compared and aligned for maximum correspondence, as measured using a sequence comparison algorithm or by visual inspection. Such "substantially identical" sequences are typically considered "homologous," without reference to actual ancestry.

As used herein, "sample" includes anything containing or presumed to contain a substance of interest. It thus may be a composition of matter containing nucleic acid, protein, or another biomolecule of interest. The term "sample" can thus encompass a solution, cell, tissue, or population of one or more of the same that includes a population of nucleic acids (genomic DNA, cDNA, RNA, protein, other cellular molecules, etc.). The terms "nucleic acid source," "sample," and "specimen" are used interchangeably herein in a broad sense, and are intended to encompass a variety of biological sources that contain nucleic acids, protein, one or more other biomolecules of interest, or any combination thereof. Exemplary biological samples include, but are not limited to, whole blood, plasma, serum, sputum, urine, stool, white blood cells, red blood cells, buffy coat, swabs (including, without limitation, buccal swabs, throat swabs, vaginal swabs, urethral swabs, cervical swabs, rectal swabs, lesion swabs, abscess swabs, nasopharyngeal swabs, and the like), urine, stool, sputum, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluids from cysts or abscesses, synovial fluid, vitreous or aqueous humor, eye washes or aspirates, bronchial or pulmonary lavage, lung aspirates, and organs and tissues, including but not limited to, liver, spleen, kidney, lung, intestine, brain, heart, muscle, pancreas, and the like, and any combination thereof.

Tissue culture cells, including explanted material, primary cells, secondary cell lines, and the like, as well as lysates, homogenates, extracts, or materials obtained from any cells, are also within the meaning of the term "biological sample," as used herein. Microorganisms (including, without limitation, prokaryotes such as the archaebacteria and eubacteria; cyanobacteria; fungi, yeasts, molds, actinomycetes; spirochetes, and mycoplasmas); viruses (including, without limitation the Orthohepadnaviruses [including, e.g., hepatitis A, B, and C viruses], human papillomavirus, Flaviviruses [including, e.g., Dengue virus], Lyssaviruses [including, e.g., rabies virus], Morbilliviruses [including, e.g., measles virus], Simplexviruses [including, e.g., herpes simplex virus], Polyomaviruses, Rubulaviruses [including, e.g., mumps virus], Rubiviruses [including, e.g., rubella virus], Varicellovirus [including, e.g., chickenpox virus], rotavirus, coronavirus, cytomegalovirus, adenovirus, adeno-associated virus, baculovirus, parvovirus, retrovirus, vaccinia, poxvirus, and the like), algae, protozoans, protists, plants, bryophytes, and the like, and any combination of any of the foregoing, that may be present on or in a biological sample are also within the scope of the invention, as are any materials obtained from clinical or forensic settings that contain one or more nucleic acids are also within the scope of the invention. The ordinary-skilled artisan will also appreciate that lysates, extracts, or materials obtained from any of the above exemplary biological samples are also within the scope of the invention.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "biological molecule" refers to any molecule found within a cell or produced by a living organism, including viruses. This may include, but is not limited to, nucleic acids, proteins, carbohydrates, and lipids. As used herein, a "cell" refers to the smallest structural unit of an organism that is capable of independent functioning and is included of cytoplasm and various organelles surrounded by a cell membrane. This may include, but is not limited to, cells that function independently such as bacteria and protists, or cells that live within a larger organism such as leukocytes and erythrocytes. As defined herein, a cell may not have a nucleus, such as a mature human red blood cell.

Samples in the practice of the invention can be used fresh, or can be used after being stored for a period of time, or for an extended period of time, including for example, cryopreserved samples and the like, and may include material of clinical, veterinary, environmental or forensic origin, may be isolated from food, beverages, feedstocks, potable water sources, wastewater streams, industrial waste or effluents, natural water sources, soil, airborne sources, pandemic or epidemic populations, epidemiological samples, research materials, pathology specimens, suspected bioterrorism agents, crime scene evidence, and the like.

As used herein, the term "patient" (also interchangeably referred to as "host" or "subject") refers to any host that can serve as a source of one or more of the biological samples or specimens as discussed herein. In certain aspects, the donor will be a vertebrate animal, which is intended to denote any animal species (and preferably, a mammalian species such as a human being). In certain embodiments, a "patient" refers to any animal host, including but not limited to, human and non-human primates, avians, reptiles, amphibians, bovines, canines, caprines, cavities, corvines, epines, equines, felines, hircines, lapines, leporines, lupines, ovines, porcines, racines, vulpines, and the like, including, without limitation, domesticated livestock, herding or migratory animals or birds, exotics or zoological specimens, as well as companion animals, pets, and any animal under the care of a veterinary practitioner. The invention may also be used to monitor disease outbreak, progression, spread, or one or more other epidemiological statistics within, among, or between one or more global populations, including, without limitation, the spread of mycobacterial infections, the development of clinical signs of tubercular disease, and/or comorbidity with one or more additional infections such as, without limitation, wasting syndrome, Dengue fever, ebola, HIV, SARS, and one or more bacterial or viral infections, including, without limitation, pneumonias, influenzas, and the like. In certain embodiments, the samples will preferably be of mammalian origin, and more preferably of human origin.

The term "substantially free" or "essentially free," as used herein, typically means that a composition contains less than about 10 weight percent, preferably less than about 5 weight percent, and more preferably less than about 1 weight percent of a compound. In a preferred embodiment, these terms refer to less than about 0.5 weight percent, more preferably less than about 0.1 weight percent or even less than about 0.01 weight percent. The terms encompass a composition being entirely free of a compound or other stated property, as well. With respect to degradation or deterioration, the term "substantial" may also refer to the above-noted weight percentages, such that preventing substantial degradation would refer to less than about 15 weight percent, less than about 10 weight percent, preferably less than about 5 weight percent, etc., being lost to degradation. In other embodiments, these terms refer to mere percentages rather than weight percentages, such as with respect to the term "substantially non-pathogenic" where the term "substantially" refers to leaving less than about 10 percent, less than about 5 percent, etc., of the pathogenic activity.

As used herein, the term "heterologous" is defined in relation to a predetermined referenced nucleic acid sequence. For example, with respect to a structural gene sequence, a heterologous promoter is defined as a promoter that does not naturally occur adjacent to the referenced structural gene, but which is positioned by the hand of man in one or more laboratory manipulations that are routinely employed by those of ordinary skill in the molecular biological arts. Likewise, a heterologous gene or nucleic acid segment is defined as a gene or nucleic acid segment that does not naturally occur adjacent to the referenced sequence, promoter and/or enhancer element(s), etc.

As used herein, the term "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

The terms "identical" or percent "identity", in the context of two or more nucleic acid or polynucleotide sequences, refer to two or more sequences or subsequences that are the same or have a specified percentage of nucleotides that are the same, when compared and aligned for maximum correspondence over a comparison window, as measured using a sequence comparison algorithm or by manual alignment and visual inspection.

A "primer" or "primer sequence" may include any nucleic acid sequence or segment that selectively hybridizes to a complementary template nucleic acid strand ("target sequence") and functions as an initiation point for the addition of nucleotides to replicate the template strand. Primer sequences of the present invention may be labeled or contain other modifications which allow the detection and/or analysis of amplification products. In addition to serving as initiators for polymerase-mediated duplication of target DNA sequences, primer sequences may also be used for the reverse transcription of template RNAs into corresponding DNAs.

A "target sequence" or "target nucleotide sequence" as used herein includes any nucleotide sequence to which one of the disclosed primer sequences hybridizes under conditions that allow an enzyme having polymerase activity to elongate the primer sequence, and thereby replicate the complementary strand.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to all amino acid chain lengths, including those of short peptides of about 2 to about 20 amino acid residues in length, oligopeptides of about 10 to about 100 amino acid residues in length, and polypeptides of about 100 to about 5,000 or more amino acid residues in length. The term "sequence," when referring to amino acids, relates to all or a portion of the linear N-terminal to C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide and polynucleotide chains, "sequence" and "subsequence" have similar meanings relating to the 5' to 3' order of nucleotides.

As used herein, the term "substantially homologous" encompasses two or more biomolecular sequences that are significantly similar to each other at the primary nucleotide sequence level. For example, in the context of two or more nucleic acid sequences, "substantially homologous" can refer to at least about 75%, preferably at least about 80%, and more preferably at least about 85%, or at least about 90% identity, and even more preferably at least about 95%, more preferably at least about 97% identical, more preferably at least about 98% identical, more preferably at least about 99% identical, and even more preferably still, entirely identical (i.e., 100% or "invariant").

Likewise, as used herein, the term "substantially identical" encompasses two or more biomolecular sequences (and in particular polynucleotide sequences) that exhibit a high degree of identity to each other at the nucleotide level. For example, in the context of two or more nucleic acid sequences, "substantially identical" can refer to sequences that at least about 80%, and more preferably at least about 85% or at least about 90% identical to each other, and even more preferably at least about 95%, more preferably at least about 97% identical, more preferably at least about 98% identical, more preferably at least about 99% identical, and even more preferably still, entirely identical (i.e., 100% identical or "non-degenerate").

The term "recombinant" indicates that the material (e.g., a polynucleotide or a polypeptide) has been artificially or synthetically (non-naturally) altered by human intervention. The alteration can be performed on the material within or removed from, its natural environment or state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant influenza virus, is produced by the expression of a recombinant nucleic acid.

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. "Operably linked" means that the nucleic acid sequences being linked are typically contiguous, or substantially contiguous, and, where necessary to join two protein coding regions, contiguous and in reading frame. Since enhancers generally function when separated from the promoter by several kilobases and intronic sequences may be of variable lengths; however, some polynucleotide elements may be operably linked but not contiguous.

The phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

The term "pathogen" is defined herein as any sort of infectious agent, including e.g., viruses, prions, protozoans, parasites, as well as microbes such as bacteria, yeast, molds, fungi, protozoa, and the like.

As used herein, the term "plasmid" refers to a genetic construct that is composed of genetic material (i.e., nucleic acids). Typically, a plasmid contains an origin of replication that is functional in bacterial host cells, e.g., *Escherichia coli*, and selectable markers for detecting bacterial host cells including the plasmid. Plasmids of the present invention may include one or more genetic elements as described herein arranged such that an inserted coding sequence can be transcribed and translated in a suitable expression cells. In addition, the plasmid may include one or more nucleic acid segments, genes, promoters, enhancers, activators, multiple cloning regions, or any combination thereof, including segments that are obtained from or derived from one or more natural and/or artificial sources.

The term "a sequence essentially as set forth in SEQ ID NO:X" means that the sequence substantially corresponds to a portion of SEQ ID NO:X and has relatively few nucleotides (or amino acids in the case of polypeptide sequences) that are not identical to, or a biologically functional equivalent of, the nucleotides (or amino acids) of SEQ ID NO:X. The term "biologically functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

Suitable standard hybridization conditions for the present invention include, for example, hybridization in 50% formamide, 5×Denhardts' solution, 5×SSC, 25 mM sodium phosphate, 0.1% SDS and 100 µg/mL of denatured salmon sperm DNA at 42° C. for 16 h followed by 1 hr sequential washes with 0.1×SSC, 0.1% SDS solution at 60° C. to remove the desired amount of background signal. Lower stringency hybridization conditions for the present invention include, for example, hybridization in 35% formamide, 5×Denhardts' solution, 5×SSC, 25 mM sodium phosphate, 0.1% SDS and 100 µg/mL denatured salmon sperm DNA or *E. coli* DNA at 42° C. for 16 h followed by sequential washes with 0.8×SSC, 0.1% SDS at 55° C. Those of skill in the art will recognize that conditions can be readily adjusted to obtain the desired level of stringency.

Naturally, the present invention also encompasses nucleic acid segments that are complementary, essentially complementary, and/or substantially complementary to at least one or more of the specific nucleotide sequences specifically set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present invention may be of any length. By assigning numeric values to a sequence, for example, the first residue is 1, the second residue is 2, etc., an algorithm defining all probes or primers contained within a given sequence can be proposed:

$$n \text{ to } n+y$$

where n is an integer from 1 to the last number of the sequence and y is the length of the probe or primer minus one, where n+y does not exceed the last number of the sequence. Thus, for a 25-basepair probe or primer (i.e., a "25-mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer), exemplary primer or probe sequence include, without limitation, sequences corresponding to bases 1 to 35, bases 2 to 36, bases 3 to 37, bases 4 to 38, and so on over the entire length of the sequence. Likewise, for 40-mers, such probes or primers may correspond to the nucleotides from the first basepair to by 40, from the second by of the sequence to by 41, from the third by to by 42, and so forth, while for 50-mers, such probes or primers may correspond to a nucleotide sequence extending from bp 1 to bp 50, from bp 2 to bp 51, from bp 3 to bp 52, from bp 4 to bp 53, and so forth.

In certain embodiments, it will be advantageous to employ one or more nucleic acid segments of the present invention in combination with an appropriate detectable marker (i.e., a "label,"), such as in the case of employing labeled polynucleotide probes in determining the presence of a given target sequence in a hybridization assay. A wide variety of appropriate indicator compounds and compositions are known in the art for labeling oligonucleotide probes, including, without limitation, fluorescent, radioactive, enzymatic or other ligands, such as avidin/biotin, etc., which are capable of being detected in a suitable assay. In particular embodiments, one may also employ one or more fluorescent labels or an enzyme tag such as urease, alkaline phosphatase or peroxidase, instead of radioactive or other environmentally less-desirable reagents. In the case of enzyme tags, colorimetric, chromogenic, or fluorigenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences. In the case of so-called "multiplexing" assays, where two or more labeled probes are detected either simultaneously or sequentially, it may be desirable to label a first oligonucleotide probe with a first label having a first detection property or parameter (for example, an emission and/or excitation spectral maximum), which also labeled a second oligonucleotide probe with a second label having a second detection property or parameter that is different (i.e., discreet or discernable from the first label. The use of multiplexing assays, particularly in the context of genetic amplification/detection protocols are well-known to those of ordinary skill in the molecular genetic arts.

In general, it is envisioned that one or more of the amplification primers and/or hybridization probes described herein will be useful both as reagents in solution hybridization (e.g., PCR methodologies and the like), and in embodiments employing "solid-phase" analytical protocols and such like.

A number of template-dependent processes are available to amplify the marker sequences present in a given template sample. One of the best-known amplification methods is the polymerase chain reaction (referred to as PCR) which is described in detail in U.S. Pat. Nos. 4,683,195, 4,683,202 and 4,800,159 (each of which is specifically incorporated herein in its entirety by express reference thereto.

Another method for amplification is the ligase chain reaction ("LCR"), disclosed, e.g., in U.S. Pat. No. 4,883,750 (specifically incorporated herein in its entirety by express reference thereto).

An isothermal amplification method, in which restriction endonucleases and ligases are used to achieve the amplification of target molecules that contain nucleotide 5'-[α-thio]- triphosphates in one strand of a restriction site may also be useful in the amplification of nucleic acids in the present invention.

Strand Displacement Amplification (SDA) is another method of carrying out isothermal amplification of nucleic acids that involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Methods based on ligation of two (or more) oligonucleotides in the presence of nucleic acid having the sequence of the resulting "di-oligonucleotide," thereby amplifying the di-oligonucleotide, may also be used in the amplification of the present invention.

Following any amplification, it may be desirable to separate the amplification product from the template and the excess primer for determining whether specific amplification has occurred. In one embodiment, amplification products are separated by agarose, agarose-acrylamide or polyacrylamide gel electrophoresis using conventional methods that are known to those of ordinary skill in the art.

EXAMPLES

The following examples are included to demonstrate illustrative embodiments of the invention. It should be appreciated by those of ordinary skill in the art that the techniques disclosed in the examples that follow represent techniques discovered to function well in the practice of the invention, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the invention.

Example 1

Collection of Biological Samples, Nucleic Acid Extraction and Downstream Molecular Processing In the practice of the invention, oropharyngeal, nasal, tracheal, and/or bronchial, samples of a subject suspected of having a tuberculosis infection are taken, typically in the form of sputum or lavage samples. This example describes the use of PrimeStore® (Longhorn Vaccines & Diagnostics, San Antonio, Tex., USA) (also described in detail in U.S. Patent Appl. Publ. No: 2009/0312285, which is specifically incorporated herein in its entirety by express reference thereto), a clinical or environmental sample collection system specifically formulated for downstream molecular diagnostic testing.

Materials and Methods

Four smear-positive sputum specimens obtained from a sputum bank (University of Pretoria, South Africa) with qualitative grading of +, ++ or +++, as observed by light microscopy, and differing viscosities were collected by having patients expectorate into a specimen cup. Typical expectorate volumes were about 5 mL to about 20 mL of sputum.

about 231 and 281 ng/μL. No significant difference was obtained when comparing the DNA concentration of the control samples with the DNA concentration of the samples obtained by use of the swabs.

TABLE 2

DNA CONCENTRATION OF SPUTUM SAMPLES AFTER COLLECTION AND PRESERVATION IN PRIMESTORE ®

| Specimen | Smear Microscopy Status of Specimen | Quality | Swab Vol. 1 (mL) | Swab Vol. 2 (mL) | Swab Vol. 3 (mL) | Control Vol. (mL) | DNA Concentration (ng/μL) | | |
|---|---|---|---|---|---|---|---|---|---|
| | | | | | | | Control | Swab 1 | Swab 2 | Swab 3 |
| A | + | salivary/bloody | 0.05 | 0.05 | 0.15 | 1.20 | 258.05 | 243.68 | 238.15 | 235.15 |
| B | +++ | purulent | 0.05 | 0.45 | 0.25 | 1.70 | 251.76 | 240.34 | 238.43 | 231.54 |
| C | +++ | purulent | 0.15 | 0.10 | 0.05 | 1.65 | 248.60 | 261.86 | 246.75 | 246.66 |
| D | ++ | purulent/salivary | 0.25 | 0.30 | 0.15 | 17.90 | 258.32 | 281.31 | 241.89 | 246.66 |

Real-time PCR was positive for all specimens, except one in which PCR inhibition occurred.
The results are shown in Table 3 and FIG. 1.

The sputum samples were qualitatively observed as to whether they were bloody, purulent, foamy, frothy or salivary. Samples graded "purulent" were those observed to contain pus, while samples graded "salivary" contained larger amounts of saliva than other components such as mucous. Flocked swabs (Copan Italia S.p.A., Brescia, Italy) were then used to collect small quantities of sputum by rotating the swab five times within each sputum specimen container. Sputum specimens were weighed prior to swabbing and after each swab to estimate the volume of sputum taken. Each swab contained approximately 25 mL to 500 mL of sputum. The individual swabs were transferred to collection tubes, each containing 1.5 mL of the collection and preservation formulation of the present invention ("PrimeStore®"). The swabbing procedure was carried out in triplicate for each sputum specimen. PrimeStore® was also added to the remainder of the sputum specimen at a ratio of 1:1 as a control and then placed at −4° C. until processed. The swabs, suspended in PrimeStore® in each collection tube, were kept at room temperature for approximately twelve hours before a sample was removed for nucleic acid processing by nucleic acid extraction and real-time PCR. DNA was extracted from 100 μL aliquots of the control remaining sputum specimens and swab-tubes using the AMPLICOR® MTB Respiratory Kit (Roche) according to the manufacturer's instructions. All specimens were vortexed at maximum speed for 10 seconds to extract nucleic the acids. DNA concentrations after extraction were measured using a NanoDrop® 1000 spectrophotometer (Thermo Scientific, DE, USA), according to the manufacturer's instructions, and the calculated results are shown in Table 2. Four microliters of the extracted DNA were used for real-time PCR using the LightCycler® *Mycobacterium* Detection Kit (Roche Diagnostics, USA).

Results

PrimeStore® Microbial Inactivation and Preservation of Microbial Nucleic Acid

PrimeStore® was shown to be effective for use in preparing nucleic acids from biological samples for DNA and/or DNA extraction techniques, and downstream molecular analysis. As can be seen in Table 2, the volumes collected after each swabbing ranged from about 0.05 mL to about 0.5 mL. DNA concentration after extraction ranged between

TABLE 3

REAL-TIME PCR RESULTS AFTER IMMERSION IN PRIMESTORE ® AND USE OF THE LIGHTCYCLER ® *MYCOBACTERIUM* DETECTION KIT

| Specimen | $C_T$ Value |
|---|---|
| Positve | 27.28 |
| Negative | — |
| A* | 31.54 |
| A-1 | 32.14 |
| A-2 | 32.75 |
| A-3 | 34.97 |
| B* | 31.56 |
| B-1 | 31.77 |
| B-2 | 32.03 |
| B-3 | 32.14 |
| C* | 23.8 |
| C-1 | 26.62 |
| C-2 | 26.56 |
| C-3 | 26.5 |
| D* | 26.64 |
| D-1 | 29.63 |
| D-2 | inhibition |
| D-3 | 28.95 |

* Remaining specimen (control)
-1/-2/-3 indicates the order of swabbing

Discussion

The swabbing procedure is a useful method for collection of specimens directly from collected sputum specimen for downstream molecular processing. In this study, DNA concentrations after extractions showed similar ranges for both the swabbed and the remaining sputum specimen (control) components. A volume as low as about 50 μL of sputum diluted in 1.5 mL of PrimeStore® was sufficient for PCR analysis. However, in two of the specimens, a delay in Cr value of ~3 logs has been noted. In case of single inhibition, this might be due to residual PrimeStore® solution being present as a result of carry-over from the DNA extraction process to the PCR.

Conclusion

Simple and rapid molecular diagnostic processing directly from PrimeStore® treated swabbed specimens as well as routine conventional testing was conducted from single sputum collections. Molecular processing results from small quantities of smear-positive TB specimens, obtained by swab-transfer to PrimeStore®, is feasible and accurate.

Example 2

Inactivation of Microbes in Tuberculin Samples Using PrimeStore®

Materials and Methods

To evaluate the degree of inactivation of tubercle bacteria within sputum samples when exposed to PrimeStore®, three studies were performed:

In the first study, a known MDR strain of *M. tuberculosis* was grown in MGIT® liquid based system (*Mycobacteria* Growth Indicator Tube, Becton Dickinson, USA). The isolate of the strain was acid-fast (AF) and smear-positive, and multi-drug resistance (MDR) was confirmed using a Line Probe Assay (Hain Lifescience GmbH, Nehreben, Germany). 0.15 mL or 0.5 mL inoculum of the known MDR tuberculosis strain was placed into 1.5 mL of PrimeStore® for either 2 or 10 minutes' incubation. Each solution was then vortexed, and further cultured in the MGIT® liquid based system, according to manufacturer's instructions. A control sample unexposed to PrimeStore® was also placed in the MGIT® liquid culture.

The second study placed known smear-positive sputum samples (>10 acid fast bacillus [AFB]/high-power fields [hpf] each) into 1.5 mL of PrimeStore® for either 1 minute or 5 minutes followed by Auramine O, and Ziehl-Neelsen staining to observe cell wall morphological and integrity.

The third study used $10^5$ to $10^6$ concentration of a reference *mycobacterium* strain, namely H37rv (University of Pretoria, South Africa), to perform a time-kill assay. 0.5 mL inocula of the strain were placed in 1.5 mL of PrimeStore® for either 5 seconds, 10 seconds, 20 seconds, 40 seconds, 80 seconds, or 160 seconds, and then 2 drops of the resulting solutions were each then subcultured onto Middlebrook 7H11 agar (Becton Dickinson, Franklin Lakes, N.J., USA). Control samples unexposed to PrimeStore® were also similarly plated. In one control, 0.5 mL of H37rv strain was placed into 1.5 mL of saline. In another control, 0.5 mL of H37rv inoculum was placed directly onto the Middlebrook 7H11 agar. The plates were kept under ambient conditions for 30 minutes, then sealed, and incubated under aerobic conditions at 37° C. for six weeks. This study was performed in duplicate.

Results

In the first study, no growth was observed in the MGIT® liquid cultures for any of the MDR tubercular samples stored in PrimeStore®, even after 42 days' incubation. The control sample unexposed to PrimeStore® showed positive growth after 9 days. Further extraction and amplification of the two samples that were stored in PrimeStore® demonstrated good banding, and confirmed the stability of the nucleic acid in PrimeStore®.

In the second study, no AFB were observed in any of the PrimeStore®-incubated samples, at either exposure times.

In the third study, no growth was observed after 42 days of incubation at any of the time points. Colony forming units were detected on the control plate after 7 days.

Conclusion

PrimeStore® killed a variety of *M. tuberculosis* strains within a very short period of exposure, thereby confirming PrimeStore® allows for safe and rapid point-of-care collection and transport of biological samples suspected of containing *M. tuberculosis*.

Example 3

Storage, Nucleic Acid Extraction, Molecular Processing of Tuberculin Samples and Diagnosis of Tuberculosis Materials and Methods Sputum samples were processed using the same swabbing technique as described in Example 1, as well as using 1:1 ratios of PrimeStore® to sputum. The sputum samples used in these experiments were obtained from the sputum bank as before, and had been previously classified by both smear microscopy and culture results. All samples were initially characterized for acid fastness (i.e., by either +, ++, or +++ indicators on smear microscopy), and subsequently classified as either positive, negative or scanty for *M. tuberculosis*, by culture.

DNA was extracted from the sputum sample in PrimeStore® at various time points ranging from 6 days to 6 weeks. As shown in Table 4, the specimens in PrimeStore® were kept at ambient temperature for different periods of time before nucleic acid extraction was carried out. Extraction via QiaAmp® DNA Mini kit (Qiagen®, Hilden, Germany), and the MagNA Pure 96™ System (Roche Diagnostics, USA), were each performed according to the manufacturers' instructions. All nucleic acid extracts were kept at −20° C. until processed for amplification.

DNA extracts were amplified by either the LightCycler® *Mycobacterium* detection kit (Roche), or using the prime mix of the present invention, hereinafter referred to as "Prime Mix Universal TB kit," "PrimeMix Universal TB kit," or simply "PrimeMix." Four microliters of extracted nucleic acid solution was used with the Prime Mix Universal TB kit. All of the above systems are real-time PCR platforms with detection of products onboard. Amplification of the Qiagen® extracts was performed in triplicate to determine the reproducibility of the LightCyler® *Mycobacterium* detection kit, and the Prime Mix Universal TB kit.

Results

As can be seen in Table 4, four samples were smear-positive, seven samples were smear-negative and three samples were scanty.

TABLE 4

DURATION OF SPECIMEN IN PRIMESTORE ® PRIOR TO NUCLEIC ACID EXTRACTION

| | Delay before extraction (days) | |
|---|---|---|
| Extraction procedure | Smear-Negative/Scanty | Smear-Positive |
| QiaAmp ® DNA Mini Kit (Qiagen ®) | 6 | 28 |
| MagNA Pure ™ 96 (Roche) | 20 | 42 |

TABLE 5

SMEAR AND REAL-TIME PCR RESULTS ($C_\tau$ VALUES) USING
VARIOUS EXTRACTION KITS FOR SWABBED SPECIMENS

| Specimen No. | Smear | QiaAmp® Extraction/PrimeMix® | | | QiaAmp® Extraction/LightCycler® | | | MagNA Pure™ Extraction/LightCycler® | MagNA Pure™ Extraction/PrimeMix |
|---|---|---|---|---|---|---|---|---|---|
| | | 1 | 2 | 3 | 1 | 2 | 3 | | |
| 1 | + | 35.00 | X | X | X | X | 35.00 | | |
| 4 | ++ | X | X | X | X | X | X | 30.98 | 28.97 |
| 2 | +++ | 32.18 | X | X | 34.19 | X | X | 34.60 | 35.00 |
| 3 | +++ | X | X | X | X | X | X | 27.94 | 27.12 |
| 5 | neg | 35.00 | 35.00 | 35.00 | 34.71 | – | – | – | 35.00 |
| 6 | neg | – | 35.00 | – | – | – | – | – | – |
| 10 | neg | 35.00 | 35.00 | 35.00 | 36.48 | – | 36.20 | – | 35.00 |
| 11 | neg | 32.96 | 32.70 | 32.85 | 35.71 | 35.17 | 33.83 | 35.21 | 35.00 |
| 12 | neg | 34.54 | 35.00 | 34.56 | 34.14 | 34.83 | 34.18 | 33.54 | 35.00 |
| 13 | neg | – | 35.00 | – | – | – | – | – | – |
| 14 | neg | 28.15 | 28.07 | 28.60 | 29.56 | 29.61 | 29.10 | 30.34 | 29.34 |
| 8 | scanty 1 | 32.36 | 32.28 | 32.42 | 34.46 | 34.47 | 35.31 | 34.62 | 35.00 |
| 7 | scanty 7 | 31.79 | 31.73 | 31.83 | 32.10 | 32.79 | 32.08 | 32.70 | 33.53 |
| 9 | scanty 9 | 33.15 | 33.51 | 33.43 | 36.10 | 34.53 | 34.56 | 34.27 | 35.00 |

Summary of Analyzed Results (Number of $C_T$ Values Obtained/Number of Samples Tested)

| | QiaAmp® Extraction/PrimeMix® | | | QiaAmp® Extraction/LightCycler® | | | MagNA Pure™ Extraction/LightCycler® | MagNA Pure™ Extraction/PrimeMix |
|---|---|---|---|---|---|---|---|---|
| Smear | 1 | 2 | 3 | 1 | 2 | 3 | | |
| Smear-positive | 2/2 | X | X | 1/2 | X | X | 3/4 | 4/4 |
| Smear-negative | 5/7 | 7/7 | 5/7 | 5/7 | 3/7 | 4/7 | 3/3 | 5/7 |
| Scanty | 3/3 | 3/3 | 3/3 | 3/3 | 3/3 | 3/3 | 3/3 | 3/3 |

X indicates that the experiment was not conducted;
(–) indicates that the results were negative

TABLE 6

SMEAR AND REAL-TIME PCR RESULTS (CT VALUES)
USING VARIOUS EXTRACTION KITS FOR SPUTUM
SAMPLES IMMERSED IN PRIMESTORE® IN A 1:1 RATIO

| Specimen No. | Smear | MagNA Pure™ Extraction/PrimeMix | MagNA Pure™ Extraction/LightCycler® |
|---|---|---|---|
| 1 | + | 35.00 | 33.02 |
| 2 | +++ | 28.96 | 33.62 |
| 3 | +++ | 23.97 | 25.53 |
| 4 | ++ | 26.30 | 28.27 |
| 5 | neg | 35.00 | 34.00 |
| 6 | neg | — | — |
| 7 | scanty 7 | 30.20 | 30.72 |
| 8 | scanty 1 | 33.59 | 32.85 |
| 9 | scanty 9 | 31.76 | 31.81 |
| 10 | neg | 35.00 | 35.19 |
| 11 | neg | 30.05 | 30.70 |
| 12 | neg | 32.68 | 32.90 |
| 13 | neg | — | — |
| 14 | neg | 26.16 | 26.74 |

(—) indicates no result(s) obtained

Discussion

As can be seen in Table 5, for swabbed sputum samples, DNA extracted using either the QiaAmp® DNA mini kit or the MagNA Pure™ 96 System and then processed using the PrimeMix® of the present invention detected the presence of tuberculosis-causing bacterial DNA when the smear sample indicated a slightly positive result (i.e., "+"), unlike that of the DNA extracted using the QiaAmp® DNA mini kit or the MagNA Pure™ 96 System and then processed using the LightCycler® Mycobacterium detection kit, which did not detect any tuberculosis (TB)-causing bacterial-specific nucleic acids. Importantly, PrimeMix® assays were able to detect tuberculosis-causing bacterial nucleic acids in more smear-negative, culture-positive specimens, than the LightCycler® Mycobacterium kit was able to detect. Tuberculosis-causing bacterial DNAs were equally detected using both PrimeMix® and Lightcycler® procedures, when larger amounts of sputum were analyzed.

Conclusion

Overall the performance of the swabbing technique and use of PrimeStore® have shown consistent results with the use of PrimeMix® in comparison to the varying results for the LightCycler® kit. PrimeStore® has shown compatibility with the different extraction systems and in no cases were inhibition of PCR a reason for a negative result.

Example 4

Compatibility of PrimeStore® with Diagnostic Assays

Materials and Methods

Fifteen smear-positive and fifteen smear-negative sputum samples (as determined by Auramine O staining), were obtained from patients suspected of having pulmonary tuberculosis. The smear-positive samples were tested using the Line Probe Assay, followed by culture. The smear-negative samples were also cultured. All raw sputum samples were generally then liquefied, decontaminated and concentrated using the NaLc/NaOH ("DTT/NaOH") procedure, as would be known to one of ordinary skill in the art and as described in Kubica, G. P., et al. (1963) *Sputum Digesting and Decontamination with N-acetyl-L-cysteine as a Sputum Digestant for the Isolation of Mycobacteria*, Amer. Rev. Resp. Dis.; 89:284-286 and Kubica, G. P., et al. (1963) *Sputum Digesting and*

*Decontamination with N-acetyl-L-cysteine-sodium hydroxide for Culture of Mycobacteria*, Amer. Rev. Resp. Dis.; 87:775-779, the entire contents of which are incorporated by express reference thereto. In general the NaLc/NaOH procedure is used prior to culture methods and nucleic acid testing for *M. tuberculosis*. Aliquots of 0.5 mL of the NaCl/NaOH treated sputum samples were then added to PrimeStore® and stored overnight. A control was also used wherein aliquots of 0.5 mL of the NaCl/NaOH treated sputum samples were not added to PrimeStore®. Extraction was performed via AMPLICOR® Respiratory Specimen Preparation Kit (Roche). Two commercial assays, the LightCycler® *Mycobacterium* Detection kit (Roche) and the Genotype MTBDRplus (Hain Lifesciences GmbH) were used to detect the presence or absence of *M. tuberculosis*-specific nucleic acids. The Genotype MTBDRplus assay was found compatible with the use of PrimeStore® contacting raw sputum samples and drug resistant TB strains were detected in these samples using this assay.

Results

Table 7 demonstrates the results obtained with the LightCycler® *Mycobacterium* Detection kit (LC).

TABLE 7

SUITABILITY OF PRIMESTORE ® FOR MOLECULAR TESTING AFTER DECONTAMINATION

|  | sm+ | sm− |
|---|---|---|
| DTT/NaOH—No PS | | |
| LC pos | 13 | 0 |
| LC neg | 2 | 15 |
|  | 15 | 15 |
| DTT/NaOH—with PS | | |
| LC pos | 13 | 1 |
| LC neg | 2 | 14 |
|  | 15 | 15 |

Discussion and Conclusion

As can be seen in Table 7, after storage in PrimeStore®, the LightCycler® assay tested positive for *M. tuberculosis* in a smear negative sample, which was not obtained when PrimeStore® was not used. Thus, PrimeStore® may have a higher ability to detect lower quantities of *M. tuberculosis*. Otherwise, the results obtained were comparable, and thus PrimeStore® is compatible with commercially-available detection assays.

Example 5

Sensitivity of Detection of *M. Tuberculosis* After Storage in PrimeStore®

Materials and Methods

Seven smear-negative, culture-positive specimens, and three scanty specimens (SC1, SC7 and SC9) from a sputum bank (University of Pretoria, South Africa) were included in this evaluation. Flocked swabs (Copan) were used to collect small quantities of sputum by rotating the swab within each sputum specimen (500 µL in cryovial). The individual swabs were transferred to PrimeStore® collection tubes, each containing 1.2 mL PrimeStore® solution. Sputum specimens were weighed prior to swabbing, and after each swab to estimate the volume of sputum removed from the specimen. PrimeStore® solution was also added to the remainder of the sputum specimen at a ratio of 1:1 as a control. The swabs, suspended in PrimeStore® solution in each collection tube, were kept at room temperature for approximately twelve hours before processing by real-time PCR. DNA was extracted from the remaining sputum specimen (control) and swab-tubes using the AMPLICOR® Respiratory Specimen Preparation Kit. Sputum specimens obtained from the same cultures were also processed according to conventional NaLc/NaOH procedures, and extracted using the AMPLICOR® protocol. An additional extraction method using the Invitrogen™ iPrep™ Purelink™ Virus Kit (Carlsbad, Calif., USA) from raw sputum was also evaluated from these specimens. All specimens were vortexed at maximum speed for 10 seconds and a 100-µL aliquot used for the extraction procedure. DNA concentrations after extraction were determined using the NanoDrop® 1000 instrument. Four microliters of the extracted DNA were used for real-time PCR using the LightCycler® *Mycobacterium* detection kit.

Results

As can be seen in Table 8, the volumes collected after each swabbing ranged from about 0.05 mL to about 0.1 mL. DNA concentration after extraction ranged between about 205 to about 706 ng/µL for the swab, PrimeStore® (1:1) and NaLc/NaOH specimen. Raw sputum extracted from the Invitrogen™ iPrep™ Purelink™ Virus Kit (Carlsbad, Calif., USA) had DNA concentrations ranging from about 7.0 to about 22.6 ng/µL.

TABLE 8

SPUTUM CHARACTERIZATIONS, ESTIMATED SWAB VOLUMES AND DNA CONCENTRATIONS AFTER EXTRACTIONS

| | | | | | | DNA concentration after extraction (ng/µL) | | | |
|---|---|---|---|---|---|---|---|---|---|
| Smear | Culture | Aliquot (500 µL) mg | Aliquot Final mg | Swab vol µL | Remaining Aliquot vol µL | Invitrogen ™ Kit for Extraction of Raw Sputum | PrimeStore ® + swab; Extraction by AMPLICOR ® | PrimeStore ® (1:1)*; Extraction by AMPLICOR ® | DDT/NaOH; Extraction by AMPLICOR ® |
| neg | pos | 300 | 295 | 50 | 450 | 16.8 | 222.9 | 213.8 | 211.7 |
| neg | pos | 305 | 300 | 50 | 450 | 22.6 | 221.6 | 284.4 | 223.4 |
| neg | pos | 305 | 295 | 100 | 400 | 9.9 | 205.7 | 706.4 | 412.7 |
| neg | pos | 305 | 300 | 50 | 450 | 10.9 | 206.9 | 231.7 | 214.9 |
| neg | pos | 310 | 305 | 50 | 450 | 20.4 | 212.9 | 277.2 | 219.3 |
| neg | pos | 250 | 240 | 100 | 400 | 7 | 255.7 | 267 | 239.4 |
| neg | pos | 260 | 250 | 100 | 400 | 9.3 | 226.6 | 276.1 | 217.1 |
| scanty 1 | pos | 300 | 295 | 50 | 450 | 12.7 | 224.9 | 273.4 | 208.7 |
| scanty 7 | pos | 260 | 245 | 50 | 450 | 13.1 | 216.2 | 243.3 | 225.7 |
| scanty 9 | pos | 295 | 290 | 50 | 450 | 6.8 | 222.7 | 233.4 | 225.6 |

*1:1 is the ratio of PrimeStore to clinical sputum sample

Figure 2:
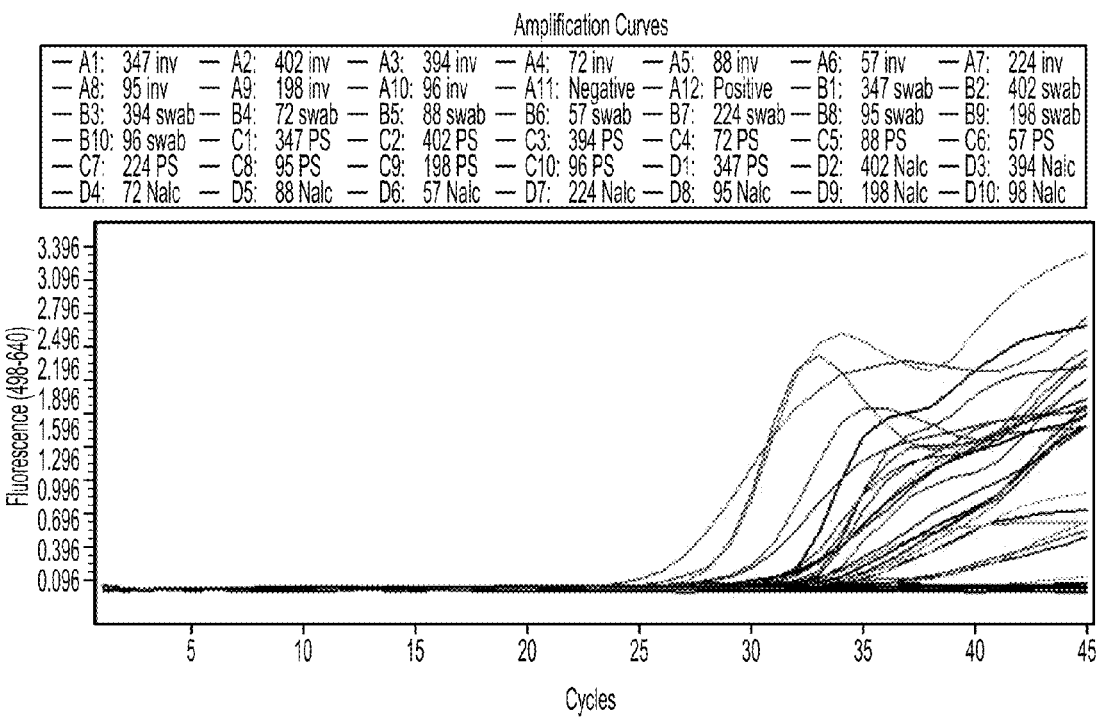
FIG. 2 illustrates the real time (RT) PCR analysis of tuberculin DNA from seven smear negative, culture positive sputum specimens and three scanty, i.e., positive smears results in which the stain was barely visible on the slide, specimen swabs preserved in PrimeStore®. DNA was extracted using the AMPLICOR® Respiratory Specimen Preparation Kit and Invitrogen™ iPrep™ Purelink™ Virus Kit (Carlsbad, Calif., USA), according to the manufacturer's instructions. The LightCycler® *Mycobacterium* detection kit was used, according to the manufacturer's instructions. The resulting Cτ values for each of the samples is shown in Table 8.

Real-time PCR results can be seen in Table 9 and FIG. 2.

TABLE 9

REAL-TIME PCR RESULTS FOR SAMPLES USING THE LIGHTCYCLER ® *MYCOBACTERIUM* DETECTION KIT

| Sputum Bank Number | Smear | Culture | ID | PCR $C_T$ Values | | | |
| --- | --- | --- | --- | --- | --- | --- | --- |
| | | | | Invitrogen ™ Extraction of Raw Sputum | PrimeStore ® swab; Extraction by AMPLICOR ® | PrimeStore ® (1:1); Extraction by AMPLICOR ® | DDT/NaOH; Extraction by AMPLICOR ® |
| 57 | neg | pos | MTB | 35.33 | — | — | — |
| 95 | neg | pos | MTB | 32.12 | 39.49 | 32 | 34.79 |
| 96 | neg | pos | MTB | 27.41 | 29.26 | 37.75 | 26.24 |
| 198 | neg | pos | MTB | — | — | — | — |
| 224 | neg | pas | MTB | 30.77 | 33.28 | 31.87 | — |
| 347 | neg | pos | MTB | — | 37.45 | 33.03 | — |
| 402 | neg | pos | MTB | — | — | — | — |
| 72 | scanty 1 | pos | MTB | 34.3 | — | 32.11 | 34.25 |
| 394 | scanty 7 | pos | MTB | 31.9 | 34.09 | 29.51 | 31.59 |
| 88 | scanty 9 | pos | MTB | 31.9 | — | 31.01 | 32.51 |

(—) symbol indicates that no results were obtained.

No amplification was seen in two of the scanty specimens, i.e., scanty 1 and scanty 9, for the swab specimens. A 100% increase in sensitivity for smear-negative, culture-positive samples was observed when using PrimeStore® in a 1:1 ratio or by swabbing in comparison to the conventional NaLc/NaOH methodology. In fact, the use of PrimeStore®, either by swabbing or in a 1:1 ratio, resulted in the detection of two additional smear-negative, culture-positive samples when compared to that of the conventional NaLc/NaOH methodology. In general, Invitrogen™'s kit is more effective than that of AMPLTCOR®, therefore any variations between PrimeStore® data and that obtained by using Invitrogen™ could be explained by this discrepancy.

Example 6

PrimeStore®Formulations Containing IPCs

This example describes the use of non-specific exogenous internal positive control (IPC) polynucleotides for tracking the integrity of a specimen from the point of collection to molecular analysis using the PrimeStore® (Longhorn Vaccines & Diagnostics, San Antonio, Tex., USA) collection system.

Materials and Methods

Microbe Killing

Membrane Filtration Technique for Bacterial and Fungal Recovery

The membrane filtration method for bacterial and fungal recovery was used to assess the killing ability of PrimeStore®. *Escherichia coli, Pseudomonas aeruginosa, Staphylococcus aureus* [non-methicillin-resistant *Staphylococcus aureus* (MRSA)], *Candida albicans, Bacillus subtilis*, and *Aspergillus brasiliensis* were used to determine whether PrimeStore® could effectively kill and inactivate a panel of bacteria and mould (yeast and filamentous fungi). Positive controls incubated in a water matrix were performed on day 0 only. A population of $1\times10^6$ c.f.u. for each bacterial strain was inoculated into 0.5 mL PrimeStore® for each time-point and subsequently incubated at 20-25° C. The containers were enumerated and evaluated at days 0, 1, 7, 14 and 28. The inoculum was aseptically passed through a sterile filtration device and subsequently rinsed three times with 100 mL sterile neutralizing fluid D [1 g peptic digest of animal tissue (peptone) and 1 mL polysorbate 80 dissolved in 1.0 l of sterile water (final pH 7.1±0.2)]. Where necessary, dilutions of the inoculated test article were performed to deliver a target count of 25-250 c.f.u. per filter. For each time-point, inoculated negative controls were processed in a similar fashion. Filters inoculated with samples containing bacteria were plated onto tryptic soy agar (TSAP) with lecithin and polysorbate 80 and incubated at 30-35° C. for 72 hr. Filters inoculated with samples containing yeast or mould were plated onto Sabouraud dextrose agar (SAB) and incubated at 20-25° C. for no less than 72 hr but no more than 5 days. Colonies were counted to calculate $\log_{10}$ recoveries and percent (%) kill for each organism used during microbial challenge.

MRSA Killing

A stock plate containing about $10^8$ cfu MRSA (ATCC 33592) was transferred to TSB, vortexed briefly and incubated at ambient temperature for 10 min. A total of 0.1 mL bacterial suspension was transferred to 0.9 mL PrimeStore® and vortexed for 60 sec. A total of 0.1 mL suspension was transferred to 0.3 mL TSB (1:4 dilution) and 100 μL was transferred to blood agar plates (5% sheep RBCs in TSA) after 0, 5 and 15 min. Positive controls included equivalent volumes of MRSA and TSB. Plates were allowed to dry, incubated overnight at 37° C. and analyzed for cfu/mL.

Results

PrimeStore® Microbial and Viral Inactivation

Microbial Inactivation

PrimeStore® was shown to rapidly inactivate microbes including fungi, Gram-positive and Gram-negative bacteria, and viruses. Antimicrobial effectiveness testing was performed using the membrane filtration technique for the quantitation of bacteria and fungi. At the first test period (24 hr), 100% of bacteria and fungi were killed compared to the positive controls. For these microbes, PrimeStore® met the inactivation criteria as described in USP Category 1 products (injections, emulsions, optic products, sterile nasal products, and ophthalmic products made with aqueous bases or vehicles). Additionally *Bacillus subtilis* spores were challenged using the method described in USP 51 to further evaluate PrimeStore® inactivation of microbial populations. *B. subtilis* spores were reduced by 99% within 24 hr of exposure. In a time-kill study of MRSA inoculated into PrimeStore®, viable bacteria were not detected (100% killing) at the earliest study time (5 min post-inoculation) or at any of the later evaluation times. Data also demonstrated that PrimeStore® rapidly kills *M. tuberculosis* from clinical sputum samples.

Discussion

In illustrative embodiments, a unique IPC ssRNA has been described that can be added in advance (e.g., about $3\times10^5$ target copies/0.5 mL) to PrimeStore®, and used as an internal control to verify sample stability from the time of sample collection through extraction and detection. Additionally, the IPC ssRNA is useful as a carrier species (particularly for samples containing very low levels of target nucleic acids), and serves as a control for monitoring the integrity, efficiency, and fidelity of the nucleic acid extraction process from the point of collection to nucleic acid analysis. Exemplary IPCs suitable for formulation in PrimeStore® include, without limitation, exogenous and/or synthetically-produced (in vitro) ssDNAs or ssRNAs, and preferably include those polymers that are non-homologous (e.g., as determined by BLAST computer-based analyses) to polynucleotide sequences founds in the mammalian host or the one or more pathogens or normal bacterial flora contained therein.

PrimeStore® has been shown to facilitate standard sequencing and meta-genomic analysis of original clinical samples by improving the quality of target microbial nucleic acids in the originally-collected specimens, even when they arrive at the analytical laboratory hours, or even days later, including those stored and/or transported under less-than-ideal, or even ambient environmental conditions. Recovery of RT PCR amplification fragments over 1400 bases has been observed from viral RNA preserved and shipped in PrimeStore® at ambient temperature for several weeks. In harsh conditions, i.e., 38° C. incubation, RT-PCR amplification of 574-bp and 825-bp fragments were observed from PrimeStore® preserved virus where no amplification was observed from stock virus in commercial VTM.

Importantly, PrimeStore® has been demonstrated to be compatible with many commercial nucleic acid extraction kits. Nucleic acids are extracted directly from PrimeStore® according to standard manufacturer's protocol with only minor differences noted in $C_\tau$ values between column- or bead-based kits. Moreover, PrimeStore® received FDA-Emergency Use Authorization as part of the complete Longhorn Influenza A/H1N1-09 Prime RRT-PCR Assay™. PrinaeStore® is the first molecular transport medium to receive EUA FDA approval, and the first to contain an IPC to control for monitoring specimen degradation from collection to detection.

Example 7

PrimeStore® for Extended Preservation of Microbial Samples and RNA Isolates

This example demonstrates the usefulness in PrimeStore® formulations to inactivate pathogenic organisms, yet retain long-term storage and retention of RNA isolated from such inactivated organisms. As an exemplary embodiment, PrimeStore® was used to collect biological samples containing A/Vietnam/1203/2004 (H5N1) influenza virus. Results demonstrated that the formulation not only inactivated H5N1 and A/Mexico/4108/09 (H1N1, clinical isolate) virus in collected samples, but also preserved the microbial RNA for subsequent PCR analysis. The study demonstrated the lack of cytopathic effects (CPE) or CPE-like reactions of PrimeStore® reagent (1:100 dilution) to Madin-Darby canine kidney cell monolayers, the efficacy of PrimeStore® to inactivate viable H5N1 virus ($1.26\times10^7$ TCID$_{50}$), and the ability of PrimeStore® to preserve viral RNA from H5N1 and H1N1 for up to 62 days in ambient conditions for real-time PCR analysis that resulted in the detection of an abundance of RNA product.

Part 1 of the study comprised of two sections: (1) In vitro toxicity assessment of PrimeStore® reagent on Madin-Darby canine kidney (MDCK) epithelial cells and (2) efficacy of inactivation testing of PrimeStore® reagent against H5N1. Part 2 of the study assessed the quality of the H5N1 and H1N1 RNA that had been impacted as a direct result of the influenza virus' long-term storage in PrimeStore®.

The in vitro toxicity assessment of Part 1 was performed by loading sample collection swabs in triplicate with 0.1-mL viral storage buffer (complete cell culture medium or Minimal Essential Media+10% fetal bovine serum), placed into 5-mL tubes that contained 1.5 mL PrimeStore® and incubated at room temperature (ambient) for 10, 30, or 60 minutes. Following incubation, the swabs were processed using two methods: (1) An aliquot from the viral storage buffer+PrimeStore® sample was removed and serially diluted (10-fold) to $10^{40}$ in complete cell culture media in a 96-well plate that contained a monolayer of MDCK cells. The cells were allowed to incubate for up to 96 hours and then visually examined for the presence of cytopathic effects (CPE) and the dilution that exhibited no observable CPE determined. (2) Each of the viral storage buffer-loaded swabs were removed from PrimeStore® and placed in a 50-mL conical tube that contained 10 mL complete cell culture medium. The swabs were agitated at 200 rpm for 15 min, and an aliquot of each extract was removed and serially diluted (10-fold) in complete cell culture media in a 96-well plate that contained a monolayer of MDCK cells. The cells were allowed to incubate for up to 96 hours and then visually examined for the presence of CPE and the dilution that exhibited no observable CPE determined.

Efficacy of inactivation of Part 1 was conducted based on the results from the in vitro toxicity assessment. Sample collection swabs (n=6) were loaded with 0.1 mL H5N1 (1-5× $10^7$ TCID$_{50}$/mL) or viral storage buffer (negative controls, n=3), placed into 5-mL tubes that contained 1.5 mL PrimeStore® and incubated in ambient conditions for 10, 30, or 60 min Following incubation, the swabs were processed using the most appropriate approach determined from the in vitro toxicity testing. The cells were allowed to incubate for up to 96 hours and then visually examined for the presence of cytopathic effects (CPE) and total TCID$_{50}$ determined Inactivation efficacy was calculated in terms of a log reduction compared to the untreated controls.

The extended ambient storage study for Part 2 involved the preservation of H5N1 and H1N1 RNA in PrimeStore® for up to 62 days at room temperature. The time-points were at Day 0 (day of H5N1 inoculation into the PrimeStore®), +1, +2, +5, +7, +14, +30, and +62 days from the date of inoculation. The H5N1 and H1N1 viruses were diluted to $1\times10^5$ TCID$_{50}$ prior to inoculation into PrimeStore®. At each time-point, RNA isolations using the RNAqueous-Micro Kit (Ambion Cat. No. AM1931, Austin, Tex., USA) were performed on both H5N1 and H1N1 samples stored in PrimeStore®. The resulting RNA were stored at <−80° C. until all of the time-points' RNA were isolated. Real-time PCR was performed on an Applied Biosystems (Forster City, Calif., USA) 7900HT (Fast Real-Time PCR System).

The first method used in the in vitro toxicity assessment of Part 1 (an aliquot from the viral storage buffer+PrimeStore® sample was removed and serially diluted then added to a 96-well plate) resulted in the observation of CPE or CPE-like reaction in the IVIDCK cell monolayer at 1:10,000 for all time-points (10, 30, and 60 min). The second method used in the in vitro toxicity assessment of Part 1 (each of the viral storage buffer-loaded swabs were removed from PrimeStore® and placed in a 50-mL conical tube that contained 10 mL complete cell culture medium, the swabs were agitated for 15 min, and an aliquot of each extract was removed and serially diluted) resulted in the observation of CPE or CPE-like reaction in the MDCK cell monolayer at 1:100 for all time-points. Therefore, the in vitro toxicity assessment of Part 1 determined that the second method of sample extraction resulted in CPE or CPE-like reaction to the MDCK cells by PrimeStore®, and this second method was deemed suitable for efficacy of inactivation testing of Part 1. The 60-min time point (i.e., the longest time point recorded) was chosen for the efficacy test since it did not determine whether CPE or CPE-like reactions corresponded with any time-point. The CPE or CPE-like reactions for the longest time-point were equivalent to the shortest time-point (10 min), this clearly demonstrated that CPE or CPE-like reactions were dilution (1:100)—and extraction method (second method)-dependent.

The efficacy of inactivation testing of Part 1 resulted in no detectable, viable H5N1 since the virus recovery was equivalent to the negative control (i.e., PrimeStore® with no virus added). Whereas, the positive control (i.e., no PrimeStore® added, cell culture media used in lieu of PrimeStore® reagent, virus added) resulted in excellent recovery (67.59% average recovery) of H5N1 as expected. The results indicate that PrimeStore® reagent was capable of inactivating a high titer of H5N1 ($1.26\times10^7$ $TCID_{50}$) at 60 min down to the level of the negative control.

The real-time PCR from the extended ambient storage study for Part 2 showed that target detection to all four assays (BBRC H1N1, BBRC H5N1, Longhorn H1N1, and Longhorn H5N1) from the RNA extracted from the longest time-point at 62 days proved to be just as sensitive (all average $C_\tau$<26.00) as the shortest time-point at Day 0 (day of inoculation). The results indicate that PrimeStore® reagent did not have deleterious effects on the RNA during extended storage durations in ambient conditions.

Example 8

Analysis of Specimens Containing Mycrobacterial-Specific Nucleic Acids

Materials and Methods

Genomic Primer/Probe Design:

Universal species-specific assays target a highly conserved region of the IS6110 gene, an insertion element found almost exclusively within the members of the *Mycobacterium tuberculosis* complex. Multiple copies of the IS6110 element can be found at differing locations in the genomes of the members of the *M. tuberculosis* complex, so these primers can also aid in genotyping strains. All primers and probes were procured from Applied Biosystems (Foster City, Calif., USA).

Real-Time PCR Platforms:

The laboratory-based LightCycler® 2.0 instrument (Roche Molecular Diagnostics, Indianapolis, Ind., USA), and its lightweight portable (50-lb) version, the Ruggedized Advanced Pathogen Identification Device (R.A.P.I.D., Idaho Technologies, Salt Lake City, Utah, USA), are both 32-well capillary, real-time instruments which employ similar components and operational software. The R.A.P.I.D, is configured within a hardened case, and can be employed remotely (e.g., in the field, or at the point-of-care).

Real-Time PCR Amplification:

Primer and probe sequences are shown above. Primer pair melting points are within 2° C. and anneal/extend at 58-60° C. The respective probes anneal/extend 8-10° C. higher than that of the primers. Thermocycling operates in a rapid, 2-temperature format with annealing and extension, each at 60° C. for at least about 30 seconds total, facilitated by the short nature of the respective amplicons.

Real-time amplification was performed in a single-step, single-reaction-vessel format. Using the PrimeMix® Universal MTB Assay (Longhorn Vaccines & Diagnostics, USA), either 2 μL, 3 μL, 4 μL or 5 μL of nucleic acids was added to either 18 μL, 17 μL, 16 μL or 15 μL, respectively, of master mix (i.e., PrimeMix®) containing the following components at the indicated final concentrations: (a) 1× reaction buffer containing 50 mM of Tris, pH8.0, 70 mM of KCl, 3 mM of $MgSO_4$, 45 mM of Betaine, 0.05 μM of ROX™, 0.025 μg/μL of ultra pure BSA, 0.2 mM of dNTPs, and 0.1 mM of EDTA; (b) 1× enzyme mixture containing 20 μM of each primer, 1 unit of Taq polymerase, and 20 μM labeled probe. The forward primer for amplifying the *M. tuberculosis* target sequence consisted of the following sequence: 5'-CTCGTCCAGCGCCGCTTC-3' (SEQ ID NO:2). The reverse primer for amplifying the *M. tuberculosis* target sequence consisted of the following sequence: 5'-ACAAAGGCCACGTAGGCGA-3' (SEQ ID NO:3). The labeled probe for detecting the presence of the *M. tuberculosis* target sequence consisted of the following sequence: 5'-6FAM-ACCAGCACCTAACCGGCTGTGGGTA-MGBNFQ-3' (SEQ ID NO:4). FIG. 5 shows that the addition of more template *M. tuberculosis* DNA, i.e., 5 μL rather than 2 μL of extracted patient DNA, results in slightly better RT-PCR amplification and detection results, i.e., an average Cr value of 25.1 for 2 μL versus an average Cτ value of 23.4 for 5 μL.

Thermocycling was performed as follows: an initial hot-start at 95° C. for 5 min, followed with 40 cycles of denaturation at 95° C. for 10 sec, and a combined annealing and extension at 60° C. for 32 sec. Amplification efficiency was determined using the Cτ slope method according to the equation: $E=[10^{(-1/Slope)}-1]\times100$. All assays described here exhibited greater than 98.5% amplification efficiency.

For each analysis, 'no template' and 'positive' controls were included. Baseline fluorescence for each analysis was manually adjusted to that of the respective 'no template' control reaction. The 'positive' control gives rise to an increase in fluorescence intensity relative to the no template baseline. A 'positive' unknown is defined as amplification exceeding baseline fluorescence with a corresponding Cτ value not exceeding 36 in a 40-cycle run.

Evaluation of the PrimeMix® Universal MTB Assay:

Samples were collected by swirling a Copan swab five times around a sputum specimen and immersed in a PrimeStore® collection tube containing 1.5 mL of PrimeStore® solution. A 1:1 ratio of sample to PrimeStore® was also used, as described above. Prior to this evaluation the swabbed material was extracted using the AMPLICOR® Respiratory Specimen Preparation Kit and amplified using the LightCycler® *Mycobacterium* Detection Kit. The specimens were kept at ambient temperatures for approximately 6-30 days prior to nucleic acid extraction and amplification using the PrimeMix™ Universal MTB Assay as described above. The PrimeMix™ Universal MTB Assay was shipped to the lab from the United States at 4° C. (4 days) and once received remained at ambient temperature for 48 hours before being stored at −20° C.

Nucleic acid extraction was carried out using the QIAamp® DNA Mini Kit (Qiagen®, Hilden, Germany) according to manufactures' instructions. 200 µl of the swabbed material in PrimeStore® was vortexed briefly (e.g., 5 to 10 sec) and used as starting material for the extraction procedure.

Nucleic acid amplification was carried out using the PrimeMix™ Universal MTB Assay. The forward primer for amplifying the M. tuberculosis target sequence consisted of the following sequence: 5'-CTCGTCCAGCGCCGCTTC-3' (SEQ ID NO:2). The reverse primer for amplifying the M. tuberculosis target sequence consisted of the following sequence: 5'-ACAAAGGCCACGTAGGCGA-3' (SEQ ID NO:3). The labeled probe for detecting the presence of the M. tuberculosis target sequence consisted of the following sequence: 5'-6FAM-ACCAGCACCTAACCGGCT-GTGGGTA-MGBNFQ-3' (SEQ ID NO:4). The PCR reaction contained 18 µl of PrimeMix™ Universal MTB and 2 µL of extracted nucleic acids. The amplification profile consisted of an initial hot-start at 95° C. for 5 min, followed with 40 cycles of denaturation at 95° C. for 10 sec and a combined annealing and extension at 60° C. for 32 sec, as described above. Amplification was carried out on the LightCycler® 480 platform (Roche) and the amplicon was detected due to FAM labeling of the probe.

Similar to the Examples described above, comparative studies were performed using the following protocols: (1) NaLc/NaOH decontamination procedure followed by extraction by use of the AMPLICOR® Respiratory Specimen Preparation Kit and amplification using the LightCycler® Mycobacterium Detection (MTB) kit; (2) the swabbing procedure of the culture into PrimeStore®, followed by extraction by use of the AMPLICOR® Respiratory Specimen Preparation Kit and amplification using the LightCycler® MTB kit; (3) a 1:1 ratio of specimen to PrimeStore®, followed by extraction by use of the AMPLICOR® Respiratory Specimen Preparation Kit and amplification using the LightCycler® MTB kit; (4) the swabbing procedure of the culture into PrimeStore®, followed by extraction by use of the AMPLICOR® Respiratory Specimen Preparation Kit and amplification using the PrimeMix® Universal MTB Assay; and (5) the swabbing procedure of the culture into PrimeStore®, followed by extraction by use of the QIAamp® DNA Mini Kit and amplification using the LightCycler® MTB kit.

Results and Conclusion

Results of the PrimeMix® Universal MTB Assay can be seen in Tables 10 and 11 below:

TABLE 10

SPECIMEN INFORMATION

| Specimen No. | Smear | Culture ID | Volume of specimen on swab (µL) | Duration (days) of swab sample in PrimeStore ® at ambient temp prior to amplification |
|---|---|---|---|---|
| 1 | + | M. tuberculosis | 50 | 28 |
| 2 | +++ | M. tuberculosis | 50 | 28 |
| 3 | +++ | M. tuberculosis | 150 | 28 |
| 4 | ++ | M. tuberculosis | 250 | 28 |
| 5 | Negative | M. tuberculosis | 100 | 6 |
| 6 | Negative | M. tuberculosis | 100 | 6 |
| 7 | Scanty 7 | M. tuberculosis | 50 | 6 |
| 8 | Scanty 1 | M. tuberculosis | 50 | 6 |
| 9 | Scanty 9 | M. tuberculosis | 50 | 6 |
| 10 | Negative | M. tuberculosis | 50 | 6 |
| 11 | Negative | M. tuberculosis | 50 | 6 |
| 12 | Negative | M. tuberculosis | 50 | 6 |
| 13 | Negative | M. tuberculosis | 50 | 6 |
| 14 | Negative | M. tuberculosis | 100 | 6 |

TABLE 11

COMPARISON OF PCR RESULTS USING DIFFERENT PROCESSING METHODS

| Specimen No. | Smear | NaLc/NaOH; LightCycler® MTB Kit $C_t$ VALUES | Swab in PrimeStore ®; LightCycler ® MTB Kit $C_t$ VALUES | Specimen to PrimeStore ® 1:1 LightCycler ® MTB Kit $C_t$ VALUES | Swab in PrimeStore ®; PrimeMix ® Universal MTB Assay $C_t$ VALUES | Swab in PrimeStore ®; Qiagen ®; LightCycler ® MTB Kit $C_t$ VALUES |
|---|---|---|---|---|---|---|
| 1 | + | 27.00 | 31.34 | 31.54 | 35.00 | 31.67 |
| 2 | +++ | 28.82 | 31.77 | 31.56 | 33.43 | 32.74 |
| 3 | +++ | 29.21 | 26.62 | 23.80 | 26.24 | 26.56 |
| 4 | ++ | 28.04 | 29.63 | 26.64 | 27.51 | 28.96 |
| 5 | neg | — | 37.45 | 33.03 | 35.00 | 33.11 |
| 6 | neg | — | — | — | — | — |
| 7 | scanty 7 | 34.25 | 34.09 | 29.51 | 33.03 | 31.85 |
| 8 | scanty 1 | 31.59 | — | 32.11 | 35.00 | 34.21 |
| 9 | scanty 9 | 32.51 | — | 31.01 | 35.00 | 33.75 |
| 10 | neg | — | — | — | 35.00 | 33.89 |
| 11 | neg | — | 33.28 | 31.87 | 35.00 | 33.59 |
| 12 | neg | 34.79 | 39.49 | 32.00 | 35.00 | 32.72 |
| 13 | neg | — | — | — | — | 34.47 |
| 14 | nee | 26.24 | 29.26 | 37.75 | 35.00 | 29.19 |

(—) symbol indicates that no results were obtained.

The PrimeMix™ Universal MTB Assay detected 71% of the smear negative cases as well as a 100% of the smear positive ones. The PrimeMix™ Universal MTB Assay detected a higher number of culture positive samples than use of the LightCycler® MTB. The PrimeMix™ Universal MTB Assay was compatible with the use of the PrimeStore® solution.

Example 9

Stability of the PrimeMix® Universal MTB Assay

Materials and Methods

PrimeMix® Universal MTB Assay components as described above were removed from storage in −20° C. temperature and placed at room temperature a varying number of times, i.e., one, three, five and ten times, to determine the stability of the combined reagents and whether repeated thawing and freezing would inhibit the performance of the PrimeMix® Universal MTB Assay in detecting *M. tuberculosis* complex in nucleic acid samples. All of the assay components in a single tube and were thawed at room temperature for about three to about five minutes. The tube was then placed in −20° C. temperature for about one hour to start the next freeze-thaw cycle. After the final freeze-thaw cycle, RT-PCR was carried out as described above for the PrimeMix® Universal MTB Assay using a previously-identified MDR-TB strain (University of Pretoria, South Africa). Experiments were carried out in triplicate for each number of freeze-thaw cycles and the resulting $C_\tau$ values were averaged.

Results and Conclusion

Figure 3:
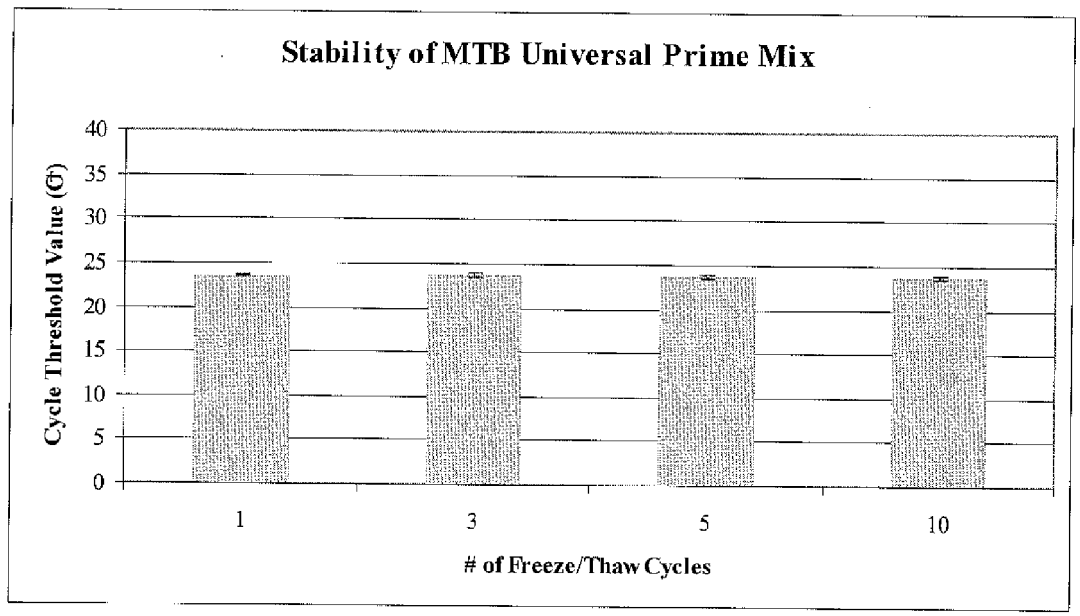
FIG. 3 shows a graph of the RT-PCR analysis of Prime-Mix® Universal MTB Assay components that were removed from storage in −20° C. temperature and placed at room temperature a varying number of times, i.e., one, three, five and ten times and then used in the PrimeMix® Universal MTB Assay.

Results of the PrimeMix® Universal MTB Assay after being placed in a number of freeze/thaw cycles can be seen in FIG. 3. As can be seen from this graph, the PrimeMix® Universal MTB Assay showed no reduction in PCR amplification, as indicated by the resulting $C_\tau$ values, which do not vary significantly from one another, even when the PrimeMix® Universal MTB Assay components are thawed and re-frozen ten times. The average $C\tau$ values after one freeze-thaw cycle ($C_\tau$=23.6) and after ten freeze-thaw cycles ($C_\tau$=23.7) did not vary significantly. Thus, the PrimeMix® Universal MTB Assay contains stable components which do not degrade under varying temperature conditions making it particularly suitable for use in the field, away from traditional laboratory settings.

Example 10

Detection of ICP(s) to Monitor Sample Integrity/Nucleic Acid Fidelity in PrimeMix Assays Design of Internal Positive Control to be Placed into PrimeStore®, Along with Primers and Probes to Detect the Same As noted herein, in certain embodiments it is desirable to include a nucleic acid carrier molecule and/or an IPC sequence to aid in preparation, stabilization, and quantitation of the isolated polynucleotides. The IPCs of the invention may be directly chemically synthesized using conventional methods, or alternatively, prepared using recombinant DNA technology. It is desirable to formulate an IPC sequence that is both non-genomic, and that does not significantly hybridize to a mammalian genome, or to the genome of pathogenic species of interest. Particular compositions and methods of use can be found in Applicant's co-pending U.S. Patent Appl. Publ. No. 2009/0233309 (filed Apr. 20, 2009), the contents of which is specifically incorporated herein by reference in its entirety.

In one embodiment, the inventors have employed a single-stranded DNA molecule comprising the sequence of SEQ ID NO:8 (5'-GGGATCGTATAATCGTCGTGCAGT-CAGTCCCTCGGTTAAAGTCTCGAGTCGCTCTGT CAAAATATCCGTACCGTAGTCGATGC-GAGCGAGTCCGATCAGTCCAGGTTTCAAAGT CAAATGACTA-3') as an internal positive control to monitor the fidelity and integrity of the nucleic acids being assayed. Typically, about 0.02 pg/mL of single stranded DNA target was placed into PrimeStore®. In exemplary embodiments, the selected amplification primers and labeled oligonucleotide detection probes preferably each bind to at least a first isolated nucleotide sequence of SEQ ID NO:8. Using the following specific amplification primers, the resulting amplification product is about 100-bp in length:

```
Forward primer:
                                    (SEQ ID NO: 9)
5'-GTGCAGTCAGTCCCTCGGTTA-3'
and Reverse primer:
                                    (SEQ ID NO: 10)
5'-TTGACTTTGAAACCTGGACTGATC-3'.
```

As an illustrative oligonucleotide detection probe specific for this amplification product, the inventors selected the sequence of SEQ ID NO:11 (5'-[FAM]-AAATATCCGTAC-CGTAGTCG-[MGB]-3').

It is important to note that IPCs useful in the practice of the present invention need not include one of the illustrative sequences described herein, nor do the IPCs even need be substantially homologous to any of the IPC sequences enclosed herein. To illustrate this point, the following sequences represent variants of SEQ ID NO:8 that are also functional as carrier DNA/IPC sequences, despite having sequence degeneracy:

The IPCs of the present invention need not be prepared from the precise illustrative DNA amplicon disclosed herein as SEQ ID NO:8. Additional examples of DNA sequences useful in the in vitro preparation of suitable carrier RNA molecules include, without limitation, one or more of the following sequences. In each instance, the polymerase transcription site is shown in single underline, while the sequences of exemplary forward and reverse PCR primer binding domains are shown in double underline. Exemplary sequence domains to which suitable labeled molecular probes are bound are shown in bold.

```
                                    (SEQ ID NO: 12)
5'-X_n TATTAATACGACTCACTATAGGGX_n GTGCAGTCAGTCCCTCG

GTTAAAGTCTCGAGTCGCTCTGTCAAAATATCCGTACCGTAGTCGA

TGCGAGCGAGTCCGATCAGTCCAGGTTTCAAAGTCAAX_n-3',
``` wherein X is any nucleotide and n is any integer from 0 to about 500.

```
                                    (SEQ ID NO: 13)
5'-ATCGTATTAATACGACTCACTATAGGGAATCGTCGTGCAGTC

AGTCCCTCGGTTAAAGTCTCGAGTCGCTCTGTCAAAATATCCGTA

CCGTAGTCGATGCGAGCGAGTCCGATCAGTCCAGGTTTCAAAGT

CAAATGACTA-3'.

(SEQ ID NO: 14)
5'-ATCGTATTAATACGACTCACTATAGGGAATCGTCGTGCAGTC
```

-continued

AGTCCCTCGGTTAAAGTCTCGAGTCGCTCTGTCAAAATATCCGTA

CCGTAGTCGATGCGAGCGAGTCCGAT<u>CAGTCCAGGTTTCAAAGTC</u>

<u>AA</u>AATGACTA-3'.

(SEQ ID NO:15)
5'-ATCGTAT<u>TAATACGACTCACTATAGGG</u>AATCGTCGTG<u>CAGTC</u>

<u>AGTCCCTCGGTTAAAG</u>TCTCGAGTCGCTCTGTCAAAATATCCGTA

CCGTAGTCGATGCGAGCGAG<u>TCCGATCAGTCCAGGTTTCAAAGTC</u>

AAATGACTA-3'.

(SEQ ID NO: 16)
5'-ATAT<u>TAATACGACTCACTATAGGGA</u>GTGCAGTCAGTCCCTCG

<u>GTTA</u>AAGTCTCGAGTCGCTCTGTCAAAATATCCGTACCGTAGTCG

ATGCGAGCGAGTCC<u>GATCAGTCCAGGTTTCAAAGTCAAAT</u>-3'.

(SEQ ID NO: 17)
5'-ATAT<u>TAATACGACTCACTATAGGGA</u>GTGCAGTCAGTCCCTCG

<u>GTTA</u>AAGTCTCGAGTCGCTCTGTCAAAATATCCGTACCGTAGTCG

ATGCGAGCGAGTCC<u>GATCAGTCCAGGTTTCAAAGTCAAAT</u>-3'.

(SEQ ID NO: 18)
5'-ATAT<u>TAATACGACTCACTATAGGGA</u>GTGCAGTCAGTCCCTCG

<u>GTTA</u>AAGTCTCGAGTCGCTCTGTCAAAATATCCGTACCGTAGTCG

ATGCGAGCGAGTCCGA<u>TCAGTCCAGGTTTCAAAGTCAAAT</u>-3'.

(SEQ ID NO: 19)
5'-TAT<u>TAATACGACTCACTATAGGGG</u>TGCAGTCAGTCCCTCGGT

<u>TAA</u>AGTCTCGAGTCGCTCTGTCAAAATATCCGTACCGTAGTCGAT

GCGAGCGAGTCC<u>GATCAGTCCAGGTTTCAAAGTCAA</u>-3'.

(SEQ ID NO: 20)
5'-TAT<u>TAATACGACTCACTATAGGGG</u>TGCAGTCAGTCCCTCGGT

<u>TAA</u>AGTCTCGAGTCGCTCTGTCAAAATATCCGTACCGTAGTCGAT

GCGAGCGAGT<u>CCGATCAGTCCAGGTTTCAAAGTCAA</u>-3'.

(SEQ ID NO: 21)
5'-TAT<u>TAATACGACTCACTATAGGGG</u>TGCAGTCAGTCCCTCGGT

<u>TAA</u>AGTCTCGAGTCGCTCTGTCAAAATATCCGTACCGTAGTCGAT

GCGAGCGA<u>GTCCGATCAGTCCAGGTTTCAAAGTCAA</u>-3'.

IPC DNA Fluorescent Probe Detection

IPC detection probe(s) may include a radioactive, luminescent, chemiluminescent, fluorescent, enzymatic, magnetic, or spin-resonance label, or combination thereof. Fluorescent labels can include fluorescein, 6-carboxyfluorescein (6-FAM), or 6-carboxyfluorescein-N-succinimidyl ester (6-FAMSE), VIC™ dye, or the like, or a combination thereof.

Figure 4:
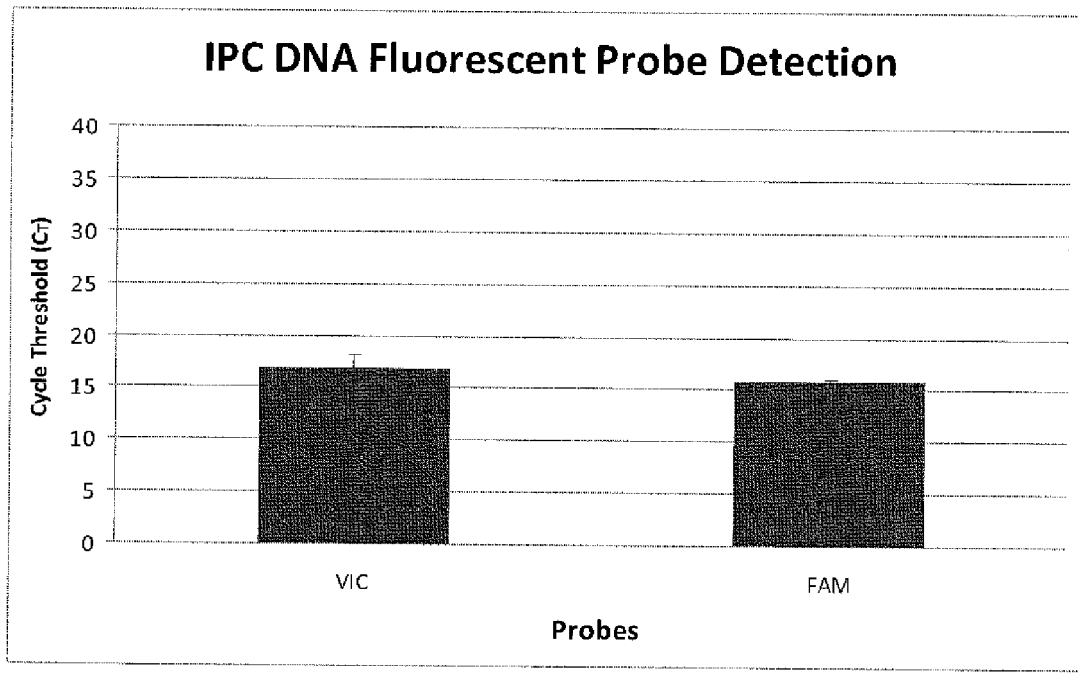
FIG. 4 shows a graph of the RT-PCR analysis when a single stranded DNA internal positive control (IPC) was detected in a PrimeMix® assay using detection probes that were labeled with either 6-FAM (FAM) or VIC™ dye.
Figure 5:
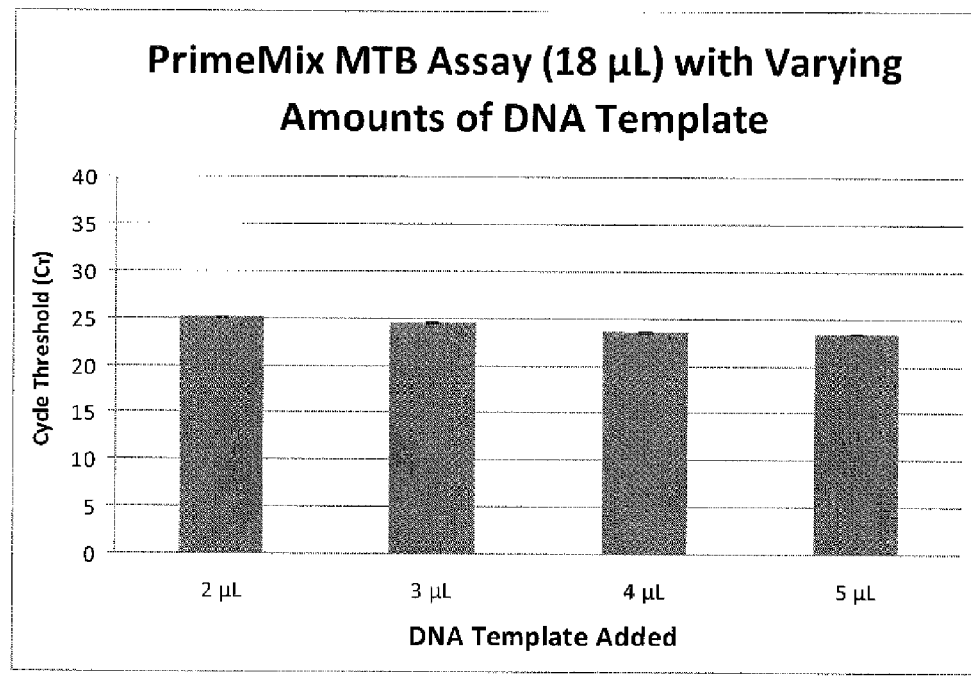
FIG. 5 shows a graph of the RT-PCR analysis when varying amounts of extracted tuberculosis patient DNA, i.e., 2 µl, 3 µl, 4 µl, and 5 µl of template DNA, were used in the PrimeMix® Universal MTB Assay.

IPC detection probe (SEQ ID NO:11) was labeled with either 6-FAM (FAM) or VIC™ dye by methods known to one of ordinary skill in the art, in order to evaluate their effect on detection of the IPC in samples, once RT-PCR was performed. PrimeMix® containing these probes as well as the IPC primers (SEQ ID NO:9 and SEQ ID NO:10) was used to amplify and then detect the presence of the IPC. The experiment was performed four times for each type of labeled probe. Detection was performed using the ABI 7500 Fast Real-Time PCR System (Applied Biosystems™, Life Technologies Corporation, Carlsbad, Calif., USA). As can be seen in FIG. 4, there was no significant difference between the $C_\tau$ values for the IPC detection probe labeled with VIC™ dye ($C_\tau$ value=32.5) and that labeled with 6-FAM ($C_\tau$ value=31.5). Thus, the type of probe label used has minimal to no effect in performing the analysis and evaluation of the presence and quantity of the IPC.

Multiplex Assay: The Use of an Internal Positive Control in Combination with the PrimeMix® Universal MTB Assay As noted above, it is desirable to formulate an IPC sequence that is both non-genomic, and that does not significantly hybridize to a mammalian genome, or to the genome of pathogenic species of interest. This is to avoid the possibility of the IPC primers and probes detecting other nucleic acid(s) present in an extracted patient sample, such as DNA from the patient themselves or from other microorganisms that are not of interest that may be present in the sample.

Figure 6:
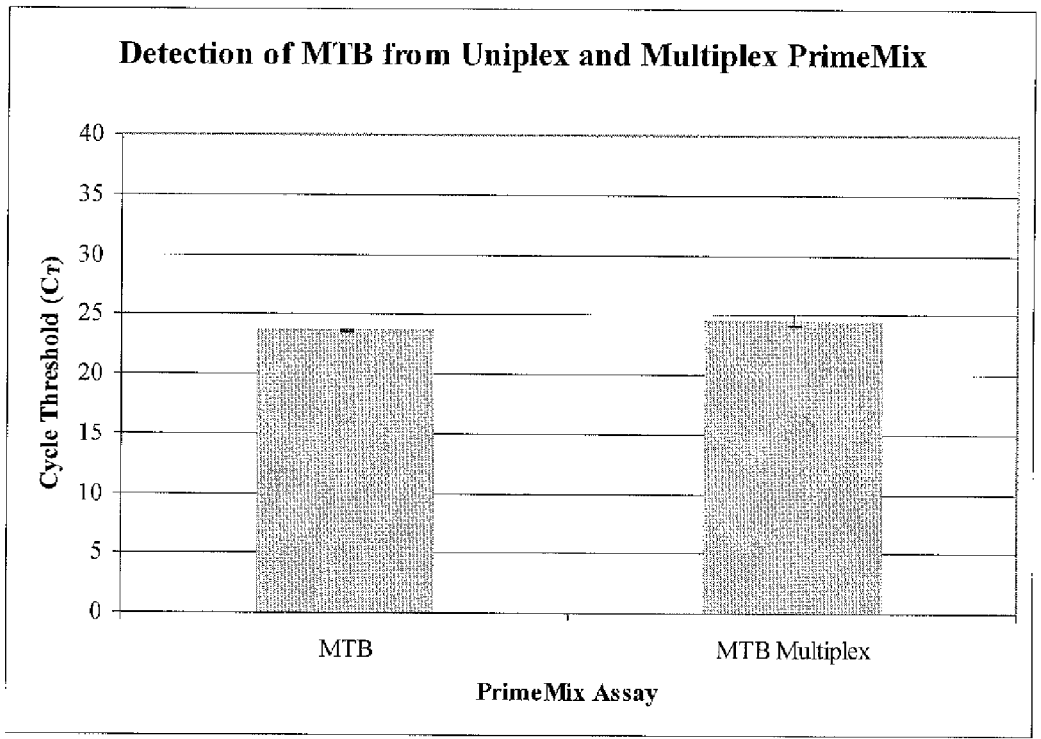
FIG. 6 shows a graph of the RT-PCR analysis when a multiplex PrimeMix® Universal MTB Assay is performed wherein a single stranded DNA internal positive control (IPC) is added to the solution containing the tuberculin sample, as compared to a uniplex assay wherein the initial solution solely contains the biological sample obtained from the patient and the storage solution, i.e., PrimeStore®.

In order to ensure that the IPC, IPC primers and ITC probes of the present invention would not affect or inhibit the amplification or detection of the M. tuberculosis sequence in samples, the single stranded DNA IFC was placed into PrimeStore® containing about 33 ng/μL of previously-identified MDR-M. tuberculosis DNA. The nucleic acid was then extracted using the QIAamp® DNA Mini Kit (Qiagen®) and PrimeMix® containing both primers and probes for M. tuberculosis and the IPC, as described above, were used in a multiplex PrimeMix® Universal MTB Assay. As a comparison, the same procedure was carried out on the same M. tuberculosis strain but no IPC, IPC primers or probes were added. This experiment was carried out in triplicate for both the multiplex and uniplex procedure. As can be seen in FIG. 6, the amplification and detection of M. tuberculosis nucleic acid was not significantly affected by the multiplex procedure, i.e., the average $C_\tau$ value for the multiplex procedure ("MTB Multiplex") was 24.6 whereas the $C_\tau$ value for the uniplex procedure ("MTB") was 23.6.

Uniplex and Multiplex Assays: Varying Concentrations of IPC

Figure 7:
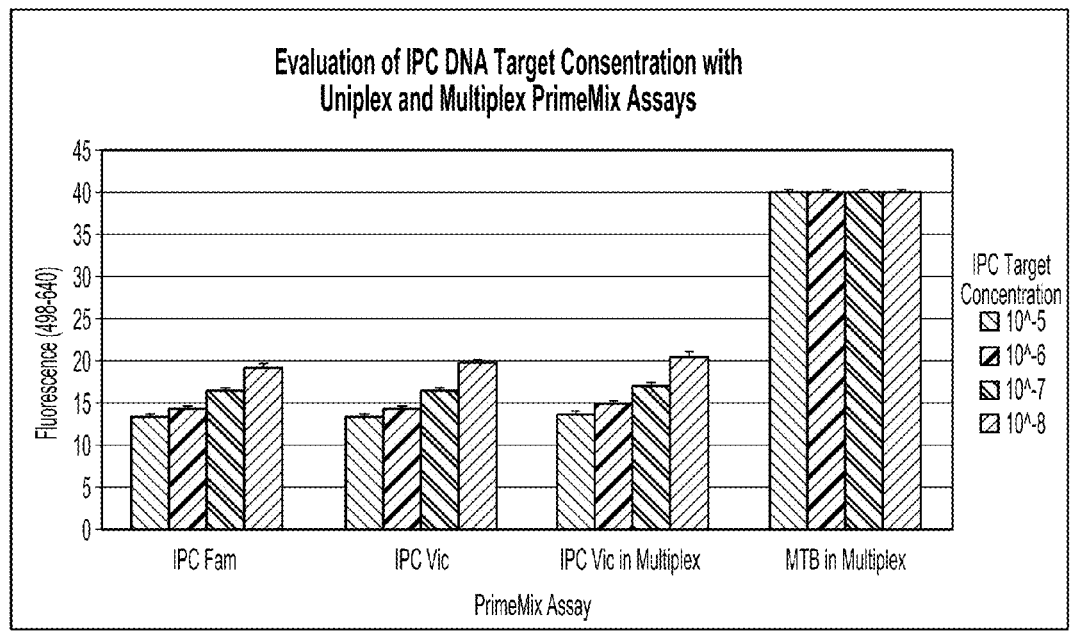
FIG. 7 shows a graph of the RT-PCR analysis when the concentration of the internal positive control ("IPC") placed in PrimeStore® was varied, i.e., $10^{-5}$, $10^{-6}$, $10^{-7}$, and $10^{-8}$ ng/µL of IPC were placed into the same amount of PrimeStore®. The probes for the IPC were either labeled with 6-FAM ("IPC Fam") or VIC™ dye ("IPC Vic"). A multiplex reaction was also carried out, in which *M. tuberculosis* complex-specific primers and probes were also added to the PrimeMix® (results shown in column labeled "MTB in Multiplex"), along with the IPC primers and probes (results shown in column labeled "IPC Vic in Multiplex")

The concentration of the IPC placed in PrimeStore® was varied. $10^{-5}$, $10^{-6}$, $10^{-7}$, and $10^{-8}$ ng/μL of IPC were placed into the same amount of PrimeStore®. Depending on whether a uniplex or multiplex reaction was performed, an M. tuberculosis complex-specific set of primers and probe were also placed in the PrimeMix®. No M. tuberculosis complex-specific nucleic acids were added to the PrimeStore® solution. As can be seen in FIG. 7, varying the concentration of the IPC in PrimeStore® in a multiplex PrimeMix® Universal MTB Assay ("IPC Vic in Multiplex") showed no significant difference when compared to the same concentration variations of 1PC in the uniplex PrimeMix® assay (for IPC only) ("IPC Fam" and "IPC Vic"). Additionally there were no significant differences between the IPC probes labeled with 6-FAM and those labeled with VIC™ dye in a uniplex format when IPC concentration was varied.

Uniplex and Multiplex Assays: Varying Concentrations of M. tuberculosis Sample

Figure 8:
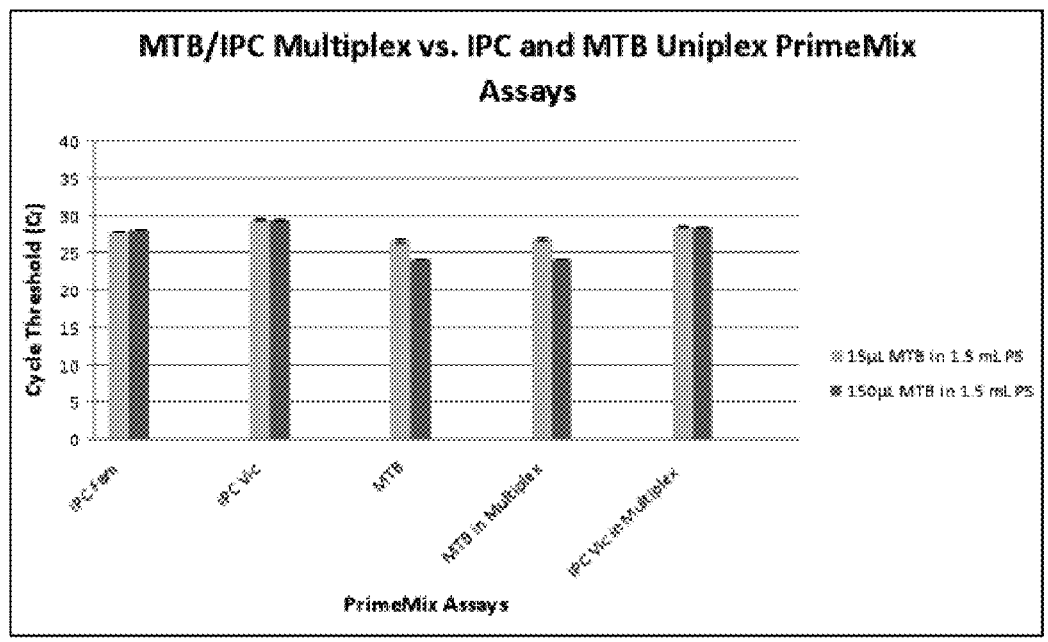
FIG. 8 shows a graph of the RT-PCR analysis when the initial amount of an *M. tuberculosis* sample is 15 µl and 150 µl (a 10-fold difference) when each is initially stored in 1.5 mL of PrimeStore®. This was performed for IPC probes labeled with 6-FAM ("IPC Fam") and VIC™ dye ("IPC Vic"), as well as for uniplex detection of *M. tuberculosis* ("MTB") and multiplex detection of *M. tuberculosis* ("MTB in Multiplex") and the IPC wherein the probe is labeled with VIC™ dye ("IPC Vic in Multiplex")

As can be seen in FIG. 8, increasing the initial amount of M. tuberculosis sample from 15 μL to 150 μL (a 10-fold difference) as initially stored in 1.5 mL of PrimeStore®, slightly improves the results obtained from a uniplex PrimeMix® Universal MTB Assay (average $C_\tau$ value of 15 μL sample=26.5, average $C_\tau$ value of 150 μL sample=24.1) and a multiplex PrimeMix® Universal MTB Assay (average $C_\tau$ value of 15 μL sample=26.8, average $C_\tau$ value of 150 μL sample=24.2). Detection of the IPC remains unaffected as expected. There was little observable difference in MTB PCR amplification, as measured by $C_\tau$ scores between the uniplex and multiplex PrimeMix® Universal MTB Assay.

Uniplex and Multiplex Assays: Detection of *Mycobacterium* Strains

Figure 9:
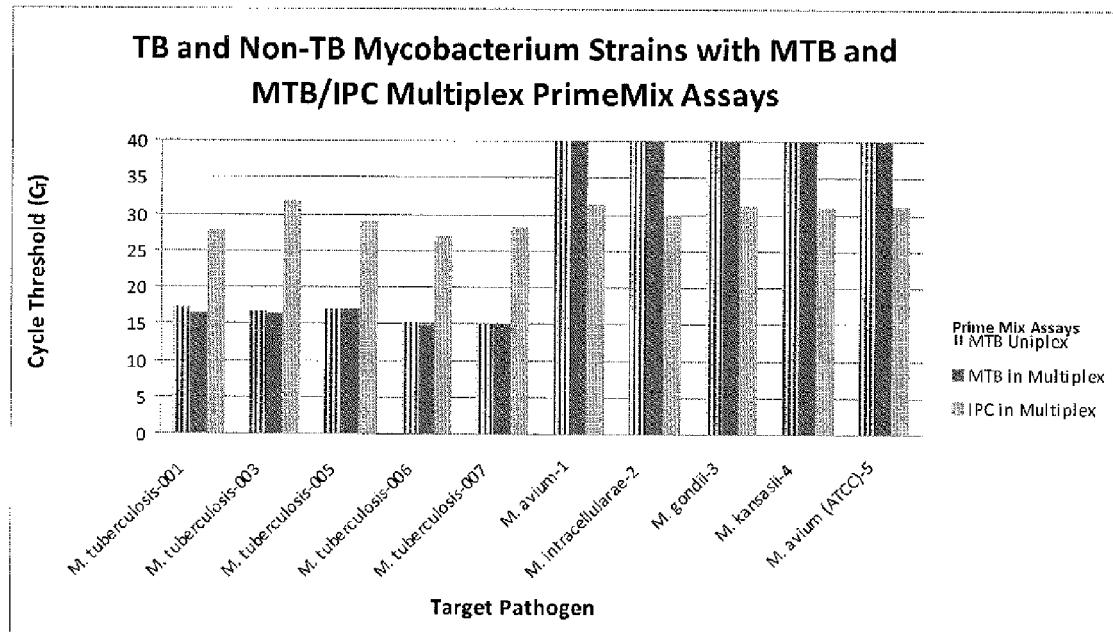
FIG. 9 shows a graph of the RT-PCR analysis when various *mycobacterium* strains, i.e., five different *M. tuberculosis* strains, two different *M. avium* strains, one *M. intracellularae* strain, one *M. gondii* strain, and one *M. kansasii* strain, were placed in and then extracted from PrimeStore® and then analyzed using both the uniplex ("MTB Uniplex") and multiplex ("MTB in Multiplex") formats of the PrimeMix® procedure. The uniplex assay used only *M. tuberculosis* complex-specific primers and probes, whereas the multiplex assay used both *M. tuberculosis* complex-specific primers and probes and IPC-specific primers and probes.

Various mycobacterial strains (i.e., five different *M. tuberculosis* strains, two different *M. avium* strains, one *M. intracellularae* strain, one *M. gondii* strain, and one *M. kansasii* strain) were tested using both the uniplex ("MTB Uniplex") and multiplex ("MTB in Multiplex") PrimeMix® by similar procedures to those described above. Nucleic extraction amounts varied, depending on the contents of the sputum sample from about 80 to about 180 ng/µL. As can be seen in FIG. 9, both the uniplex and multiplex assays readily detected the five different *M. tuberculosis* strains but not the other non-MTB strains. This indicates that the PrimeMix® assay readily detects tuberculosis-causing organisms and not other *Mycobacterium* species. No significant difference was detected between the results for the uniplex and multiplex assays for MTB detection indicating little to no loss of sensitivity between uniplex and multiplex assays. The IPC was readily detected in all multiplex assays, regardless of what mycobacterial strain was used.

Uniplex and Multiplex Assays: Dilution of *M. tuberculosis* Target Pathogen

Figure 10:
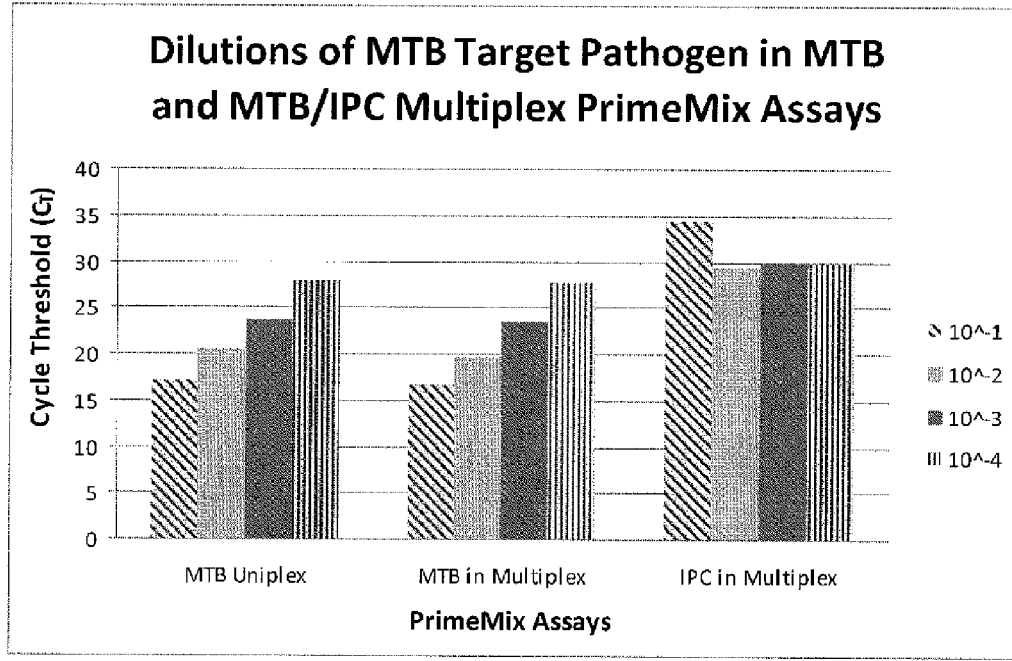
FIG. 10 shows a graph of the RT-PCR analysis when the amount of *M. tuberculosis* from a particular purified strain is varied, i.e., $10^{-4}$, $10^{-3}$, $10^{-2}$, $10^{-1}$ are representative of tenfold dilutions wherein $10^{-1}$ represents a DNA concentration of 330 ng/µL, $10^{-2}$ represents a DNA concentration of 33 ng/µL, $10^{-3}$ represents a DNA concentration of 3.3 ng/µL and $10^{-4}$ represents a DNA concentration of 0.33 ng/µL. A uniplex reaction using PrimeMix® Universal MTB Assay with *M. tuberculosis* complex-specific primers and probes was performed (results shown in "MTB Uniplex" column"), as well as a multiplex PrimeMix® assay in which both *M. tuberculosis* complex-specific primers and probes and IPC-specific primers and probes were present was performed (results shown in "MTB in Multiplex" and "IPC in Multiplex" columns)

As can be seen in FIG. 10, varying the amount of *M. tuberculosis* target sequence concentration from a particular purified strain, i.e., $10^{-4}$, $10^{-3}$, $10^{-2}$, $10^{-1}$ are representative of ten-fold dilutions wherein $10^{-1}$ represents a DNA concentration of 330 ng/µL, $10^{-2}$ represents a DNA concentration of 33 ng/µL, $10^{-3}$ represents a DNA concentration of 3.3 ng/µL and $10^{-4}$ represents a DNA concentration of 0.33 ng/µL, increased the ability of the PrimeMix® assay to detect *M. tuberculosis* significantly, in both the uniplex and multiplex assays. The IPC target sequence concentration was 0.02 pg/mL for each assay. IPC detection was minimally affected by the highest concentration of *M. tuberculosis* nucleic acid, as typically expected in the performance of multiplex assays where the concentration of a target sequence is generally much higher than that of the IPC target. This could be addressed by increasing the concentration of the IPC target sequence in the assay or further molar optimization of the IPC primers and/or probe in the multiplex reaction.

Multiplex Assays: Dilution of *M. tuberculosis* Strain

Figure 11:
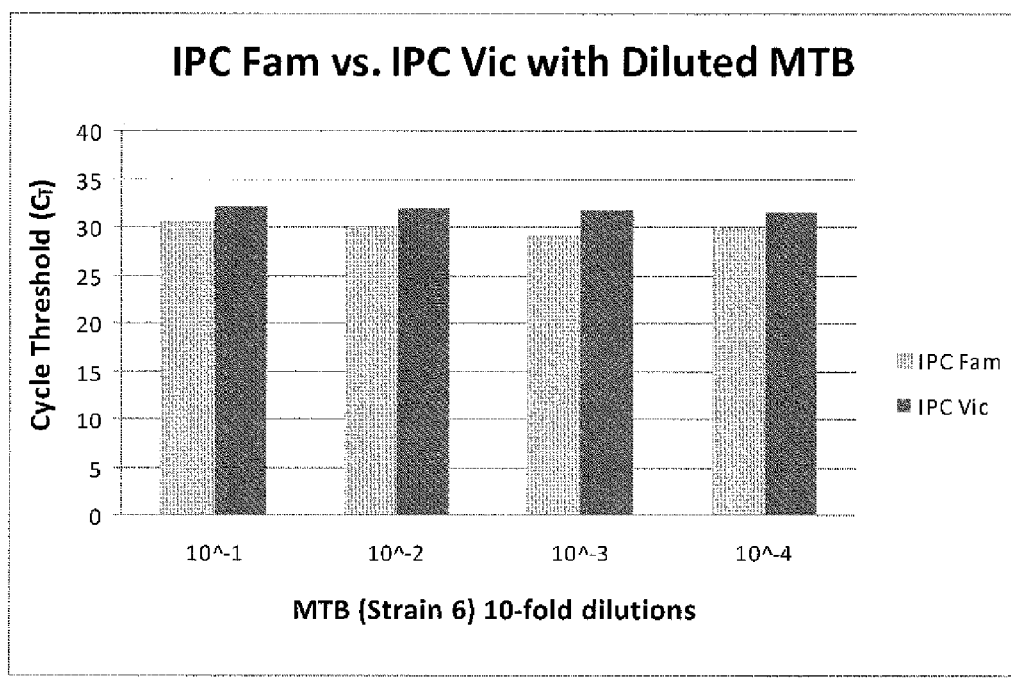
FIG. 11 shows a graph of the RT-PCR analysis when the amount of *M. tuberculosis* from a particular purified strain is varied, i.e., $10^{-4}$, $10^{-3}$, $10^{-2}$, $10^{-1}$ are representative of tenfold dilutions wherein $10^{-1}$ represents a DNA concentration of 33 ng/µL, $10^{-2}$ represents a DNA concentration of 3.3 ng/µL, $10^{-3}$ represents a DNA concentration of 0.33 ng/µL and $10^{-4}$ represents a DNA concentration of 0.033 ng/µL and different labels, either 6-FAM ("IPC Fam") or VIC™ dye ("IPC Vic") on the IPC-specific probe were used.

As can be seen in FIG. 11, varying the amount of *M. tuberculosis* nucleic acid from a particular purified strain, i.e., $10^{-4}$, $10^{-3}$, $10^{-2}$, $10^{-1}$ are representative of ten-fold dilutions wherein $10^{-1}$ represents a DNA concentration of 33 ng/µL, $10^{-2}$ represents a DNA concentration of 3.3 ng/µL, $10^{-3}$ represents a DNA concentration of 0.33 ng/µL and $10^{-4}$ represents a DNA concentration of 0.033 ng/µL, had no significant effect on the detection of the IPC when using IPC probes labeled with either 6-FAM or VIC™ dye. Probes labeled with 6-FAM did show lower $C_\tau$ values overall, but both methods of detection were equally effective.

In light of this disclosure, all compositions and methods disclosed and claimed herein can be made and executed without undue experimentation. While the compositions and methods of this invention have been described in terms of exemplary embodiments, it will be apparent to those of ordinary skill in the art that variations may be applied to the composition, methods and sequence of steps of the methods described herein without departing from the concept, spirit and scope of the invention. More specifically, it will be apparent that certain agents, compounds, components, and/or reagents that are chemically-, functionally-, and/or physiologically-related may be substituted for one or more of the agents, compounds, components, and/or reagents described herein while achieving the same or similar results as embodied herein. All such similar substitutes and modifications apparent to those of ordinary skill in the relevant biological arts are deemed to be within the spirit, scope, and concept of the invention as defined by the appended claims. Accordingly, the exclusive rights sought to be patented are set forth and described in the following claims.

What is claimed is:

1. A method for obtaining a population of mycobacterial-specific polynucleotides from a sample suspected of containing one or more pathogenic mycobacterial cells, which comprises: contacting the sample with an effective amount of a composition that comprises: a) one or more chaotropes; b) one or more detergents; c) one or more reducing agents; d) one or more chelators; e) one or more buffers; and f) one or more surfactants, for a time sufficient to substantially kill or lyse the one or more pathogenic mycobacterial cells therein, but not degrade the population of mycobacterial-specific polynucleotides, and to denature or inactivate proteins, enzymes, and nucleases present therein; such that, after contact with the composition, the sample is safe for handling and transport; and the integrity of the population of mycobacterial-specific polynucleotides is at least substantially maintained when stored at a temperature from about 10° C. to about 40° C. for a period from about 1 day to about 60 days, wherein the composition further comprises a quantity of a control nucleic acid of about 50 to about 500 nucleotides in length, wherein the control nucleic acid does not substantially hybridize to nucleic acids of the sample, and comprises at least 40 contiguous nucleotides of SEQ ID NO:8, or the complement thereof.

2. The method of claim 1, wherein the (i) the one or more chaotropes comprise guanidine thiocyanate, guanidine isocyanate, guanidine hydrochloride, or any combination thereof; (ii) the one or more detergents comprise sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, or any combination thereof; (iii) the one or more reducing agents comprise 2-mercaptoethanol, tris(2-carboxyethyl) phosphine, dithiothreitol, dimethylsulfoxide, or any combination thereof; (iv) the one or more chelators comprise ethylene glycol tetraacetic acid, hydroxyethylethylenediaminetriacetic acid, diethylene triamine pentaacetic acid, N,N-bis(carboxymethyl)glycine, ethylenediaminetetraacetic acid, citrate anhydrous, sodium citrate, calcium citrate, ammonium citrate, ammonium bicitrate, citric acid, diammonium citrate, ferric ammonium citrate, lithium citrate, or any combination thereof; or (v) the one or more buffers comprise tris (hydroxymethyl)aminomethane, citrate, 2-(N-morpholino)ethanesulfonic acid, N,N-Bis(2-hydroxyethyl)-2-aminoethanesulfonic acid, 1,3-bis(tris(hydroxymethyl)methyl amino)propane, 4-(2-hydroxyethyl)-1-piperazine ethanesulfonic acid, 3-(N-morpholino) propanesulfonic acid, bicarbonate, phosphate, or any combination thereof.

3. The method of claim 2, wherein the composition comprises: (a) (i) about 3M guanidine thiocyanate; (ii) about 1 mM TCEP; (iii) about 10 mM sodium citrate; (iv) about 0.5% N-lauroyl sarcosine; (v) about 0.0002% silicone polymer; (vi) about 100 mM 2-amino-2-hydroxymethyl-propane-1,3-diol (TRIS); and (vii) about 0.1 mM EDTA; or (b) (i) about 3M guanidine thiocyanate; (ii) about 1 mM TCEP; (iii) about 10 mM sodium citrate; (iv) about 0.5% N-lauroyl sarcosine, sodium salt; (v) about 0.0002% of a silicone polymer; (vi) about 100 mM TRIS; (vii) about 0.1 mM EDTA; and (viii) about 10% to about 25% ethanol (vol./vol.).

4. The method of claim 1, wherein the sample is of a biological, a clinical, or an environmental origin, and comprises one or more of phlegm, sputum, bronchial lavage, pulmonary aspirate, saliva, plasma, whole blood, serum, cells, tissues, bodily fluids, or any combination thereof.

5. The method of claim 1, wherein the sample contains at least a first *Mycobacterium*-specific nucleic acid segment.

6. The method of claim 5, wherein the first *Mycobacterium*-specific nucleic acid segment is derived from *Mycobacterium tuberculosis, M. bovis, M. africanum, M. microti, M. cannetti, M. caprae*, or *M. pinnipedi*.

7. The method of claim 1, wherein the sample is of human origin.

8. The method of claim 1, wherein the sample is obtained from a human that has, is suspected of having, or is at risk for developing tuberculosis.

9. The method of claim 8, wherein the human has, is suspected of having, or is at risk for developing a secondary bacterial, fungal, or viral infection, or any combination thereof.

10. The method of claim 1, wherein at least a first nucleic acid segment present in the population of mycobacterial-specific polynucleotides is suitable for primer-dependent amplification.

11. The method of claim 1, wherein the population of mycobacterial-specific polynucleotides remains substantially non-degraded upon storage in the composition for a period of about 5 to about 60 days, at an ambient temperature of about 10° C. to about 30° C.

12. The method of claim 1, wherein the population of mycobacterial-specific polynucleotides remains substantially non-degraded upon storage in the composition for a period of about 10 to about 40 days, at an ambient temperature of about 10° C. to about 30° C.

13. The method of claim 1, further comprising detecting within the population of mycobacterial-specific polynucleotides the presence of at least a first *Mycobacterium*-specific nucleic acid segment by contacting the population with a labeled oligonucleotide detection probe, wherein the presence of a labeled hybridization product is indicative of the presence of one or more *Mycobacterium*-specific nucleic acid segments in the population of polynucleotides.

14. The method of claim 13, wherein the labeled oligonucleotide detection probe comprises at least a first sequence region that consists of the sequence of SEQ ID NO:4 or SEQ ID NO:7.

15. The method of claim 1, wherein the control nucleic acid is about 70 to about 250 nucleotides in length.

16. The method of claim 1, wherein the control nucleic acid comprises a single-stranded DNA, a double-stranded DNA, a single-stranded RNA, a double-stranded RNA, or a double-stranded DNA:RNA hybrid.

17. The method of claim 16, wherein the control nucleic acid comprises:
(a) a first sequence domain that specifically binds to a labeled oligonucleotide detection probe of from about 15 to about 35 nucleotides in length;
(b) a second sequence domain that specifically binds to a forward PCR amplification primer of about 15 to about 35 nucleotides in length; and
(c) a third sequence domain that specifically binds to a reverse PCR amplification primer of about 15 to about 35 nucleotides in length;
wherein the second and third sequence domains are operably positioned upstream, and downstream, respectively, of the first sequence domain to facilitate a PCR-directed amplification of at least a first portion of the control nucleic acid.

18. The method of claim 1, wherein the population of mycobacterial-specific polynucleotides is obtained from the sample using an extraction apparatus.

19. The method of claim 18, wherein the extraction apparatus comprises:
(a) a filtration vessel that has at least one receiving end and that comprises a membrane filter adapted to bind the population of polynucleotides thereto, wherein the membrane filter is disposed at least substantially across a width of the filtration vessel and at least partially therein; and
(b) a volume-dispensing mechanism adapted to controllably dispense and forcibly inject an amount of liquid operably associated with the filtration vessel to filter the liquid there through.

20. The method of claim 1, further comprising
(a) performing at least one thermal cycling step, wherein the cycling comprises at least a first amplifying step and at least a first hybridizing step, wherein the at least a first amplifying step comprises contacting the population of polynucleotides with a composition that comprises at least a pair of *Mycobacterium*-specific amplification primers, a thermostable polymerase, a first osmolarity agent comprising betaine, at least a first reference dye, and a plurality of deoxynucleoside triphosphates to produce at least a first *Mycobacterium*-specific amplification product; and
(b) detecting the presence of the amplification product so produced by contacting the amplification product with a first labeled *Mycobacterium*-specific oligonucleotide detection probe, wherein the presence of a labeled hybridization product is indicative of the presence of one or more *Mycobacterium*-specific nucleic acid segments in the population of polynucleotides.

21. The method of claim 20, wherein the pair of *Mycobacterium*-specific amplification primers comprises a first oligonucleotide primer of 18 to about 30 nucleotides in length, and a second oligonucleotide primer of 18 to about 30 nucleotides in length, wherein each of the first and second primers specifically hybridize to a first, and a second distinct sequence region, respectively, within the sequence of SEQ ID NO:1 or the complement thereof.

22. The method of claim 20, further comprising performing a primer-dependent amplification of at least a first sequence region of the control nucleic acid in the population of polynucleotides, and quantitating the amount of amplified control nucleic acid.

23. The method of claim 22, further comprising comparing the amount of the control nucleic acid originally present in the composition to the amount of the amplified nucleic acid segment, wherein the ratio is indicative of the quantity of the population of mycobacterial-specific polynucleotides originally present in the sample.

24. The method of claim 22, wherein the primer-dependent amplification of the least a first sequence region of the control nucleic acid is performed as a single amplification reaction subsequent to the first amplifying step.

25. The method of claim 22, wherein the primer-dependent amplification of the least a first sequence region of the control nucleic acid is performed substantially simultaneously with the first amplifying step.

26. The method of claim 25, wherein the amplification product of the control nucleic acid is detected with an oligonucleotide detection probe comprising a first detectable label, and the amplification product of the *Mycobacterium*-specific nucleic acid segment is detected with an oligonucleotide detection probe comprising a second distinct detectable label.

27. The method of claim 22, wherein the primer-dependent amplification of at least a first sequence region of the control nucleic acid is performed using (a) a forward amplification primer that comprises a sequence region that consists essentially of the sequence of SEQ ID NO:9; (b) a reverse amplification primer that comprises a sequence region that consists essentially of the sequence of SEQ ID NO:10; and (c) a labeled oligonucleotide detection probe that comprises a sequence region that consists essentially of the sequence of SEQ ID NO:11, or the complement thereof.

28. The method of claim 1, further comprising detecting the presence of at least one drug resistance gene within the population of polynucleotides.

29. A method for detecting the presence of a *Mycobacterium*-specific nucleic acid segment in the population of polynucleotides obtained from the method of claim 1, comprising:
(a) performing at least one thermal cycling step, wherein the cycling comprises at least a first amplifying step and at least a first hybridizing step, wherein the at least a first amplifying step comprises contacting the population of polynucleotides with a composition that comprises at least a pair of *Mycobacterium*-specific amplification primers, a polymerase, a first osmolarity agent comprising betaine, and a plurality of deoxynucleoside triphosphates to produce a *Mycobacterium*-specific amplification product when a *Mycobacterium*-specific nucleic acid segment is present in the sample; and
(b) detecting the presence of the amplification product by contacting the amplification product with a labeled *Mycobacterium*-specific oligonucleotide detection probe, wherein the presence of a labeled hybridization product is indicative of the presence of one or more *Mycobacterium*-specific nucleic acid segments in the population of polynucleotides,
wherein the pair of *Mycobacterium*-specific amplification primers comprises a first oligonucleotide primer of 18 to about 30 nucleotides in length, and a second oligonucleotide primer of 18 to about 30 nucleotides in length, wherein each of the first and second primers specifically hybridizes to a first, and a second sequence region, respectively, within the sequence of SEQ ID NO:1, or the complement thereof.

30. The method of claim 29, wherein the composition used in the at least one thermal cycling step further comprises a first reference dye.

31. The method of claim 30, wherein the first reference dye comprises a passive reference dye.

32. The method of claim 29, wherein (a) at least one of the pair of amplification primers comprises: (i) a first oligonucleotide primer of 18 to about 30 nucleotides in length that comprises at least a first sequence region consisting of a sequence that is at least 90% identical to the nucleic acid sequence of SEQ ID NO 2, or SEQ ID NO 5; or (ii) a second oligonucleotide primer of 18 to about 30 nucleotides in length that comprises at least a second sequence region consisting of a sequence that is at least 90% identical to the nucleic acid sequence of SEQ ID NO 3, or SEQ ID NO 6; and (b) a *Mycobacterium*-specific oligonucleotide detection probe of 24 to about 35 nucleotides in length that comprises at least a third sequence region consisting of a sequence that is at least 90% identical to the nucleic acid sequence of SEQ ID NO 4, or SEQ ID NO 7, or the complement of either SEQ ID NO 4 or SEQ ID NO 7.

33. The method of claim 29, wherein the method is compatible with at least one high throughput polymerase chain reaction technology.

34. The method of claim 29, wherein the *Mycobacterium*-specific nucleic acid segment is specific for *M. tuberculosis, M. bovis, M. africanum, M. microti, M. cannetti, M. caprae, M. pinnipedi*, or any combination thereof.

35. The method of claim 29, further comprising determining the nucleic acid sequence of the detected *Mycobacterium*-specific nucleic acid segment.

36. A method for obtaining a population of mycobacterial-specific polynucleotides from a sample suspected of containing one or more pathogenic mycobacterial cells, which comprises: adding a control nucleic acid to the sample and contacting the sample with an effective amount of a composition that comprises: a) one or more chaotropes; b) one or more detergents; c) one or more reducing agents; d) one or more chelators; e) one or more buffers; and f) one or more surfactants, which are together exposed to the sample for a time sufficient to substantially kill or lyse the one or more pathogenic mycobacterial cells therein, but not degrade the population of mycobacterial-specific polynucleotides, and to denature or inactivate proteins, enzymes, and nucleases present therein; such that, after contact with the composition, the sample is safe for handling and transport; and the integrity of the population of mycobacterial-specific polynucleotides is at least substantially maintained when stored at a temperature from about 10° C. to about 40° C. for a period from about 1 day to about 60 days, further comprising performing a primer-dependent amplification of at least a first sequence region of the control nucleic acid and quantitating the amount of amplified nucleic acid segment, wherein the primer-dependent amplification of at least a first sequence region of the control nucleic acid is performed using (i) a forward amplification primer that comprises a sequence region that consists essentially of the sequence of SEQ ID NO:9; (ii) a reverse amplification primer that comprises a sequence region that consists essentially of the sequence of SEQ ID NO:10; and (iii) a labeled oligonucleotide detection probe that comprises a sequence region that consists essentially of the sequence of SEQ ID NO:11, or the complement thereof.

37. The method of claim 36, wherein the a) the one or more chaotropes comprise guanidine thiocyanate, guanidine isocyanate, guanidine hydrochloride, or any combination thereof; b) the one or more detergents comprise sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, or any combination thereof; c) the one or more reducing agents comprise 2-mercaptoethanol, tris(2-carboxyethyl) phosphine, dithiothreitol, dimethylsulfoxide, or any combination thereof; d) the one or more chelators comprise ethylene glycol tetraacetic acid, hydroxyethylethylenediaminetriacetic acid, diethylene triamine pentaacetic acid, N,N-bis(carboxymethyl)glycine, ethylenediaminetetraacetic acid, citrate anhydrous, sodium citrate, calcium citrate, ammonium citrate, ammonium bicitrate, citric acid, diammonium citrate, ferric ammonium citrate, lithium citrate, or any combination thereof; or e) the one or more buffers comprise tris (hydroxymethyl)aminomethane, citrate, 2-(N-morpholino)ethanesulfonic acid, N,N-Bis(2-hydroxyethyl)-2-aminoethanesulfonic acid, 1,3-bis(tris (hydroxymethyl)methyl amino)propane, 4-(2-hydroxyethyl)-1-piperazine ethanesulfonic acid, 3-(N-morpholino) propanesulfonic acid, bicarbonate, phosphate, or any combination thereof.

38. The method of claim 37, wherein the composition comprises: (a) (i) about 3 M guanidine thiocyanate; (ii) about 1 mM TCEP; (iii) about 10 mM sodium citrate; (iv) about 0.5% N-lauroyl sarcosine; (v) about 0.0002% silicone polymer; (vi) about 100 mM 2-amino-2-hydroxymethyl-propane- 1,3-diol (TRIS); and (vii) about 0.1 mM EDTA; or (b) (i) about 3M guanidine thiocyanate; (ii) about 1 mM TCEP; (iii) about 10 mM sodium citrate; (iv) about 0.5% N-lauroyl sarcosine, sodium salt; (v) about 0.0002% of a silicone polymer; (vi) about 100 mM TRIS; (vii) about 0.1 mM EDTA; and (viii) about 10% to about 25% ethanol (vol./vol.).

39. The method of claim 36, wherein the sample is of a biological, a clinical, or an environmental origin, and comprises one or more of phlegm, sputum, bronchial lavage, pulmonary aspirate, saliva, plasma, whole blood, serum, cells, tissues, bodily fluids, or any combination thereof.

40. The method of claim 36, wherein the sample contains at least a first *Mycobacterium*-specific nucleic acid segment.

41. The method of claim 40, wherein the first *Mycobacterium*-specific nucleic acid segment is derived from *Mycobacterium tuberculosis*, *M. bovis*, *M. africanum*, *M. microti*, *M. cannetti*, *M. caprae*, or *M. pinnipedi*.

42. The method of claim 36, wherein the sample is of human origin.

43. The method of claim 36, wherein the sample is obtained from a human that has, is suspected of having, or is at risk for developing tuberculosis.

44. The method of claim 43, wherein the human has, is suspected of having, or is at risk for developing a secondary bacterial, fungal, or viral infection, or any combination thereof.

45. The method of claim 36, wherein at least a first nucleic acid segment present in the population of mycobacterial-specific polynucleotides is suitable for primer-dependent amplification.

46. The method of claim 36, wherein the population of mycobacterial-specific polynucleotides remains substantially non-degraded upon storage in the composition for a period of about 5 to about 60 days, at an ambient temperature of about 10° C. to about 30° C.

47. The method of claim 36, wherein the population of mycobacterial-specific polynucleotides remains substantially non-degraded upon storage in the composition for a period of about 10 to about 40 days, at an ambient temperature of about 10° C. to about 30° C.

48. The method of claim 36, further comprising detecting within the population of mycobacterial-specific polynucleotides the presence of at least a first *Mycobacterium*-specific nucleic acid segment by contacting the population with a labeled oligonucleotide detection probe, wherein the presence of a labeled hybridization product is indicative of the presence of one or more *Mycobacterium*-specific nucleic acid segments in the population of polynucleotides.

49. The method of claim 48, wherein the labeled oligonucleotide detection probe comprises at least a first sequence region that consists of the sequence of SEQ ID NO:4 or SEQ ID NO:7.

50. The method of claim 36, wherein the control nucleic acid is about 50 to about 500 nucleotides in length and does not substantially hybridize to nucleic acids of the sample.

51. The method of claim 36, wherein the control nucleic acid is of about 70 to about 250 nucleotides in length.

52. The method of claim 36, wherein the control nucleic acid comprises a single-stranded DNA, a double-stranded DNA, a single-stranded RNA, a double-stranded RNA, or a double-stranded DNA:RNA hybrid.

53. The method of claim 36, wherein the control nucleic acid comprises an at least 40 contiguous nucleotide sequence from SEQ ID NO:8, or the complement thereof.

54. The method of claim 36, wherein the control nucleic acid comprises:

(a) a first sequence domain that specifically binds to a labeled oligonucleotide detection probe of from about 15 to about 35 nucleotides in length;
(b) a second sequence domain that specifically binds to a forward PCR amplification primer of about 15 to about 35 nucleotides in length; and
(c) a third sequence domain that specifically binds to a reverse PCR amplification primer of about 15 to about 35 nucleotides in length;
wherein the second and third sequence domains are operably positioned upstream, and downstream, respectively, of the first sequence domain to facilitate a PCR-directed amplification of at least a first portion of the control nucleic acid from the forward and reverse primers under conditions effective to amplify the at least a first portion.

55. The method of claim 36, wherein the population of mycobacterial-specific polynucleotides is obtained from the sample using an extraction apparatus.

56. The method of claim 55, wherein the extraction apparatus comprises:

(a) a filtration vessel that has at least one receiving end and that comprises a membrane filter adapted to bind the population of polynucleotides thereto, wherein the membrane filter is disposed at least substantially across a width of the filtration vessel and at least partially therein; and
(b) a volume-dispensing mechanism adapted to controllably dispense and forcibly inject an amount of liquid operably associated with the filtration vessel to filter the liquid therethrough.

57. The method of claim 36, further comprising (a) performing at least one thermal cycling step, wherein the cycling comprises at least a first amplifying step and at least a first hybridizing step, wherein the at least a first amplifying step comprises contacting the population of polynucleotides with a composition that comprises at least a pair of *Mycobacterium*-specific amplification primers, a thermostable polymerase, a first osmolarity agent comprising betaine, at least a first reference dye, and a plurality of deoxynucleoside triphosphates to produce at least a first *Mycobacterium*-specific amplification product; and
(b) detecting the presence of the amplification product so produced by contacting it with a first labeled *Mycobacterium*-specific oligonucleotide detection probe, wherein the presence of a labeled hybridization product is indicative of the presence of one or more *Mycobacterium*-specific nucleic acid segments in the population of polynucleotides.

58. The method of claim 57, wherein the pair of *Mycobacterium*-specific amplification primers comprises a first oligonucleotide primer of 18 to about 30 nucleotides in length, and a second oligonucleotide primer of 18 to about 30 nucleotides in length, wherein each of the first and second primers specifically hybridize to a first, and a second distinct sequence region, respectively, within the sequence of SEQ ID NO:1 or the complement thereof.

59. The method of claim 36, further comprising comparing the amount of the control nucleic acid originally present in the composition to the amount of the amplified nucleic acid, wherein the ratio is indicative of the quantity of the population of mycobacterial-specific polynucleotides originally present in the sample.

60. The method of claim 22, wherein the amplification product of the control nucleic acid is detected with an oligonucleotide detection probe comprising a detectable label that is distinct from the first labeled *Mycobacterium*-specific oligonucleotide detection probe.

61. The method of claim 36, further comprising detecting the presence of at least one drug resistance gene within the population of polynucleotides.

* * * * *